(12) United States Patent
Kato et al.

(10) Patent No.: US 9,046,766 B2
(45) Date of Patent: Jun. 2, 2015

(54) ACTINIC RAY-SENSITIVE OR RADIATION-SENSITIVE RESIN COMPOSITION AND PATTERN FORMING METHOD USING SAME

(75) Inventors: Takayuki Kato, Haibara-gun (JP); Michihiro Shirakawa, Haibara-gun (JP); Hyou Takahashi, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 880 days.

(21) Appl. No.: 12/499,515

(22) Filed: Jul. 8, 2009

(65) Prior Publication Data

US 2010/0009288 A1    Jan. 14, 2010

Related U.S. Application Data

(60) Provisional application No. 61/080,450, filed on Jul. 14, 2008.

(30) Foreign Application Priority Data

Jul. 9, 2008 (JP) ................................. 2008-179228
Jun. 19, 2009 (JP) ................................. 2009-146250

(51) Int. Cl.
| | | |
|---|---|---|
| G03F 7/004 | (2006.01) | |
| G03F 7/30 | (2006.01) | |
| C07C 303/32 | (2006.01) | |
| C07C 309/04 | (2006.01) | |
| C07C 309/06 | (2006.01) | |
| C07C 309/12 | (2006.01) | |
| C07C 309/13 | (2006.01) | |
| C07C 309/19 | (2006.01) | |
| G03F 7/039 | (2006.01) | |
| G03F 7/20 | (2006.01) | |
| G03F 7/11 | (2006.01) | |

(52) U.S. Cl.
CPC ............ *G03F 7/0045* (2013.01); *C07C 309/13* (2013.01); *C07C 309/04* (2013.01); *C07C 309/06* (2013.01); *C07C 309/19* (2013.01); *C07C 309/12* (2013.01); *C07C 303/32* (2013.01); *G03F 7/0046* (2013.01); *G03F 7/0397* (2013.01); *G03F 7/11* (2013.01); *G03F 7/2041* (2013.01)

(58) Field of Classification Search
CPC ... G03F 7/0045; G03F 7/0397; C07C 309/04; C07C 309/06; C07C 309/12; C07C 309/13; C07C 309/19
USPC .............. 430/270.1, 326, 910, 921, 922; 562/100, 109, 113
See application file for complete search history.

(56) References Cited

U.S. PATENT DOCUMENTS

| | | | |
|---|---|---|---|
| 6,749,987 B2 * | 6/2004 | Kodama et al. ............ | 430/270.1 |
| 6,849,374 B2 * | 2/2005 | Cameron et al. ........... | 430/270.1 |
| 7,022,459 B2 * | 4/2006 | Kodama ..................... | 430/270.1 |
| 7,262,321 B2 * | 8/2007 | Harada et al. .............. | 430/270.1 |
| 7,304,175 B2 * | 12/2007 | Harada et al. ................. | 560/129 |
| 7,629,107 B2 * | 12/2009 | Shibuya et al. ............ | 430/270.1 |
| 7,803,513 B2 | 9/2010 | Yamaguchi et al. | |
| 7,871,752 B2 | 1/2011 | Hasegawa et al. | |
| 8,062,831 B2 | 11/2011 | Shinachi et al. | |
| 2002/0102491 A1 | 8/2002 | Kodama et al. | |
| 2003/0224285 A1 | 12/2003 | Nakao et al. | |
| 2008/0026331 A1 | 1/2008 | Hasegawa et al. | |
| 2008/0085464 A1 * | 4/2008 | Shibuya et al. ............ | 430/270.1 |
| 2008/0176168 A1 | 7/2008 | Araki et al. | |
| 2008/0193874 A1 | 8/2008 | Takata et al. | |
| 2008/0206669 A1 * | 8/2008 | Kato et al. ................. | 430/270.1 |
| 2008/0227025 A1 * | 9/2008 | Kanda ........................ | 430/270.1 |
| 2008/0248423 A1 | 10/2008 | Yamaguchi et al. | |
| 2008/0305429 A1 * | 12/2008 | Saegusa et al. ............ | 430/270.1 |
| 2009/0011362 A1 * | 1/2009 | Tarutani et al. ............ | 430/270.1 |
| 2009/0042132 A1 | 2/2009 | Irie et al. | |
| 2009/0081581 A1 * | 3/2009 | Kodama et al. ............ | 430/270.1 |
| 2009/0274984 A1 | 11/2009 | Shinachi et al. | |

FOREIGN PATENT DOCUMENTS

| | | | |
|---|---|---|---|
| CN | 101211113 A | 12/2007 | |
| EP | 0 955 562 A | 11/1999 | |
| EP | 1 600 437 A | 11/2005 | |
| EP | 1 030 221 A | 8/2008 | |

(Continued)

OTHER PUBLICATIONS

Japanese Office Action issued in application No. 2009-146250 dated Mar. 12, 2013.
Japanese Office Action dated Jan. 21, 2014 issued in corresponding application No. 2009-146250.
Taiwanese Office Action issued corresponding Application No. 098123161 dated Jan. 13, 2014.
Taiwanese Office Action issued application No. 098123161 dated Dec. 4, 2014.

* cited by examiner

*Primary Examiner* — John Chu
(74) *Attorney, Agent, or Firm* — Sughrue Mion, PLLC

(57) ABSTRACT

An actinic ray-sensitive or radiation-sensitive resin composition comprises (A) a resin that exhibits an increased solubility in an alkali developer when acted on by an acid, and (B) at least two types of sulfonic acid generators that generate a sulfonic acid when exposed to actinic rays or radiation, wherein the two types of sulfonic acid generators (B) consist of sulfonic acid generators (B1) and (B2) satisfying the following requirements, namely the sulfonic acid generator (B1) generates a sulfonic acid composed of 9 to 20 elements with an acid strength (pKa) satisfying the relationship $pKa<-3.50$, and the sulfonic acid generator (B2) generates an acid composed of 17 or more elements with an acid strength (pKa) satisfying the relationship $-2.00>pKa \geq -3.50$, provided that no hydrogen atom is included in the number of elements of the generated acids.

16 Claims, No Drawings

(56) References Cited

FOREIGN PATENT DOCUMENTS

| | | |
|---|---|---|
| GB | 2 445 275 A | 7/2008 |
| JP | 2003-015296 A | 1/2003 |
| JP | 2003-167347 A | 6/2003 |
| JP | 2003-223001 A | 8/2003 |
| JP | 2004-45856 A | 2/2004 |
| JP | 2005-173549 A | 6/2005 |
| JP | 2006-322988 A | 11/2006 |
| JP | 2007-297590 A | 11/2007 |
| JP | 2008-31298 A | 2/2008 |
| JP | 2008-233613 A | 10/2008 |
| JP | 2009-008824 A | 1/2009 |
| JP | 2009-269845 A | 11/2009 |
| TW | 200801810 A | 2/1996 |
| TW | 536663 B | 6/2003 |

ACTINIC RAY-SENSITIVE OR RADIATION-SENSITIVE RESIN COMPOSITION AND PATTERN FORMING METHOD USING SAME

CROSS-REFERENCE TO RELATED APPLICATIONS

This application claims the benefit of U.S. Provisional Application No. 61/080,450, filed Jul. 14, 2008.

This application is based upon and claims the benefit of priority from prior Japanese Patent Applications No. 2008-179228, filed Jul. 9, 2008; and No. 2009-146250, filed Jun. 19, 2009, the entire contents of both of which are incorporated herein by reference.

BACKGROUND OF THE INVENTION

1. Field of the Invention

The present invention relates to an actinic ray-sensitive or radiation-sensitive resin composition for use in a process for producing a semiconductor such as an IC, a process for producing a circuit board for e.g., a thermal head or a liquid crystal, and other photofabrication processes, and relates to a method of forming a pattern with the use of the composition. More particularly, the present invention relates to an actinic ray-sensitive or radiation-sensitive resin composition that finds appropriate application when an exposure light source emits 250 nm or shorter, preferably 220 nm or shorter wavelength far ultraviolet rays, electron beams or the like, and also relates to a method of forming a pattern with the use of the composition.

In the present invention, the terms "actinic rays" and "radiation" mean, for example, a mercury lamp bright line spectrum, far ultraviolet rays represented by an excimer laser, extreme ultraviolet rays, X-rays, electron beams and the like. In the present invention, the term "light" means actinic rays or radiation.

2. Description of the Related Art

A chemical amplification photosensitive composition is a pattern forming material that is capable of, upon exposure to far ultraviolet or other radiation, generating an acid at the exposed area and, by a reaction catalyzed by the acid, changing the solubility in a developer between the area having been exposed to actinic radiation and the nonexposed area to thereby attain pattern formation on a substrate.

In the use of a KrF excimer laser as an exposure light source, a resin whose fundamental skeleton consists of a poly(hydroxystyrene) exhibiting a low absorption mainly in the region of 248 nm is employed as a major component. Accordingly, there can be attained a high sensitivity, high resolving power and favorable pattern formation. Thus, a system superior to the conventional naphthoquinone diazide/novolak resin system is realized.

On the other hand, in the use of a light source of a further shorter wavelength, for example, an ArF excimer laser (193 nm) as an exposure light source, as the compounds having an aromatic group inherently exhibit a sharp absorption in the region of 193 nm, the above-mentioned chemical amplification system has not been satisfactory.

Therefore, resists for an ArF excimer laser containing a resin with an alicyclic hydrocarbon structure have been developed. For example, the patent references (1) and (2) describe compositions containing resins each simultaneously having a polycyclic acid-decomposable repeating unit and a non-acid-decomposable repeating unit.

These resins without exception provide a chemical amplification resist having a protective group that is dissociated by an acid, thus being unstable to acids. However, in the current situation in which a further nanonization of resist pattern is demanded, it has become difficult to obtain a satisfactory resist performance by the employment of these resins only. Accordingly, ingenuity is being exercised on other components of the photoresist composition, for example, an acid generator, and study is being made on the simultaneous use of two or more types of acid generators (see, for example, the patent reference (3)).

However, the conventional resist compositions still have drawbacks. A further improvement is demanded on the Line width roughness (LWR), exposure latitude and pattern collapse performance thereof.

[Patent reference (1)] Jpn. Pat. Appln. KOKAI Publication No. (hereinafter referred to as JP-A-) 2003-167347,
[Patent reference (2)] JP-A-2003-223001, and
[Patent reference (3)] JP-A-2005-173549.

BRIEF SUMMARY OF THE INVENTION

The present invention has been made in view of the above background of the art. It is an object of the present invention to provide an actinic ray-sensitive or radiation-sensitive resin composition that finds applications in the formation of nanonized patterns for semiconductor production and that is superior to the conventional products in the exposure latitude, LWR and pattern collapse performance.

The inventors have conducted extensive and intensive studies with a view toward attaining the above object, and have found that an actinic ray-sensitive or radiation-sensitive resin composition excelling in the exposure latitude, LWR and pattern collapse performance can be obtained by the employment of a combination of a plurality of specified acid generators. Moreover, it has been found that a further performance enhancement can be realized by an optimum combination of acid generators specified from the viewpoint of acid strength and diffusion.

The present invention has been developed on the basis of the above findings, and the object of the present invention has been attained by the present invention set forth below.

(1) An actinic ray-sensitive or radiation-sensitive resin composition comprising:

(A) a resin that exhibits an increased solubility in an alkali developer when acted on by an acid, and (B) at least two types of sulfonic acid generators that generate a sulfonic acid when exposed to actinic rays or radiation, wherein the two types of sulfonic acid generators (B) consist of sulfonic acid generators (B1) and (B2) satisfying the following requirements, namely:

the sulfonic acid generator (B1) generates a sulfonic acid composed of 9 to 20 elements with an acid strength (pKa) satisfying the relationship pKa<−3.50, and the sulfonic acid generator (B2) generates a sulfonic acid composed of 17 or more elements with an acid strength (pKa) satisfying the relationship −2.00>pKa≥−3.50, provided that no hydrogen atom is included in the number of elements of the generated acids.

(2) The actinic ray-sensitive or radiation-sensitive resin composition according to item (1), wherein no benzene ring structure is contained in the acids generated by the sulfonic acid generators (B1) and (B2).

(3) The actinic ray-sensitive or radiation-sensitive resin composition according to item (1) or (2), wherein the sulfonic acid generator (B1) contains an anionic structure of the formula Ra—$CF_2$—$CF_2$—$SO_3^-$ in which Ra represents a structure consisting of any one, or a combination of two or more members, selected from among an oxygen atom, a sulfur atom, a nitrogen atom, a carbon atom, a hydrogen atom and a fluorine atom, while the sulfonic acid generator (B2) contains an anionic structure of the formula Rb—X—$CF_2$—$SO_3^-$ in which X represents a structure selected from among $CH_2$, C=O, CRbH and $CRb_2$, and Rb represents a structure consisting of any one, or a combination of two or more members, selected from among an oxygen atom, a sulfur atom, a nitrogen atom, a carbon atom and a hydrogen atom.

(4) The actinic ray-sensitive or radiation-sensitive resin composition according to any of items (1) to (3), wherein the sulfonic acid generator (B2) contains an alicyclic group.

(5) The actinic ray-sensitive or radiation-sensitive resin composition according to any of items (1) to (4), further comprising two or more types of acid diffusion inhibitors (C) capable of controlling the diffusion of the acids generated from the sulfonic acid generators (B).

(6) A method of forming a pattern, comprising the steps of applying the actinic ray-sensitive or radiation-sensitive resin composition according to any of items (1) to (5) onto a substrate, exposing the substrate to actinic rays or radiation and developing the exposed substrate with a developer.

In the present invention, the term "composed of X elements" means "containing X atoms other than hydrogen".

The present invention has made it feasible to provide an actinic ray-sensitive or radiation-sensitive resin composition that is improved in the exposure latitude, LWR and pattern collapse performance, thereby being suitable for use in the formation of a nanonized pattern for semiconductor production.

DETAILED DESCRIPTION OF THE INVENTION

The present invention will be described in detail below.

With respect to the expression of a group (atomic group) used in this specification, the expression even when there is no mention of "substituted and unsubstituted" encompasses groups not only having no substituent but also having substituents. For example, the expression "alkyl groups" encompasses not only alkyls having no substituent (unsubstituted alkyls) but also alkyls having substituents (substituted alkyls).

In this specification, mass % is equal to weight %.

1. Sulfonic Acid Generator that when Exposed to Actinic Rays or Radiation, Generates a Sulfonic Acid (Sulfonic Acid Generator (B))

The combination of at least two types of specified acid generators characterizing the present invention will be described in detail below.

The actinic ray-sensitive or radiation-sensitive resin composition of the present invention is characterized in that it contains at least two types of sulfonic acid generators (B) that when exposed to actinic rays or radiation, generate a sulfonic acid, which two types of sulfonic acid generators satisfy the following requirements.

The sulfonic acid generator (B1) is characterized in that when exposed to actinic rays or radiation, it generates a sulfonic acid (hereinafter referred also as the "generated acid" or the like) composed of 9 to 20 elements with an acid strength (pKa) satisfying the relationship pKa<−3.50, and the sulfonic acid generator (B2) is characterized in that it generates a sulfonic acid composed of 17 or more elements with an acid strength (pKa) satisfying the relationship −2.00>pKa≥−3.50, provided that no hydrogen atom is included in the number of elements of the generated acids.

In the present invention, the acid strength (pKa) is an index for quantitatively expressing the strength of an acid and has the same meaning as the acidity constant. The acid strength (pKa) refers to, upon contemplation of a dissociation reaction in which a hydrogen ion is released from an acid, the equilibrium constant (Ka) of the reaction expressed by the negative common logarithm (pKa) thereof. The smaller the value of pKa, the stronger the acid. In the present invention, the acid strength (pKa) is calculated by a calculation using an analysis software package ACD/pKa DB V8.0 produced by ACD (Advanced Chemistry Development).

As each of the sulfonic acid generators (B), use can be made of a member appropriately selected from among a photoinitiator for photocationic polymerization, a photoinitiator for photoradical polymerization, a photo-achromatic agent and photo-discoloring agent of dyes, any of publicly known compounds that when irradiated with actinic rays or radiation, generate an acid, are employed in microresists, etc., and mixtures thereof.

For example, there can be mentioned a phosphonium salt, a sulfonium salt, an iodonium salt, an imide sulfonate or an oxime sulfonate.

Further, use can be made of compounds obtained by introducing any of these groups or compounds that when irradiated with actinic rays or radiation, generate an acid in a polymer principal chain or side chain; for example, compounds described in U.S. Pat. No. 3,849,137, DE 3,914,407, JP-A's 63-26653, 55-164824, 62-69263, 63-146038, 63-163452, 62-153853, 63-146029, etc.

Furthermore, use can be made of compounds that when irradiated with light, generate an acid described in U.S. Pat. No. 3,779,778 and EP 126,712.

Preferably, no benzene ring structure is contained in the acids generated from the sulfonic acid generators (B1) and (B2). When a benzene ring is contained, there would occur the problem of a sensitivity lowering due to light absorption. The degree of the problem depends on an exposure light source, and the problem of a serious sensitivity lowering is encountered when the exposure light source is ArF.

The sulfonic acid generators (B1) and (B2) will be described in greater detail below.

As preferred compounds among the sulfonic acid generators (B1), there can be mentioned compounds containing an anionic structure of the formula Ra—$CF_2$—$CF_2$—$SO_3$—.

In the formula, Ra represents a structure consisting of any one, or a combination of two or more members, selected from among an oxygen atom, a sulfur atom, a nitrogen atom, a carbon atom, a hydrogen atom and a fluorine atom. Ra is selected so that the acid strength (pKa) of the generated acid with the anionic structure is below −3.50 and so that the sum of constituent elements, excluding a hydrogen atom, of the generated acid is 20 or less. As examples thereof, there can be mentioned F, $CF_3$, $C_2F_5$, O—$CF_3$, O—$C_2F_5$, S—$CF_3$, S—$C_2F_5$, $CF_2$—$SO_3$—$CH_3$, $CF_2$—$SO_2$—N—$(CH_3)_2$ and the like.

In particular, as preferred compounds among the sulfonic acid generators (B1), there can be mentioned the compounds of the following general formulae (ZI) and (ZII).

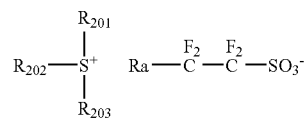

-continued

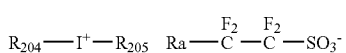

In the above general formula (ZI),

Ra is as defined above.

Each of $R_{201}$, $R_{202}$ and $R_{203}$ independently represents an organic group.

The number of carbon atoms of any of the organic groups represented by $R_{201}$, $R_{202}$ and $R_{203}$ is generally in the range of 1 to 30, preferably 1 to 20.

Two of $R_{201}$ to $R_{203}$ may be bonded with each other to thereby form a ring structure, and the ring within the same may contain an oxygen atom, a sulfur atom, an ester bond, an amido bond or a carbonyl group. As a group formed by bonding of two of $R_{201}$ to $R_{203}$, there can be mentioned an alkylene group (for example, a butylene group or a pentylene group).

As the organic groups represented by $R_{201}$, $R_{202}$ and $R_{203}$, there can be mentioned, for example, the corresponding groups of the following compounds (ZI-1), (ZI-2), (ZI-3) and (ZI-4).

The sulfonic acid generator (B1) may be a compound with two or more of the structures of the general formula (ZI). For example, use may be made of a compound having a structure wherein at least one of $R_{201}$ to $R_{203}$ of a compound of the general formula (ZI) is bonded with at least one of $R_{201}$ to $R_{203}$ of another compound of the general formula (ZI).

As preferred (ZI) components, there can be mentioned the following compounds (ZI-1), (ZI-2), (ZI-3) and (ZI-4).

The compounds (ZI-1) are arylsulfonium compounds of the general formula (ZI) wherein at least one of $R_{201}$ to $R_{203}$ is an aryl group, namely, compounds containing an arylsulfonium as a cation.

In the arylsulfonium compounds, all of the $R_{201}$ to $R_{203}$ may be aryl groups. Alternatively, the $R_{201}$ to $R_{203}$ may be an aryl group in part and an alkyl group or a cycloalkyl group in the remainder.

As the arylsulfonium compounds, there can be mentioned, for example, a triarylsulfonium compound, a diarylalkylsulfonium compound, an aryldialkylsulfonium compound, a diarylcycloalkylsulfonium compound and an aryldicycloalkylsulfonium compound.

The aryl group of the arylsulfonium compounds is preferably a phenyl group or a naphthyl group, more preferably a phenyl group. The aryl group may be one having a heterocyclic structure containing an oxygen atom, a nitrogen atom, a sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like. When the arylsulfonium compound has two or more aryl groups, the two or more aryl groups may be identical to or different from each other.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

The aryl group, alkyl group or cycloalkyl group represented by $R_{201}$ to $R_{203}$ may have as its substituent an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group or a phenylthio group. Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 4 carbon atoms and an alkoxy group having 1 to 4 carbon atoms. The substituents may be contained in any one of the three $R_{201}$ to $R_{203}$, or alternatively may be contained in all three of $R_{201}$ to $R_{203}$. When $R_{201}$ to $R_{203}$ represent an aryl group, the substituent preferably lies at the p-position of the aryl group.

Now, the compounds (ZI-2) will be described.

The compounds (ZI-2) are compounds of the formula (ZI) wherein each of $R_{201}$ to $R_{203}$ independently represents an organic group having no aromatic ring. The aromatic rings include an aromatic ring having a heteroatom.

The organic group having no aromatic ring represented by $R_{201}$ to $R_{203}$ generally has 1 to 30 carbon atoms, preferably 1 to 20 carbon atoms.

Preferably, each of $R_{201}$ to $R_{203}$ independently represents an alkyl group, a cycloalkyl group, an allyl group or a vinyl group. More preferred groups are a linear or branched 2-oxoalkyl group, a 2-oxocycloalkyl group and an alkoxycarbonylmethyl group. Especially preferred is a linear or branched 2-oxoalkyl group.

As preferred alkyl groups and cycloalkyl groups represented by $R_{201}$ to $R_{203}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group). As more preferred alkyl groups, there can be mentioned a 2-oxoalkyl group and an alkoxycarbonylmethyl group. As more preferred cycloalkyl group, there can be mentioned a 2-oxocycloalkyl group.

The 2-oxoalkyl group may be linear or branched. A group having >C=O at the 2-position of the alkyl group is preferred.

The 2-oxocycloalkyl group is preferably a group having >C=O at the 2-position of the cycloalkyl group.

As preferred alkoxy groups of the alkoxycarbonylmethyl group, there can be mentioned alkoxy groups having 1 to 5 carbon atoms (a methoxy group, an ethoxy group, a propoxy group, a butoxy group and a pentoxy group).

The $R_{201}$ to $R_{203}$ may be further substituted with a halogen atom, an alkoxy group (for example, 1 to 5 carbon atoms), a hydroxyl group, a cyano group or a nitro group.

The compounds (ZI-3) are compounds having a phenacylsulfonium salt structure. As such, there can be mentioned, for example, the compounds represented by the general formula (ZI) whose cations are those in the after-mentioned general formulae ($Z_{SC1}$-3) and ($Z_{SC1}$-3').

The compounds (ZI-4) are those of general formula (ZI-4) below.

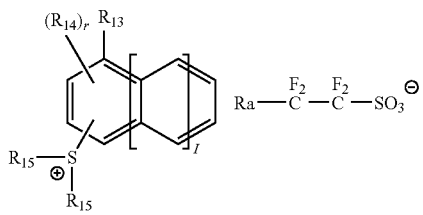

(ZI-4)

In the general formula (ZI-4), $R_{13}$ represents a hydrogen atom, a fluorine atom, a hydroxyl group, an alkyl group, a cycloalkyl group, an alkoxy group or an alkoxycarbonyl group.

$R_{14}$, each independently in the presence of two or more groups, represents an alkyl group, a cycloalkyl group, an alkoxy group, an alkylsulfonyl group or a cycloalkylsulfonyl group.

Each of $R_{15}$s independently represents an alkyl group or a cycloalkyl group, provided that the two $R_{15}$s may be bonded to each other to thereby form a ring.

l is an integer of 0 to 2.

r is an integer of 0 to 10.

Ra has the same meaning as that of the general formula (ZI).

In the general formula (ZI-4), the alkyl groups represented by $R_{13}$, $R_{14}$ and $R_{15}$ may be linear or branched and preferably each have 1 to 10 carbon atoms. As such, there can be mentioned a methyl group, an ethyl group, an n-propyl group, an i-propyl group, an n-butyl group, a 2-methylpropyl group, a 1-methylpropyl group, a t-butyl group, an n-pentyl group, a neopentyl group, an n-hexyl group, an n-heptyl group, an n-octyl group, a 2-ethylhexyl group, an n-nonyl group, an n-decyl group and the like. Of these alkyl groups, a methyl group, an ethyl group, an n-butyl group, a t-butyl group and the like are preferred.

As the cycloalkyl groups represented by $R_{13}$, $R_{14}$ and $R_{15}$, there can be mentioned cyclopropyl, cyclobutyl, cyclopentyl, cyclohexyl, cycloheptyl, cyclooctyl, cyclododecanyl, cyclopentenyl, cyclohexenyl, cyclooctadienyl and the like. Cyclopropyl, cyclopentyl, cyclohexyl and cyclooctyl are especially preferred.

The alkoxy groups represented by $R_{13}$ and $R_{14}$ may be linear or branched and preferably each have 1 to 10 carbon atoms. As such, there can be mentioned, for example, a methoxy group, an ethoxy group, an n-propoxy group, an i-propoxy group, an n-butoxy group, a 2-methylpropoxy group, a 1-methylpropoxy group, a t-butoxy group, an n-pentyloxy group, a neopentyloxy group, an n-hexyloxy group, an n-heptyloxy group, an n-octyloxy group, a 2-ethylhexyloxy group, an n-nonyloxy group, an n-decyloxy group and the like. Of these alkoxy groups, a methoxy group, an ethoxy group, an n-propoxy group, an n-butoxy group and the like are preferred.

The alkoxycarbonyl group represented by $R_{13}$ may be linear or branched and preferably has 2 to 11 carbon atoms. As such, there can be mentioned, for example, a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, an n-pentyloxycarbonyl group, a neopentyloxycarbonyl group, an n-hexyloxycarbonyl group, an n-heptyloxycarbonyl group, an n-octyloxycarbonyl group, a 2-ethylhexyloxycarbonyl group, an n-nonyloxycarbonyl group, an n-decyloxycarbonyl group and the like. Of these alkoxycarbonyl groups, a methoxycarbonyl group, an ethoxycarbonyl group, an n-butoxycarbonyl group and the like are preferred.

The alkylsulfonyl and cycloalkylsulfonyl groups represented by $R_{14}$ may be linear, branched or cyclic and preferably each have 1 to 10 carbon atoms. As such, there can be mentioned, for example, a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, an n-decanesulfonyl group, a cyclopentanesulfonyl group, a cyclohexanesulfonyl group and the like. Of these alkylsulfonyl and cycloalkylsulfonyl groups, a methanesulfonyl group, an ethanesulfonyl group, an n-propanesulfonyl group, an n-butanesulfonyl group, a cyclopentanesulfonyl group, a cyclohexanesulfonyl group and the like are preferred.

In the formula, l is preferably 0 or 1, more preferably 1, and r is preferably 0 to 2.

Each of the $R_{13}$, $R_{14}$ and $R_{15}$ groups may have a substituent. As such a substituent, there can be mentioned, for example, a halogen atom (e.g., a fluorine atom), a hydroxyl group, a carboxyl group, a cyano group, a nitro group, an alkoxy group, an alkoxyalkyl group, an alkoxycarbonyl group, an alkoxycarbonyloxy group or the like.

As the alkoxy group, there can be mentioned, for example, a linear, branched or cyclic alkoxy group having 1 to 20 carbon atoms, such as a methoxy group, an ethoxy group, an n-propoxy group, an i-propoxy group, an n-butoxy group, a 2-methylpropoxy group, a 1-methylpropoxy group, a t-butoxy group, a cyclopentyloxy group or a cyclohexyloxy group.

As the alkoxyalkyl group, there can be mentioned, for example, a linear, branched or cyclic alkoxyalkyl group having 2 to 21 carbon atoms, such as a methoxymethyl group, an ethoxymethyl group, a 1-methoxyethyl group, a 2-methoxyethyl group, a 1-ethoxyethyl group or a 2-ethoxyethyl group.

As the alkoxycarbonyl group, there can be mentioned, for example, a linear, branched or cyclic alkoxycarbonyl group having 2 to 21 carbon atoms, such as a methoxycarbonyl group, an ethoxycarbonyl group, an n-propoxycarbonyl group, an i-propoxycarbonyl group, an n-butoxycarbonyl group, a 2-methylpropoxycarbonyl group, a 1-methylpropoxycarbonyl group, a t-butoxycarbonyl group, a cyclopentyloxycarbonyl group or a cyclohexyloxycarbonyl group.

As the alkoxycarbonyloxy group, there can be mentioned, for example, a linear, branched or cyclic alkoxycarbonyloxy group having 2 to 21 carbon atoms, such as a methoxycarbonyloxy group, an ethoxycarbonyloxy group, an n-propoxycarbonyloxy group, an i-propoxycarbonyloxy group, an n-butoxycarbonyloxy group, a t-butoxycarbonyloxy group, a cyclopentyloxycarbonyloxy group or a cyclohexyloxycarbonyloxy group.

The cyclic structure that may be formed by the bonding of the two $R_{15}$s to each other is preferably a 5- or 6-membered ring, especially a 5-membered ring (namely, a tetrahydrothiophene ring) formed by two bivalent $R_{15}$s in cooperation with the sulfur atom of the general formula (ZI-4). The bivalent $R_{15}$s may have substituents. As such substituents, there can be mentioned, for example, a hydroxyl group, a carboxyl group, a cyano group, a nitro group, an alkoxy group, an alkoxyalkyl group, an alkoxycarbonyl group, an alkoxycarbonyloxy group and the like as mentioned above. It is especially preferred for the $R_{15}$ of the general formula (ZI-4) to be a methyl group, an ethyl group, the above-mentioned bivalent group allowing two $R_{15}$s to be bonded to each other so as to form a tetrahydrothiophene ring structure in cooperation with the sulfur atom of the general formula (ZI-4), or the like.

As mentioned above, the alkyl group, cycloalkyl group, alkoxy group and alkoxycarbonyl group represented by $R_{13}$ as well as the alkyl group, cycloalkyl group, alkoxy group, alkylsulfonyl group and cycloalkylsulfonyl group represented by $R_{14}$ may have substituents. Preferred substituents are a hydroxyl group, an alkoxy group, an alkoxycarbonyl group and a halogen atom (especially, a fluorine atom).

Preferred specific examples of the cations of the compounds of the general formula (ZI-4) will be shown below.

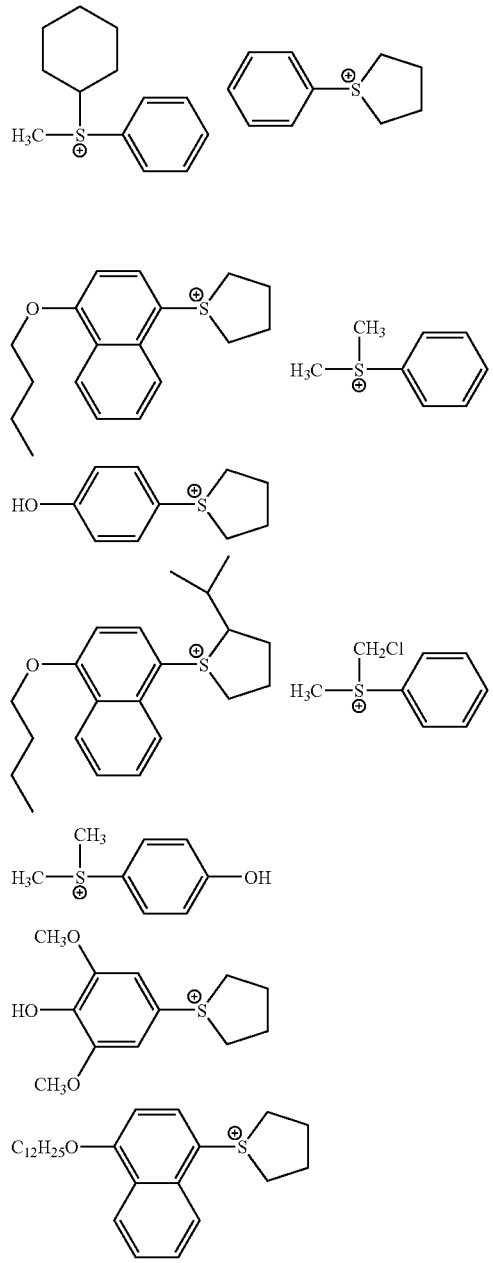
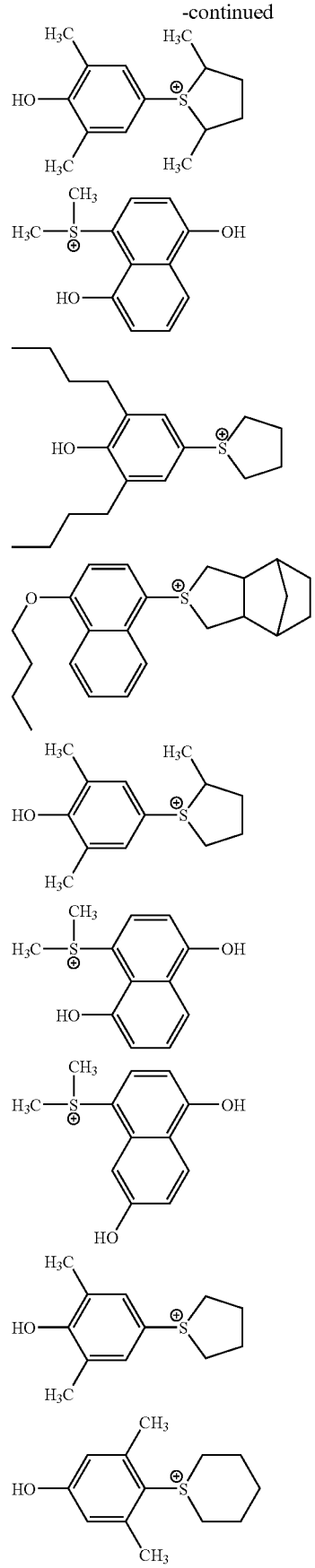

-continued

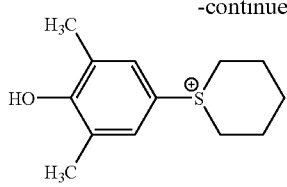

Now, the general formula (ZII) will be described.
In the general formula (ZII),
Ra is as defined above.
Each of $R_{204}$ and $R_{205}$ independently represents an aryl group, an alkyl group or a cycloalkyl group.

The aryl group represented by $R_{204}$ and $R_{205}$ is preferably a phenyl group or a naphthyl group, more preferably a phenyl group. The aryl group represented by $R_{204}$ and $R_{205}$ may be one having a heterocyclic structure containing an oxygen atom, a nitrogen atom, a sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like.

The alkyl group or cycloalkyl group represented by $R_{204}$ and $R_{205}$ is preferably a linear or branched alkyl group having 1 to 10 carbon atoms (for example, a methyl group, an ethyl group, a propyl group, a butyl group or a pentyl group) or a cycloalkyl group having 3 to 10 carbon atoms (a cyclopentyl group, a cyclohexyl group or a norbornyl group).

The aryl group, alkyl group or cycloalkyl group represented by $R_{204}$ and $R_{205}$ may have a substituent. As a possible substituent of the aryl group, alkyl group or cycloalkyl group represented by $R_{204}$ and $R_{205}$, there can be mentioned, for example, an alkyl group (for example, 1 to 15 carbon atoms), a cycloalkyl group (for example, 3 to 15 carbon atoms), an aryl group (for example, 6 to 15 carbon atoms), an alkoxy group (for example, 1 to 15 carbon atoms), a halogen atom, a hydroxyl group, a phenylthio group or the like.

The following compounds are specific examples of the sulfonic acid generators (B1).

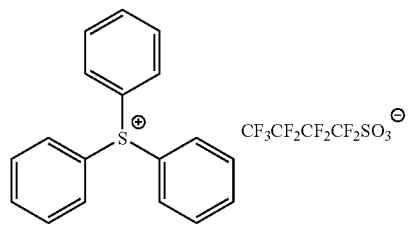

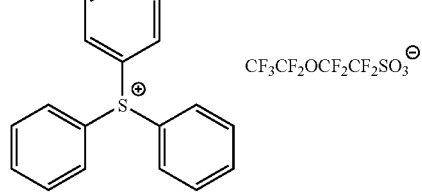

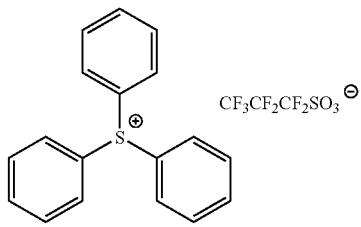

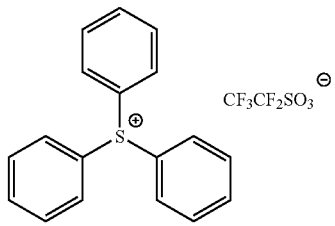

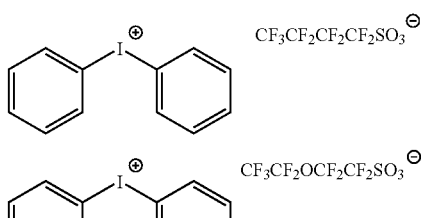

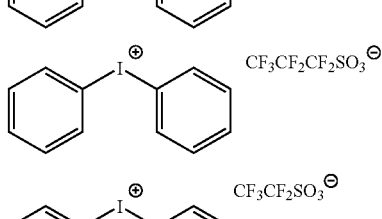

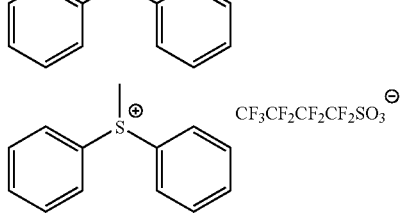

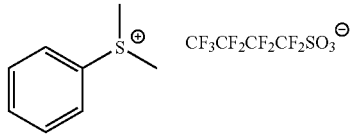

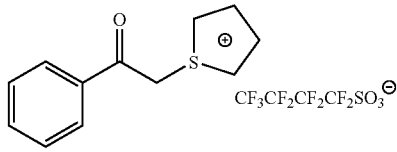

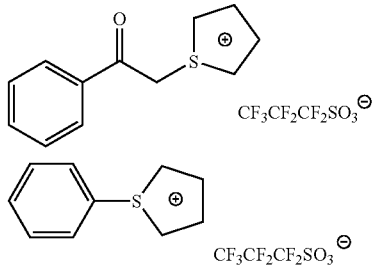

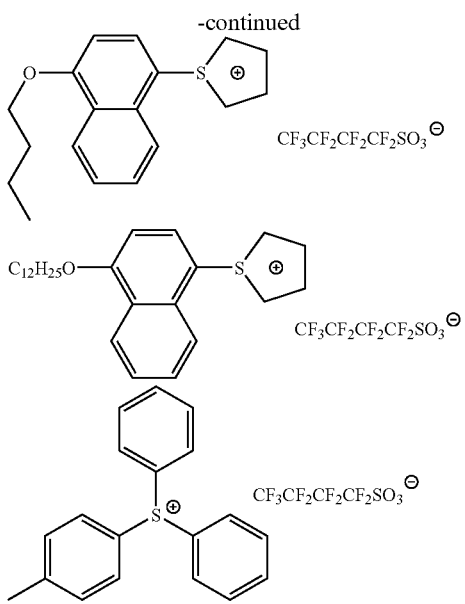

The sulfonic acid generator (B2) will be described in detail below.

As preferred compounds among the sulfonic acid generators (B2), there can be mentioned those containing an anionic structure of the formula $Rb-X-CF_2-SO_3^-$.

In the formula, X represents a structure selected from among $CH_2$, C=O, CRbH and $CRb_2$. Rb represents a structure consisting of any one, or a combination of two or more members, selected from among an oxygen atom, a sulfur atom, a nitrogen atom, a carbon atom and a hydrogen atom. Rb is selected so that the acid strength (pKa) of the generated acid with the anionic structure falls in the range of $-2.00 > pKa \geq -3.50$ and so that the sum of constituent elements, excluding a hydrogen atom, of the generated acid is 17 or more.

In particular, as preferred compounds among the sulfonic acid generators (B2), there can be mentioned those of the following general formula (I).

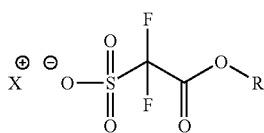
(I)

In the general formula (I), $X^+$ represents an organic counter ion, and R represents a hydrogen atom or an optionally substituted substituent having 1 or more carbon atoms.

R is preferably an organic group having 1 to 40 carbon atoms, more preferably an organic group having 3 to 40 carbon atoms and most preferably any of the organic groups of the following formula (II).

$$-(CH_2)_n-Rc-(Y)_m \qquad (II)$$

In the formula (II),

Rc represents a monocyclic or polycyclic organic group having 3 to 30 carbon atoms that may contain a cyclic ether, cyclic thioether, cyclic ketone, cyclic carbonate ester, lactone or lactam structure.

Y represents a hydroxyl group, a halogen atom, a cyano group, a carboxyl group, a hydrocarbon group having 1 to 10 carbon atoms, a hydroxyalkyl group having 1 to 10 carbon atoms, an alkoxy group having 1 to 10 carbon atoms, an acyl group having 1 to 10 carbon atoms, an alkoxycarbonyl group having 2 to 10 carbon atoms, an acyloxy group having 2 to 10 carbon atoms, an alkoxyalkyl group having 2 to 10 carbon atoms or a halogenated alkyl group having 1 to 8 carbon atoms.

In the formula, m is an integer of 0 to 6. In the event of multiple Ys, they may be identical to or different from each other.

Further, n is an integer of 0 to 10. The sum of carbon atoms constructing each of the groups R expressed by the formula (II) is 40 or less.

As preferred forms of the compounds of the general formula (I), there can be mentioned those of the general formulae ($Z_{SC1}$) and ($Z_{IC1}$).

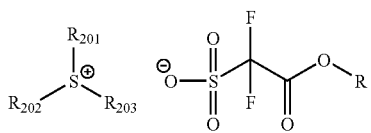
$Z_{SC1}$

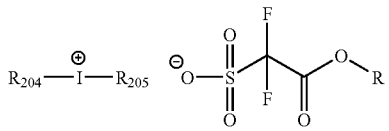
$Z_{IC1}$

In the general formula ($Z_{SC1}$),
the definition of R and preferred scope thereof are the same as in the general formula (I).

Each of $R_{201}$, $R_{202}$ and $R_{203}$ independently represents an organic group.

The number of carbon atoms of each of the organic groups represented by $R_{201}$, $R_{202}$ and $R_{203}$ is generally in the range of 1 to 30, preferably 1 to 20.

Two of $R_{201}$ to $R_{203}$ may be bonded with each other to thereby form a ring structure, and the ring within the same may contain an oxygen atom, a sulfur atom, an ester bond, an amido bond or a carbonyl group. As the group formed by bonding of two of $R_{201}$ to $R_{203}$, there can be mentioned an alkylene group (for example, a butylene group or a pentylene group).

As the organic groups represented by $R_{201}$, $R_{202}$ and $R_{203}$, there can be mentioned, for example, the corresponding groups of the following compounds ($Z_{SC1}$-1), ($Z_{SC1}$-2), ($Z_{SC1}$-3) and ($Z_{SC1}$-4).

The sulfonic acid generator (B2) may be a compound with two or more of the structures of the general formula ($Z_{SC1}$). For example, use may be made of a compound having a structure wherein at least one of $R_{201}$ to $R_{203}$ of a compound of the general formula ($Z_{SC1}$) is bonded with at least one of $R_{201}$ to $R_{203}$ of another compound of the general formula ($Z_{SC1}$).

As preferred ($Z_{SC1}$) components, there can be mentioned the following compounds ($Z_{SC1}$-1), ($Z_{SC1}$-2), ($Z_{SC1}$-3) and ($Z_{SC1}$-4).

The compounds ($Z_{SC1}$-1) are arylsulfonium compounds of the general formula ($Z_{SC1}$) wherein at least one of $R_{201}$ to $R_{203}$ is an aryl group, namely, compounds containing an arylsulfonium as a cation. The definition of R and preferred scope thereof are the same as in the general formula (I).

In the arylsulfonium compounds, all of the $R_{201}$ to $R_{203}$ may be aryl groups. It is also appropriate if the $R_{201}$ to $R_{203}$ are partially an aryl group and the remainder is an alkyl group or a cycloalkyl group.

As the arylsulfonium compounds, there can be mentioned, for example, a triarylsulfonium compound, a diarylalkylsulfonium compound, an aryldialkylsulfonium compound, a diarylcycloalkylsulfonium compound and an aryldicycloalkylsulfonium compound.

The aryl group of the arylsulfonium compounds is preferably a phenyl group or a naphthyl group, more preferably a phenyl group. The aryl group may be one having a heterocyclic structure containing an oxygen atom, a nitrogen atom, a sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like. When the arylsulfonium compound has two or more aryl groups, the two or more aryl groups may be identical to or different from each other.

The alkyl group or cycloalkyl group contained in the arylsulfonium compound according to necessity is preferably a linear or branched alkyl group having 1 to 15 carbon atoms or a cycloalkyl group having 3 to 15 carbon atoms. As such, there can be mentioned, for example, a methyl group, an ethyl group, a propyl group, an n-butyl group, a sec-butyl group, a t-butyl group, a cyclopropyl group, a cyclobutyl group, a cyclohexyl group or the like.

The aryl group, alkyl group or cycloalkyl group represented by $R_{201}$ to $R_{203}$ may have as its substituent an alkyl group (for example, 1 to 15 carbon atoms), a cycloalkyl group (for example, 3 to 15 carbon atoms), an aryl group (for example, 6 to 14 carbon atoms), an alkoxy group (for example, 1 to 15 carbon atoms), a halogen atom, a hydroxyl group or a phenylthio group. Preferred substituents are a linear or branched alkyl group having 1 to 12 carbon atoms, a cycloalkyl group having 3 to 12 carbon atoms and a linear, branched or cyclic alkoxy group having 1 to 12 carbon atoms. More preferred substituents are an alkyl group having 1 to 4 carbon atoms and an alkoxy group having 1 to 4 carbon atoms. The substituents may be contained in any one of the three $R_{201}$ to $R_{203}$, or alternatively may be contained in all three of $R_{201}$ to $R_{203}$. When $R_{201}$ to $R_{203}$ represent an aryl group, the substituent preferably lies at the p-position of the aryl group.

Now, the compounds ($Z_{SC1}$-2) will be described.

The compounds ($Z_{SC1}$-2) are compounds of the formula ($Z_{SC1}$) wherein each of $R_{201}$ to $R_{203}$ independently represents an organic group having no aromatic ring. The aromatic rings include an aromatic ring having a heteroatom. The definition of R and preferred scope thereof are the same as in the general formula (I).

The organic group having no aromatic ring represented by $R_{201}$ to $R_{203}$ generally has 1 to 30 carbon atoms, preferably 1 to 20 carbon atoms.

Preferably, each of $R_{201}$ to $R_{203}$ independently represents an alkyl group, a cycloalkyl group, an allyl group or a vinyl group. More preferred groups are a linear or branched 2-oxoalkyl group, a 2-oxocycloalkyl group and an alkoxycarbonylmethyl group. Especially preferred is a linear or branched 2-oxoalkyl group.

As preferred alkyl groups and cycloalkyl groups represented by $R_{201}$ to $R_{203}$, there can be mentioned a linear or branched alkyl group having 1 to 10 carbon atoms (for example, a methyl group, an ethyl group, a propyl group, a butyl group or a pentyl group) and a cycloalkyl group having 3 to 10 carbon atoms (a cyclopentyl group, a cyclohexyl group or a norbornyl group). As more preferred alkyl groups, there can be mentioned a 2-oxoalkyl group and an alkoxycarbonylmethyl group. As a more preferred cycloalkyl group, there can be mentioned a 2-oxocycloalkyl group.

The 2-oxoalkyl group may be linear or branched. A group having $>C=O$ at the 2-position of the alkyl group is preferred.

The 2-oxocycloalkyl group is preferably a group having $>C=O$ at the 2-position of the cycloalkyl group.

As preferred alkoxy groups of the alkoxycarbonylmethyl group, there can be mentioned alkoxy groups having 1 to 5 carbon atoms (a methoxy group, an ethoxy group, a propoxy group, a butoxy group and a pentoxy group).

The $R_{201}$ to $R_{203}$ may be further substituted with a halogen atom, an alkoxy group (for example, 1 to 5 carbon atoms), a hydroxyl group, a cyano group or a nitro group.

The compounds ($Z_{SC1}$-3) are those represented by the following general formulae ($Z_{SC1}$-3) and ($Z_{SC1}$-3') which have a phenacylsulfonium salt structure.

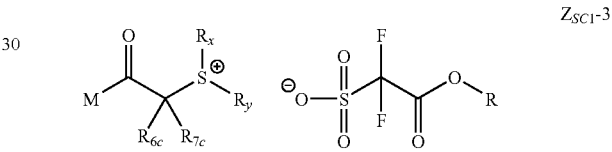

$Z_{SC1}$-3

In the general formula ($Z_{SC1}$-3),

M represents an alkyl group, a cycloalkyl group or an aryl group, provided that in the presence of a cyclic structure, that may contain a oxygen atom, a sulfur atom, an ester bond, an amide bond or a C—C double bond.

Each of $R_{6c}$ and $R_{7c}$ independently represents a hydrogen atom, an alkyl group or a cycloalkyl group.

Each of $R_x$ and $R_y$ independently represents an alkyl group, a 2-oxoalkyl group, an alkoxycarbonylmethyl group, a cycloalkyl group, a 2-oxocycloalkyl group, an allyl group or a vinyl group.

$R_x$ and $R_y$ may be bonded with each other to thereby form a cyclic structure.

Any two or more of M, $R_{6c}$ and $R_{7c}$ may be bonded with each other to thereby form a cyclic structure.

The definition of R and preferred scope thereof are the same as in the general formula (I).

The general formula ($Z_{SC1}$-3) will be described in detail below.

The alkyl group represented by M may be linear or branched. As such, there can be mentioned, for example, an alkyl group having 1 to 20 carbon atoms, preferably a linear or branched alkyl group having 1 to 12 carbon atoms (for example, a methyl group, an ethyl group, a linear or branched propyl group, a linear or branched butyl group or a linear or branched pentyl group).

The cycloalkyl group represented by M, there can be mentioned, for example, a cycloalkyl group having 3 to 8 carbon atoms (for example, a cyclopentyl group or a cyclohexyl group).

The aryl group represented by M preferably has 5 to 15 carbon atoms. As such, there can be mentioned, for example, a phenyl group, a naphthyl group or the like.

Each of the groups represented by M may have a substituent. As such a substituent, there can be mentioned, for example, an alkoxy group, a halogen atom or the like. Further, the cycloalkyl group and the aryl group represented by M may have an alkyl group or a cycloalkyl group as a substituent. The number of carbon atoms of a substituent is preferably 15 or less.

As the alkyl group represented by $R_{6c}$ and $R_{7c}$, there can be mentioned an alkyl group having 1 to 20 carbon atoms, preferably a linear or branched alkyl group having 1 to 12 carbon atoms (for example, a methyl group, an ethyl group, a linear or branched propyl group, a linear or branched butyl group or a linear or branched pentyl group).

As the cycloalkyl group represented by $R_{6c}$ and $R_{7c}$, there can be mentioned, for example, a cycloalkyl group having 3 to 8 carbon atoms (for example, a cyclopentyl group or a cyclohexyl group).

When M is a phenyl group, the phenyl group preferably has at least one linear, branched or cyclic alkyl group or linear, branched or cyclic alkoxy group as a substituent. More preferably, the sum of carbon atoms of the substituent is in the range of 2 to 15. Accordingly, there can be attained an enhancement of solvent solubility and inhibition of particle generation during storage.

The cyclic structure that may be formed by the bonding of two or more of M, $R_{6c}$ and $R_{7c}$ is preferably a 3- to 10-membered ring, especially 3- to 6-membered. The cyclic structure may have a carbon-carbon double bond.

As the alkyl groups and cycloalkyl groups represented by $R_x$ and $R_y$, there can be mentioned the same alkyl groups and cycloalkyl groups as mentioned with respect to $R_{6c}$ and $R_{7c}$.

As the 2-oxoalkyl group and 2-oxocycloalkyl group, there can be mentioned groups having >C=O at the 2-position of the alkyl group and cycloalkyl group represented by $R_{6c}$ and $R_{7c}$.

The preferred alkoxy groups of the alkoxycarbonylmethyl group may be linear, or branched, or cyclic. As such, there can be mentioned, for example, an alkoxy group having 1 to 10 carbon atoms, preferably a linear or branched alkoxy group having 1 to 5 carbon atoms (for example, a methoxy group, an ethoxy group, a linear or branched propoxy group, a linear or branched butoxy group or a linear or branched pentoxy group) and a cycloalkoxy group having 3 to 8 carbon atoms (for example, a cyclopentyloxy group or a cyclohexyloxy group).

As a group that may be formed by the bonding of $R_x$ and $R_y$, there can be mentioned a butylene group, a pentylene group or the like.

Each of $R_x$ and $R_y$ is preferably an alkyl group or a cycloalkyl group having 4 or more carbon atoms. The alkyl group or cycloalkyl group has more preferably 6 or more carbon atoms and still more preferably 8 or more carbon atoms.

In some aspects, the compounds represented by the general formula ($Z_{SC1}$-3) may be represented by the general formula ($Z_{SC1}$-3') below.

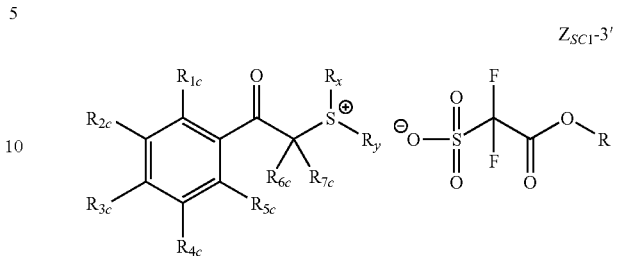

$Z_{SC1}$-3'

In the general formula ($Z_{SC1}$-3'),
the definition of R and preferred scope thereof are the same as in the general formula (I).
The definition of each of $R_x$, $R_y$, $R_{6c}$ and $R_{7c}$ and preferred scope thereof are the same as in the general formula ($Z_{SC1}$-3).

Each of $R_{1c}$ to $R_{5c}$ independently represents a hydrogen atom, an alkyl group, a cycloalkyl group, an alkoxy group or a halogen atom.

Any two or more of $R_{1c}$ to $R_{5c}$, and $R_{6c}$ and $R_{7c}$, and $R_x$ and $R_y$ may be bonded with each other to thereby form a ring structure. This ring structure may contain an oxygen atom, a sulfur atom, an ester bond or an amido bond. As the group formed by bonding of any two or more of $R_{1c}$ to $R_{5c}$, and $R_{6c}$ and $R_{7c}$, and $R_x$ and $R_y$, there can be mentioned a butylene group, a pentylene group or the like.

The alkyl group represented by $R_{1c}$ to $R_{5c}$ may be linear or branched. As such, there can be mentioned, for example, an alkyl group having 1 to 20 carbon atoms, preferably a linear or branched alkyl group having 1 to 12 carbon atoms (for example, a methyl group, an ethyl group, a linear or branched propyl group, a linear or branched butyl group or a linear or branched pentyl group). As the cycloalkyl group, there can be mentioned, for example, a cycloalkyl group having 3 to 8 carbon atoms (for example, a cyclopentyl group or a cyclohexyl group).

The alkoxy group represented by $R_{1c}$ to $R_{5c}$ may be linear, or branched, or cyclic. As such, there can be mentioned, for example, an alkoxy group having 1 to 10 carbon atoms, preferably a linear or branched alkoxy group having 1 to 5 carbon atoms (for example, a methoxy group, an ethoxy group, a linear or branched propoxy group, a linear or branched butoxy group or a linear or branched pentoxy group) and a cycloalkoxy group having 3 to 8 carbon atoms (for example, a cyclopentyloxy group or a cyclohexyloxy group).

Preferably, any one of $R_{1c}$ to $R_{5c}$ is a linear or branched alkyl group, a cycloalkyl group or a linear, branched or cyclic alkoxy group. More preferably, the sum of carbon atoms of $R_{1c}$ to $R_{5c}$ is in the range of 2 to 15. Accordingly, there can be attained an enhancement of solvent solubility and inhibition of particle generation during storage.

The compounds ($Z_{SC1}$-4) are those of general formula ($Z_{SC1}$-4) below.

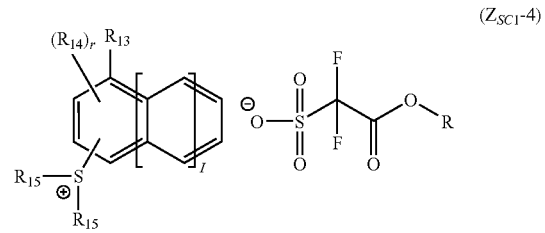

($Z_{SC1}$-4)

In the general formula ($Z_{SC1}$-4), the definition of R and preferred scope thereof are the same as in the general formula (I).

The definition of each of $R_{13}$, $R_{14}$ and $R_{15}$ and preferred scope thereof are the same as in the general formula (ZI-4).

The general formula ($Z_{IC1}$) will be described below.

In the general formula ($Z_{IC1}$), the definition of R and preferred scope thereof are the same as in the general formula (I).

Each of $R_{204}$ and $R_{205}$ independently represents an aryl group, an alkyl group or a cycloalkyl group.

The aryl group represented by $R_{204}$ and $R_{205}$ is preferably a phenyl group or a naphthyl group, more preferably a phenyl group. The aryl group represented by $R_{204}$ and $R_{205}$ may be one having a heterocyclic structure containing an oxygen atom, a nitrogen atom, a sulfur atom or the like. As the aryl group having a heterocyclic structure, there can be mentioned, for example, a pyrrole residue (group formed by loss of one hydrogen atom from pyrrole), a furan residue (group formed by loss of one hydrogen atom from furan), a thiophene residue (group formed by loss of one hydrogen atom from thiophene), an indole residue (group formed by loss of one hydrogen atom from indole), a benzofuran residue (group formed by loss of one hydrogen atom from benzofuran), a benzothiophene residue (group formed by loss of one hydrogen atom from benzothiophene) or the like.

The alkyl group or cycloalkyl group represented by $R_{204}$ and $R_{205}$ is preferably a linear or branched alkyl group having 1 to 10 carbon atoms (for example, a methyl group, an ethyl group, a propyl group, a butyl group or a pentyl group) or a cycloalkyl group having 3 to 10 carbon atoms (a cyclopentyl group, a cyclohexyl group or a norbornyl group).

The aryl group, alkyl group or cycloalkyl group represented by $R_{204}$ and $R_{205}$ may have a substituent. As the substituent optionally contained in the aryl group, alkyl group or cycloalkyl group represented by $R_{204}$ and $R_{205}$, there can be mentioned, for example, an alkyl group (for example, 1 to 15 carbon atoms), a cycloalkyl group (for example, 3 to 15 carbon atoms), an aryl group (for example, 6 to 15 carbon atoms), an alkoxy group (for example, 1 to 15 carbon atoms), a halogen atom, a hydroxyl group, a phenylthio group or the like.

Specific examples of the compounds of the general formula (I) are shown below.

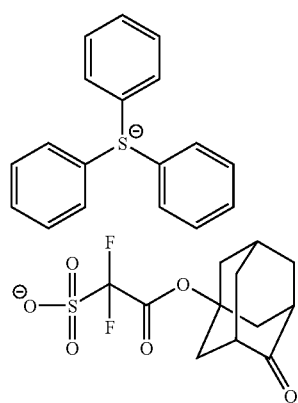

-continued

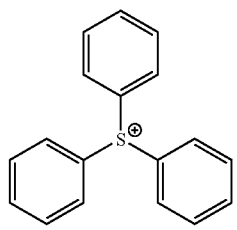

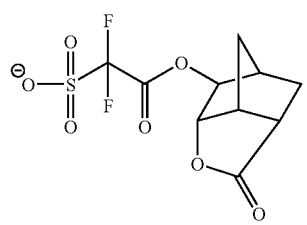

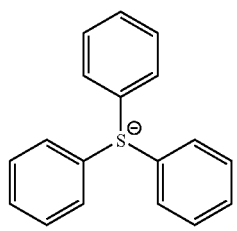

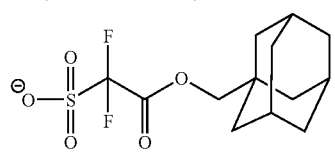

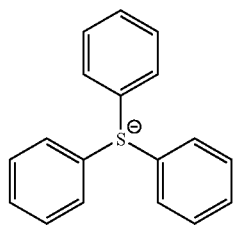

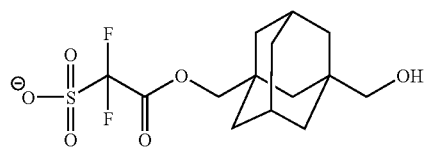

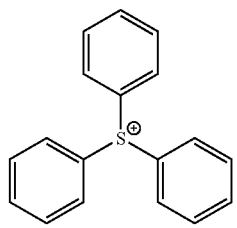

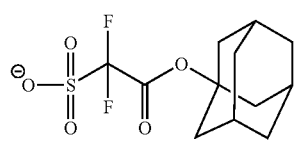

21
-continued
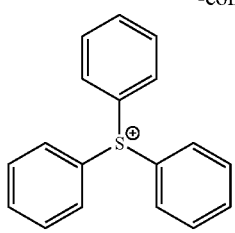
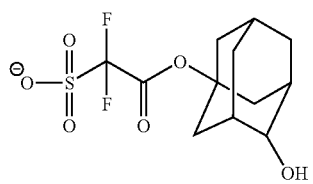
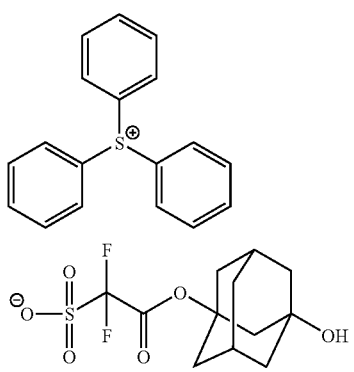
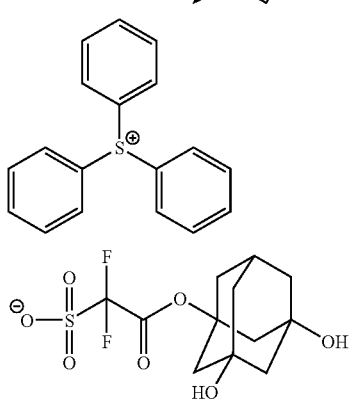
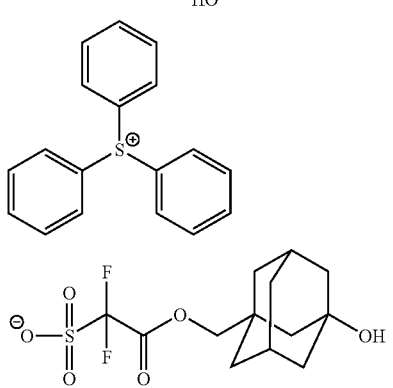
22
-continued
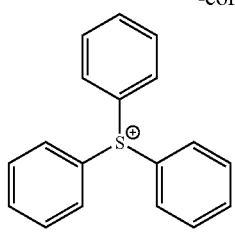
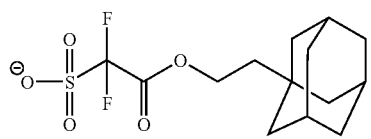
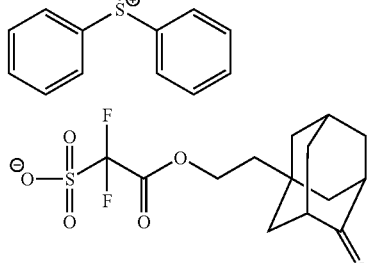
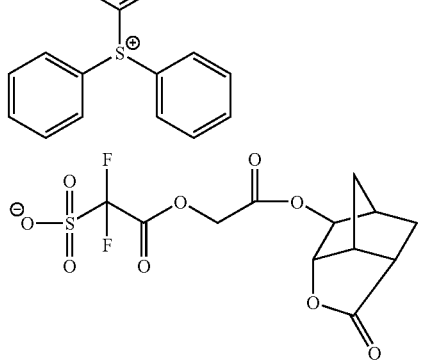
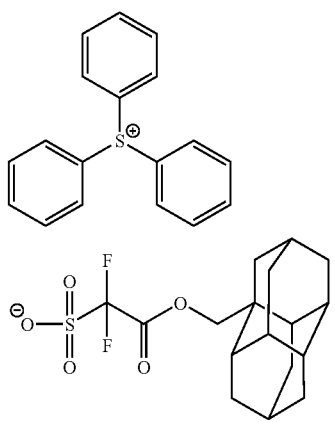

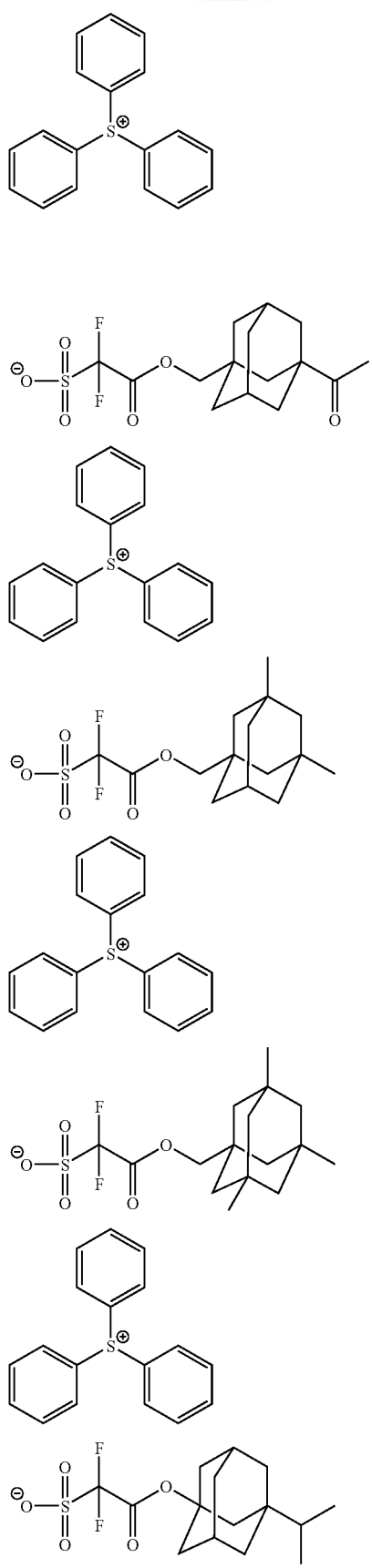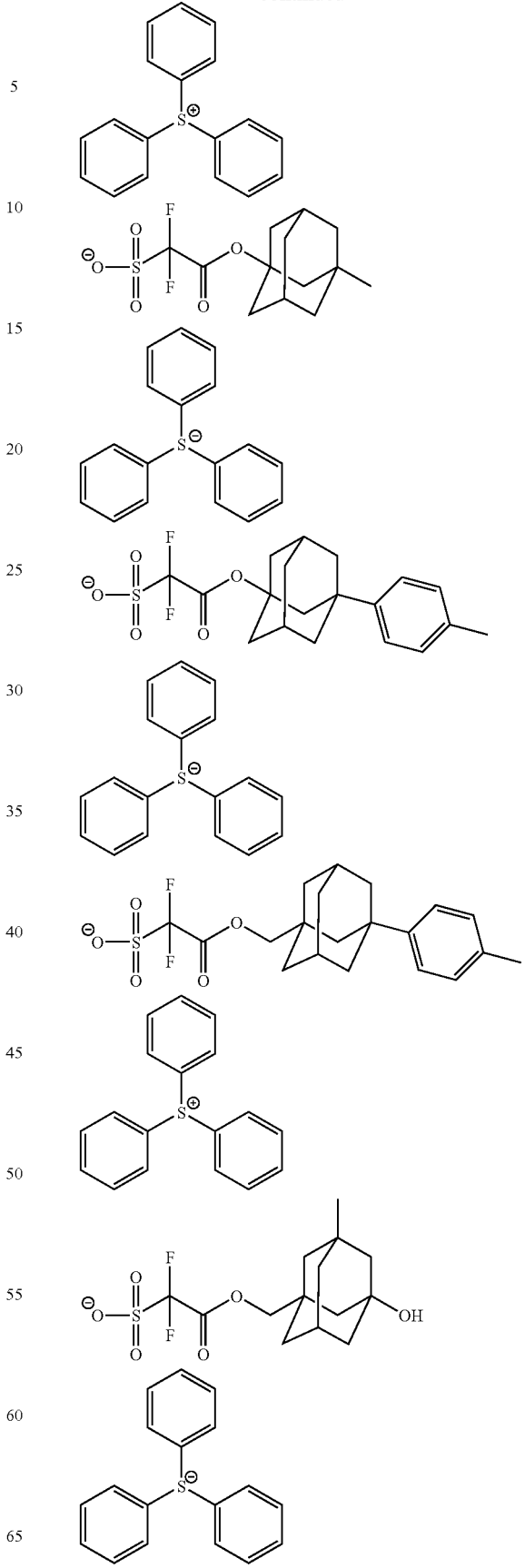

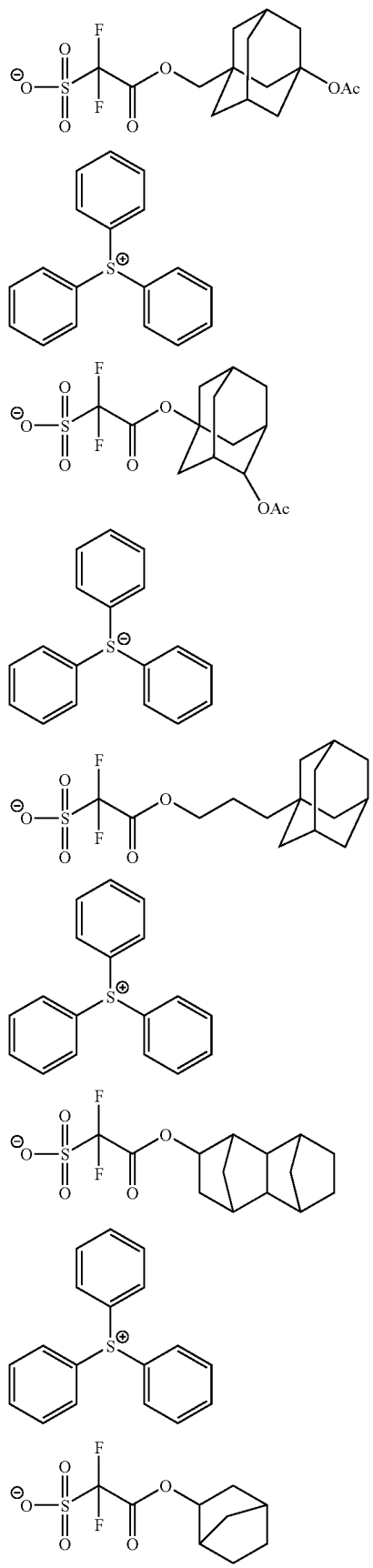
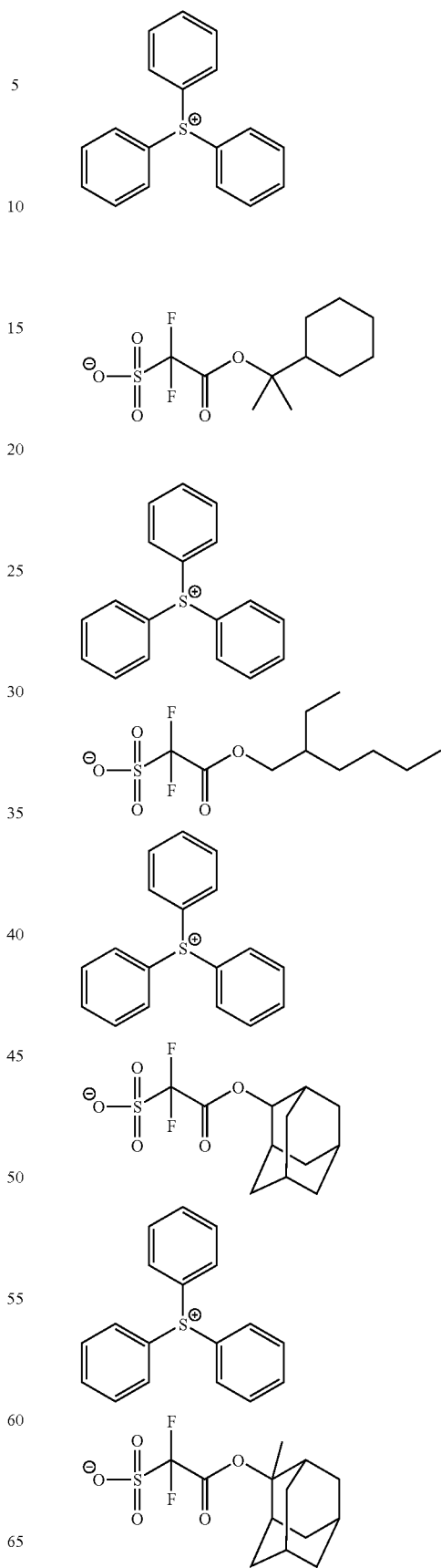

27
-continued
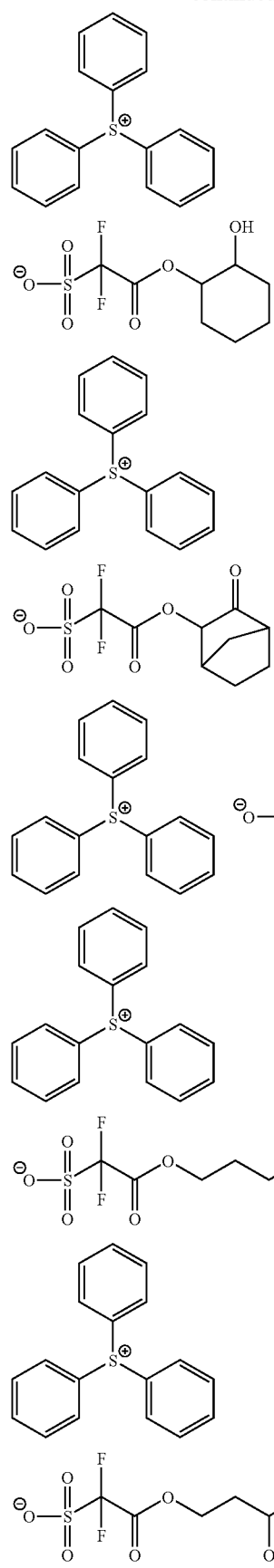
28
-continued
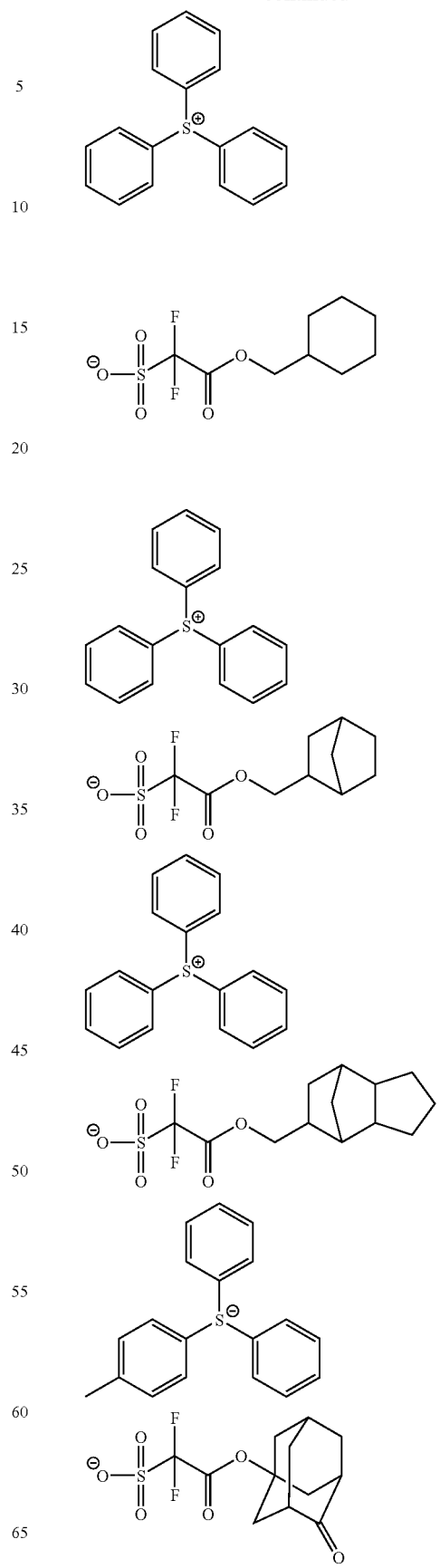

29
-continued
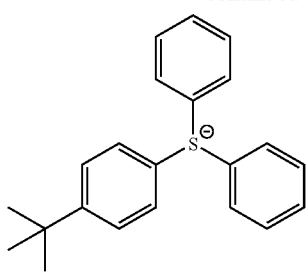
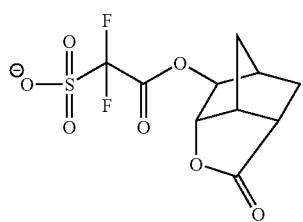
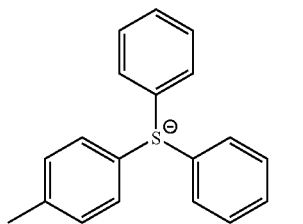
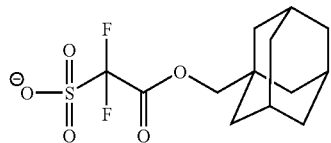
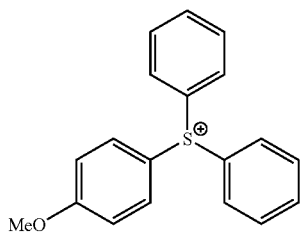
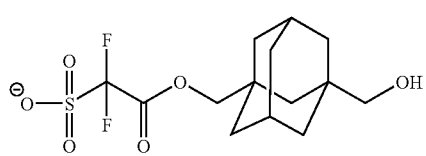
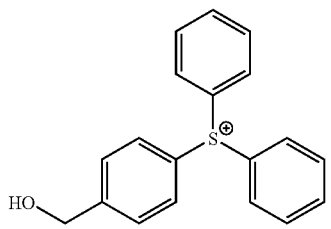
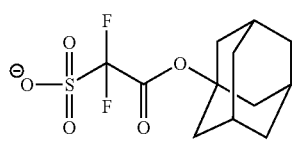
30
-continued
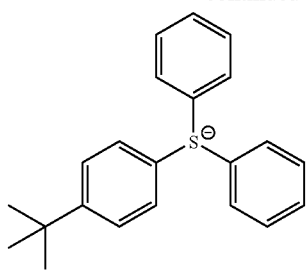
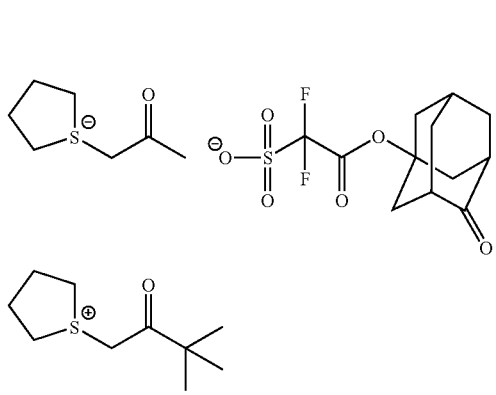
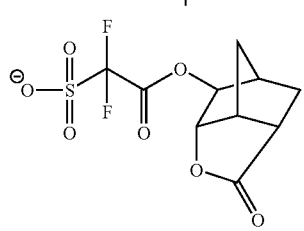
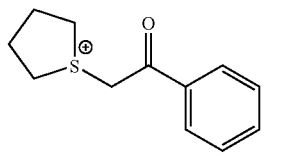
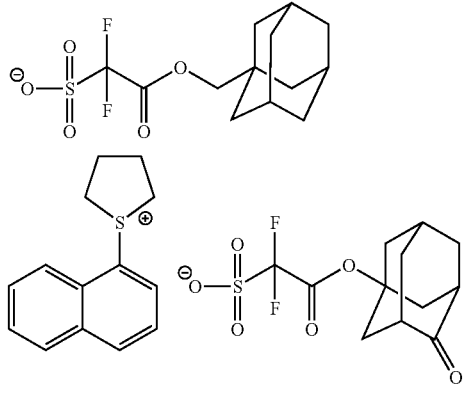

31
-continued
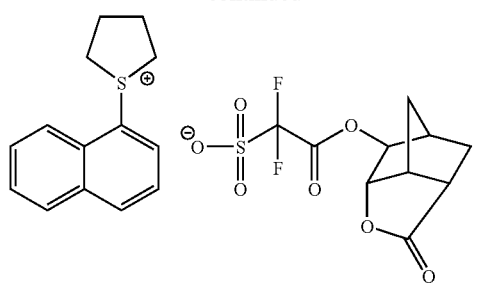
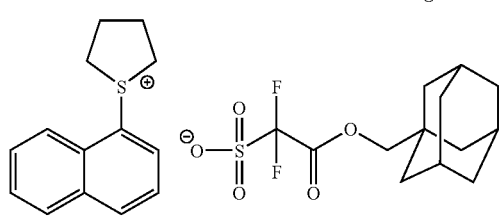
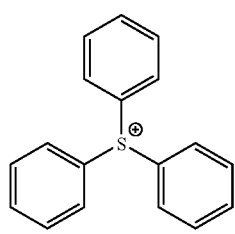
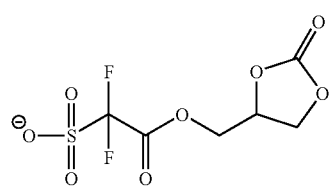
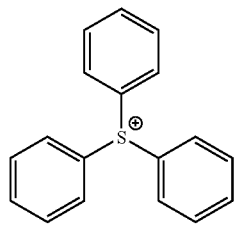
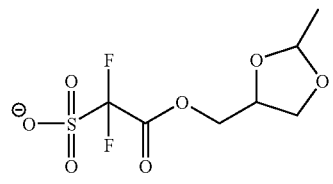
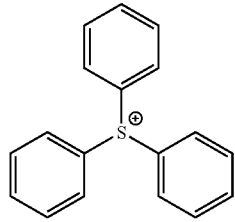
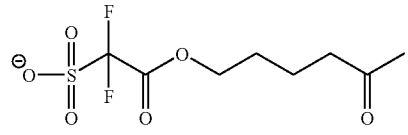
32
-continued
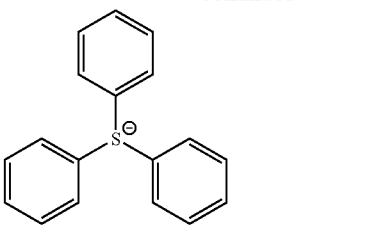
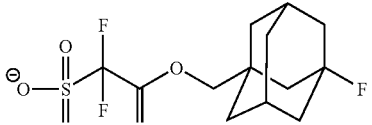
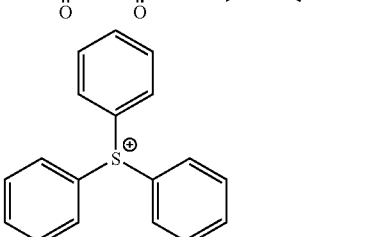
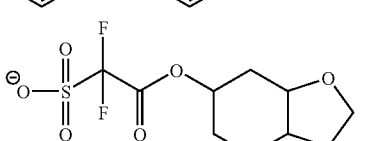
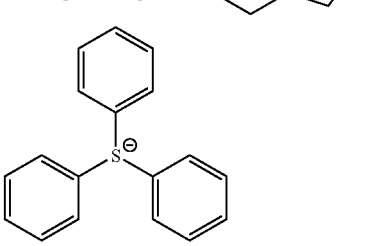
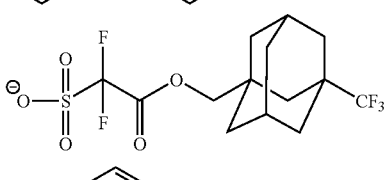
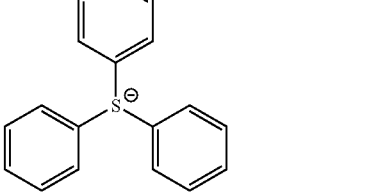
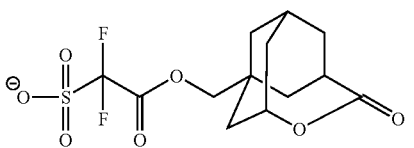
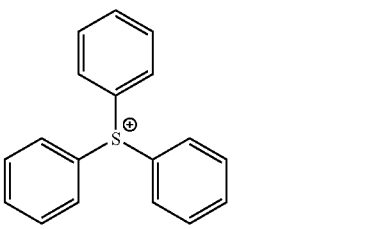

-continued

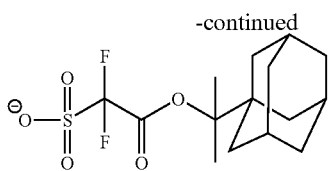

Further, as preferred sulfonic acid generators (B2), there can be mentioned the compounds of the following general formula (1).

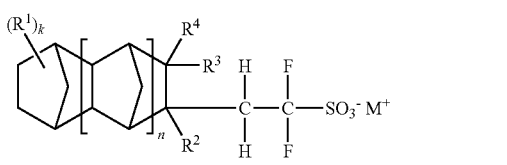

In the formula (1), $R^1$ represents $-R^5$, $-COR^6$, $-COOR^6$, $-CON(R^6)(R^7)$, $-N(R^6)(R^7)$, $-N(R^6)CO(R^7)$, $-N(R^6)COOR^7$, $-N(COR^6)(COR^7)$, $-SR^6$, $-SOR^6$, $-SO_2R^6$ or $-SO_2(OR^6)$. In the presence of a plurality of $R^1$s, they may be identical to or different from each other. When the $R^1$s are contained in a norbornane structure, they may form a ring in cooperation with carbon atom(s) of the structure. In the presence of a plurality of $R^1$s, any two or more thereof may be bonded with each other to thereby form a ring. $R^5$ represents an optionally substituted linear, branched or cyclic monovalent hydrocarbon group having 1 to 30 carbon atoms, an optionally substituted aryl group having 6 to 30 carbon atoms, or an optionally substituted monovalent heterocyclic organic group having 4 to 30 atoms. Each of $R^6$ and $R^7$ independently represents a hydrogen atom, an optionally substituted linear, branched or cyclic monovalent hydrocarbon group having 1 to 30 carbon atoms, an optionally substituted aryl group having 6 to 30 carbon atoms, or an optionally substituted monovalent heterocyclic organic group having 4 to 30 atoms. Each of $R^2$, $R^3$ and $R^4$ independently represents a hydrogen atom or a linear, branched or cyclic alkyl group having 1 to 30 carbon atoms. In the formula, k is an integer of 0 or greater, and n is an integer of 0 to 5. $M^+$ represents a monovalent onium cation.

The amount of sulfonic acid generators (B) contained is preferably in the range of 0.1 to 35 mass %, more preferably 0.2 to 25 mass %, based on the total solid content of the actinic ray-sensitive or radiation-sensitive resin composition of the present invention.

The amount of sulfonic acid generator (B1) plus sulfonic acid generator (B2) contained is preferably in the range of 0.1 to 30 mass % based on the total solid content of the actinic ray-sensitive or radiation-sensitive resin composition of the present invention.

The mixing ratio thereof is preferably in the range of 5 to 95 mol %, more preferably 10 to 90 mol %.

2. Resin Whose Solubility in an Alkali Developer is Increased by the Action of an Acid (Resin (A))

The resin (A) is a resin whose solubility in an alkali developer is increased by the action of an acid, especially a resin provided at its principal chain or side chain or both thereof with a group that is decomposed by the action of an acid to thereby generate an alkali soluble group (hereinafter also referred to as an "acid-decomposable group").

As the alkali soluble group, there can be mentioned a phenolic hydroxyl group, a carboxyl group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred alkali soluble groups, there can be mentioned a carboxyl group, a fluoroalcohol group (preferably hexafluoroisopropanol) and a sulfonate group.

The acid-decomposable group is preferably a group as obtained by substituting the hydrogen atom of any of these alkali soluble groups with an acid eliminable group.

As the acid eliminable group, there can be mentioned, for example, $-C(R_{36})(R_{37})(R_{38})$, $-C(R_{36})(R_{37})(OR_{39})$, $-C(R_{01})(R_{02})(OR_{39})$ or the like.

In the formulae, each of $R_{36}$ to $R_{39}$ independently represents an alkyl group, a cycloalkyl group, an aryl group, an aralkyl group or an alkenyl group. $R_{36}$ and $R_{37}$ may be bonded with each other to thereby form a ring structure.

Each of $R_{01}$ to $R_{02}$ independently represents a hydrogen atom, an alkyl group, a cycloalkyl group, an aryl group, an aralkyl group or an alkenyl group.

Preferably, the acid-decomposable group is a cumyl ester group, an enol ester group, an acetal ester group, a tertiary alkyl ester group or the like. A tertiary alkyl ester group is more preferred.

The repeating unit having an acid-decomposable group that may be contained in the resin (A) is preferably any of those of the following general formula (AI).

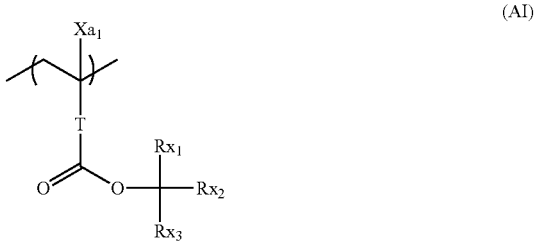

In the general formula (AI), $Xa_1$ represents a hydrogen atom, a methyl group, a trifluoromethyl group or a hydroxymethyl group, T represents a single bond or a bivalent connecting group, and each of $Rx_1$ to $Rx_3$ independently represents an alkyl group (linear or branched) or a cycloalkyl group (monocyclic or polycyclic), provided that at least two of $Rx_1$ to $Rx_3$ may be bonded with each other to thereby form a cycloalkyl group (monocyclic or polycyclic).

As the bivalent connecting group represented by T, there can be mentioned an alkylene group, a group of the formula $-COO\text{-Rt-}$, a group of the formula $-O\text{-Rt-}$ or the like. In the formulae, Rt represents an alkylene group or a cycloalkylene group.

T is preferably a single bond or a group of the formula $-COO\text{-Rt-}$. Rt is preferably an alkylene group having 1 to 5 carbon atoms, more preferably a $-CH_2-$ group or $-(CH_2)_3-$ group.

The alkyl group represented by each of $Rx_1$ to $Rx_3$ is preferably one having 1 to 4 carbon atoms, such as a methyl group, an ethyl group, an n-propyl group, an isopropyl group, an n-butyl group, an isobutyl group or a t-butyl group.

The cycloalkyl group represented by each of $Rx_1$ to $Rx_3$ is preferably a monocyclic alkyl group, such as a cyclopentyl group or a cyclohexyl group, or a polycyclic alkyl group, such as a norbornyl group, a tetracyclodecanyl group, a tetracyclododecanyl group or an adamantyl group.

The cycloalkyl group formed by bonding of at least two of $Rx_1$ to $Rx_3$ is preferably a monocyclic alkyl group, such as a cyclopentyl group or a cyclohexyl group, or a polycyclic alkyl group, such as a norbornyl group, a tetracyclodecanyl group, a tetracyclododecanyl group or an adamantyl group, more preferably a monocyclic alkyl group having 5 to 6 carbon atoms.

In a preferred mode, $Rx_1$ is a methyl group or an ethyl group, and $Rx_2$ and $Rx_3$ are bonded with each other to thereby form any of the above-mentioned cycloalkyl groups.

The content of repeating units having an acid-decomposable group is preferably in the range of 20 to 70 mol %, more preferably 30 to 50 mol %, based on all the repeating units of the resin (A).

Specific examples of the preferred repeating units having acid-decomposable groups will be shown below, which however in no way limit the scope of the present invention.

In the following formulae, each of $R_x$ and $Xa_1$ represents a hydrogen atom, $CH_3$, $CF_3$ or $CH_2OH$. Each of Rxa and Rxb represents an alkyl group having 1 to 4 carbon atoms. Z, each independently in the presence of two or more groups, represents a substituent containing a polar group. As the substituent containing a polar group, there can be mentioned a linear or branched alkyl group or a cycloalkyl group each having a hydroxyl group, a cyano group, an amino group, an alkylamido group or a sulfonamido group. An alkyl group having a hydroxyl group is especially preferred. p represents 0 or a positive integer.

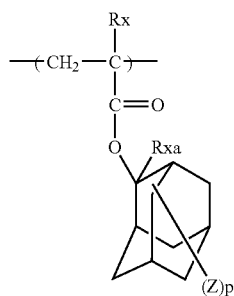

1

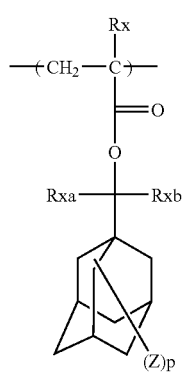

2

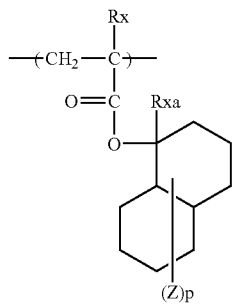

3

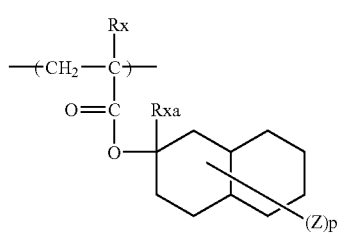

4

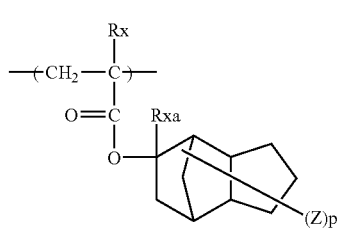

5

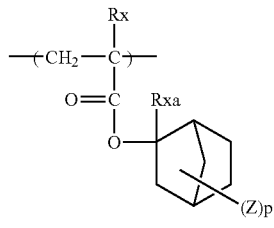

6

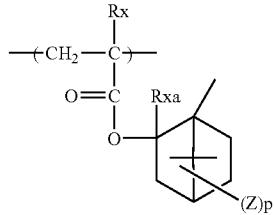

7

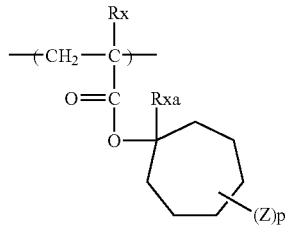

8

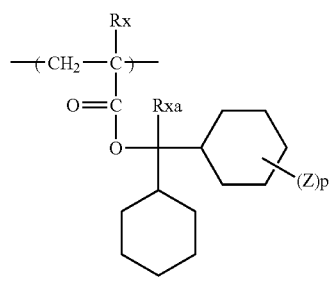
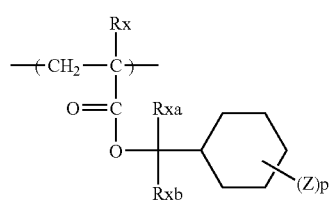
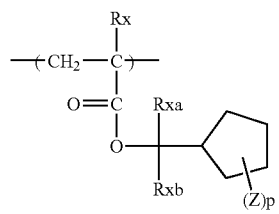
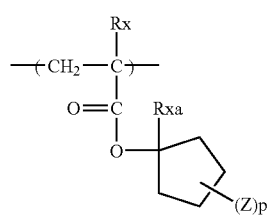
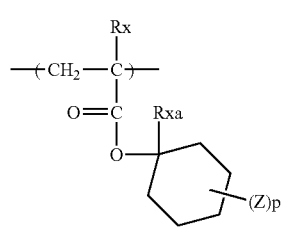
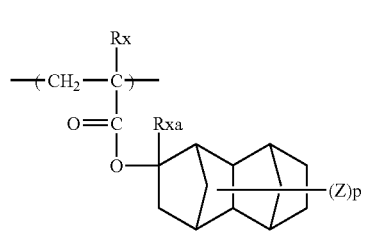
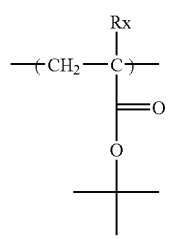
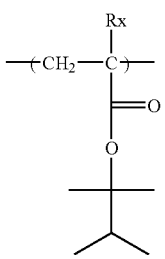
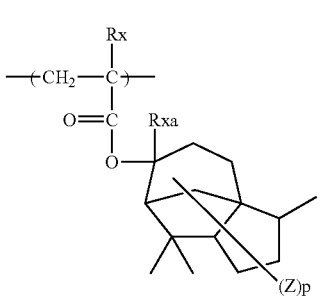
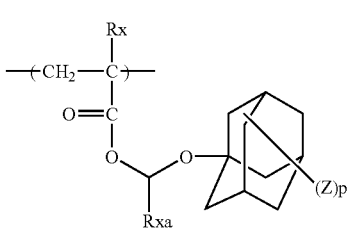
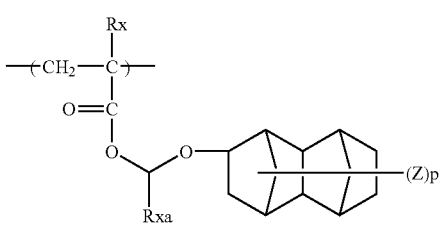
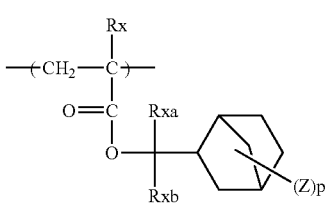
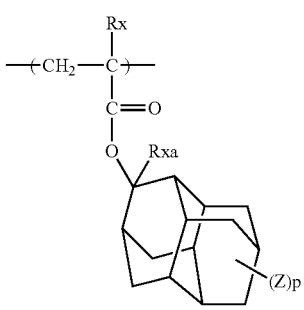

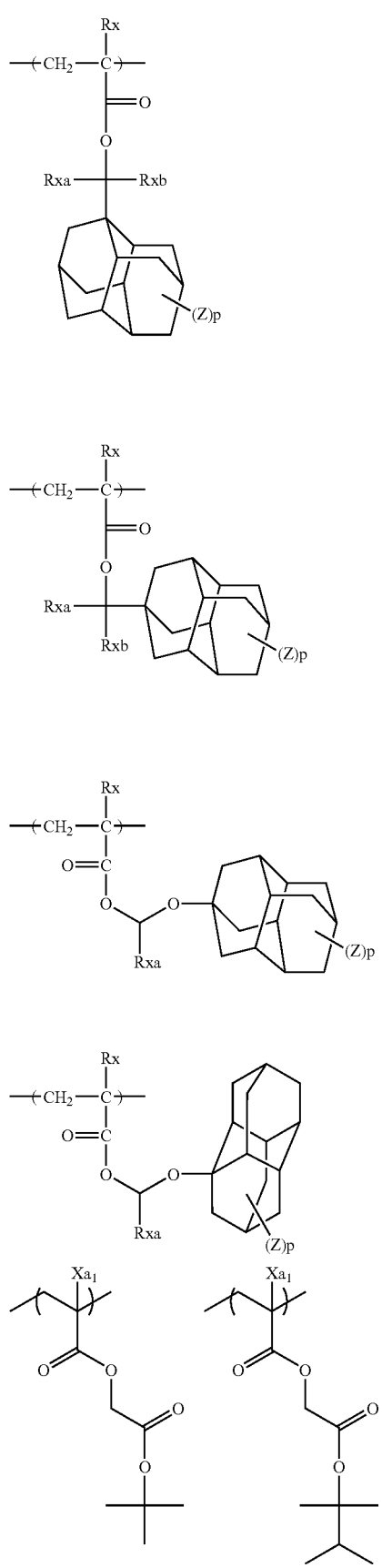
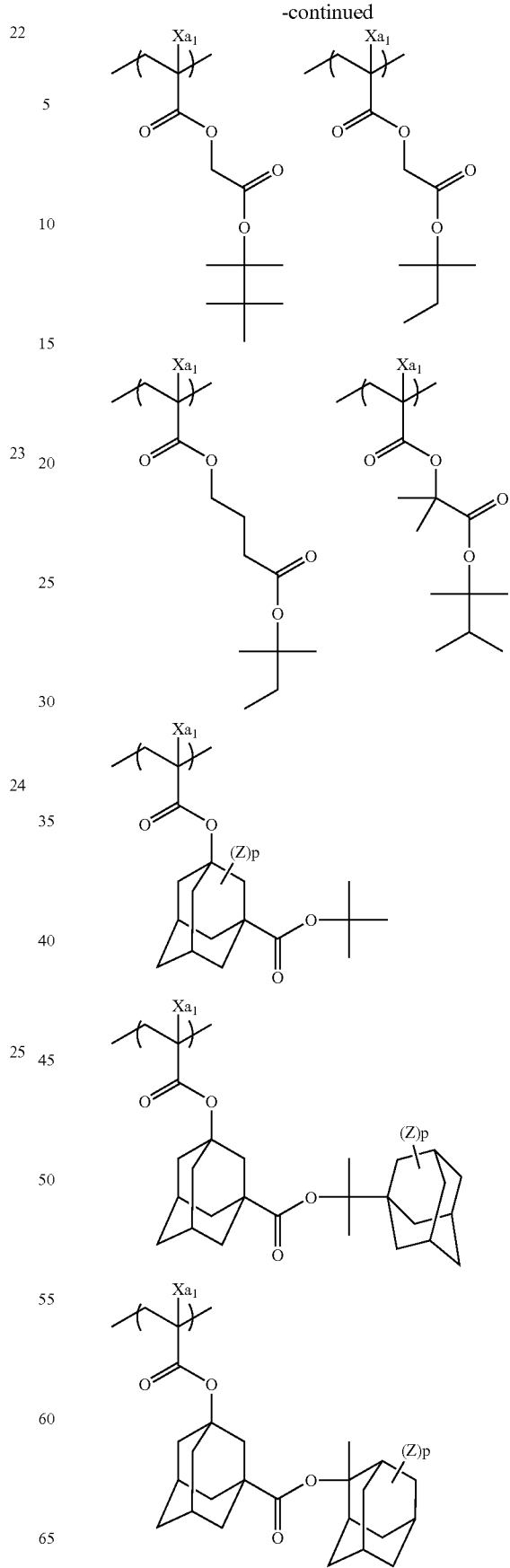

-continued
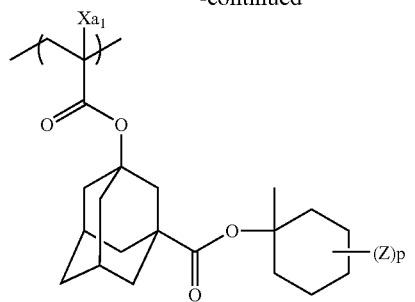
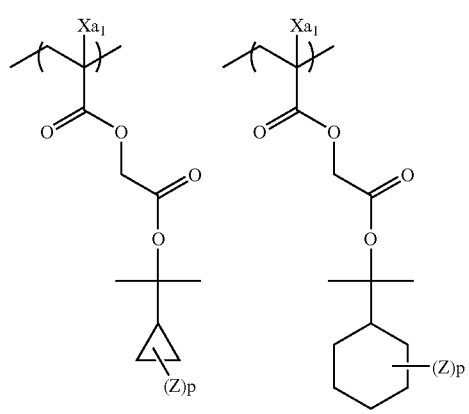
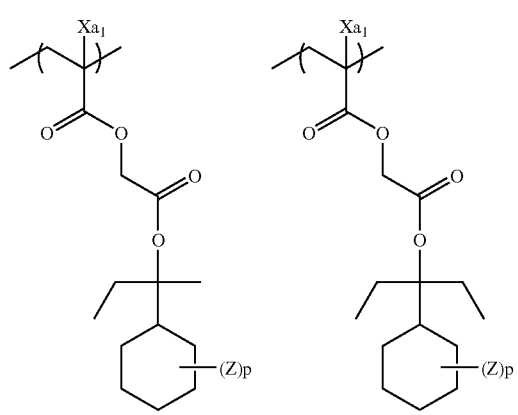
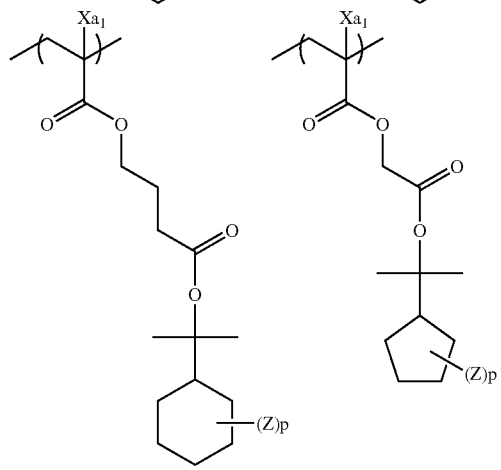
-continued
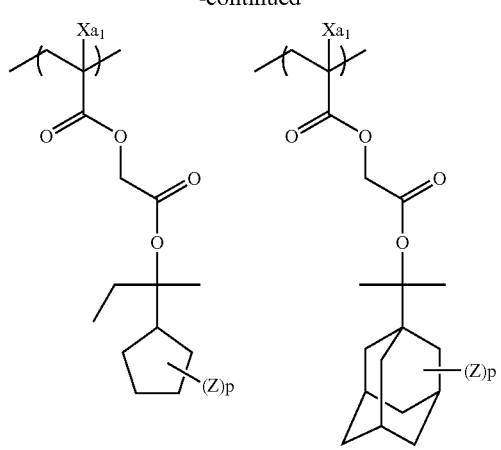
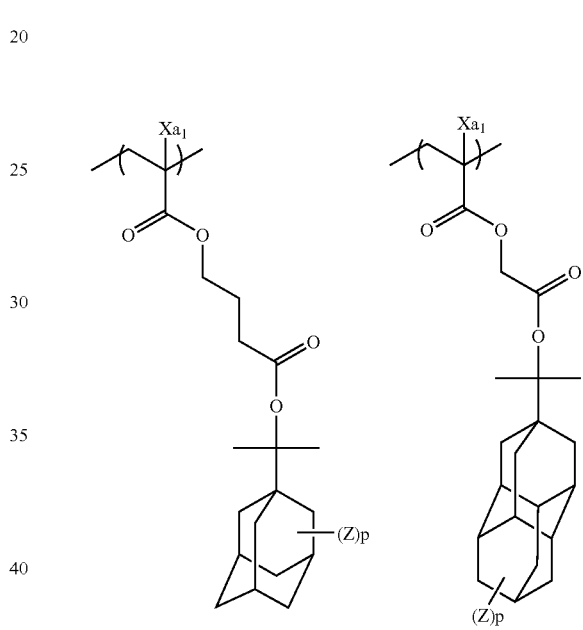
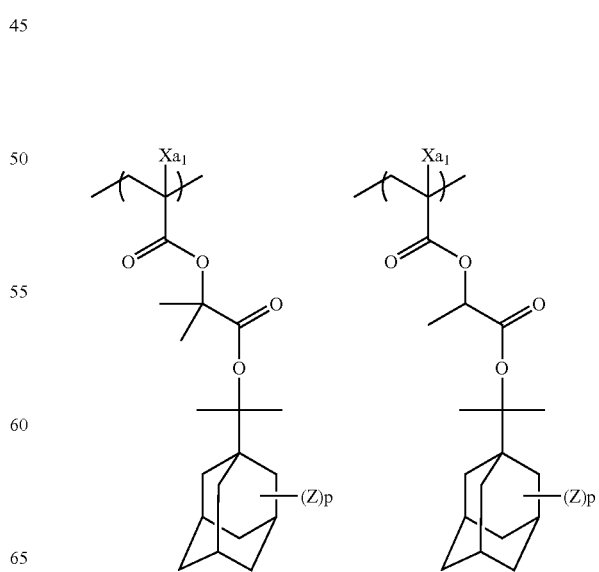

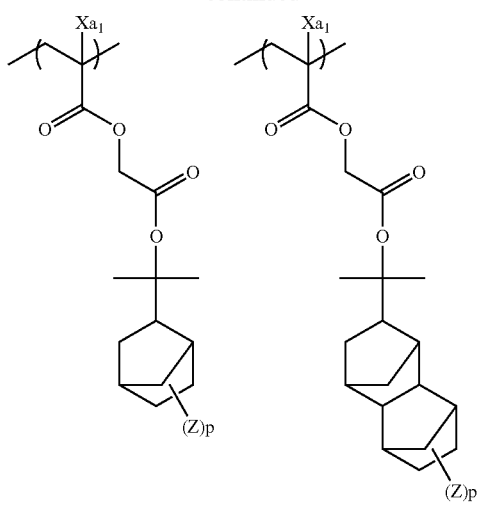
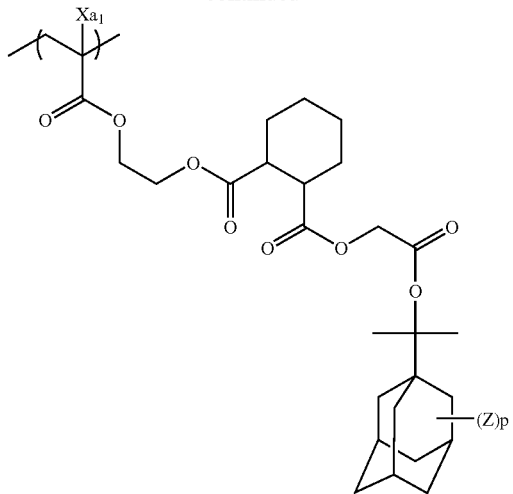
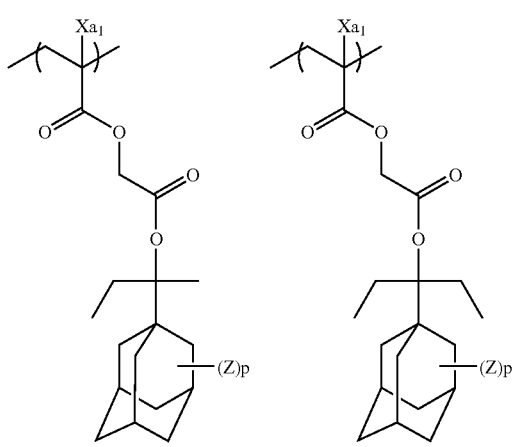
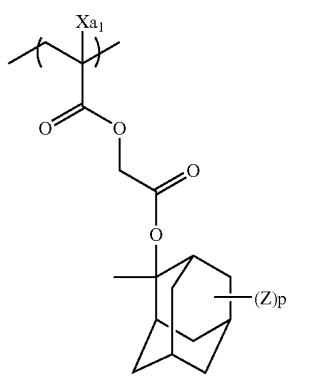
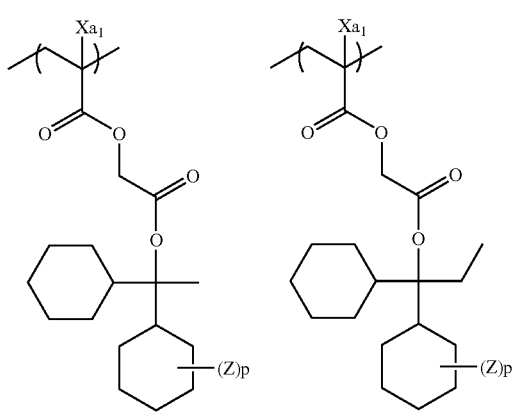
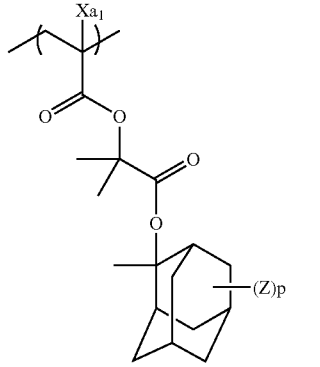

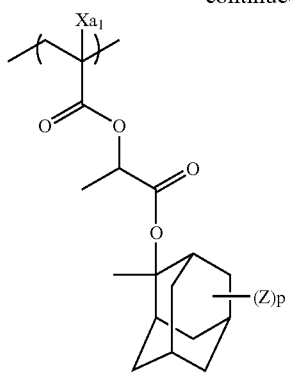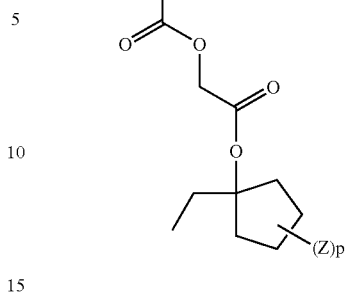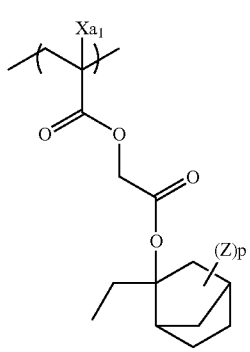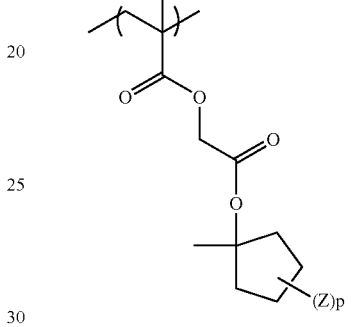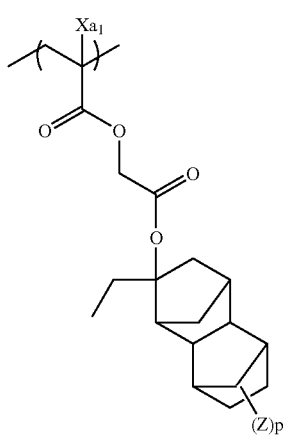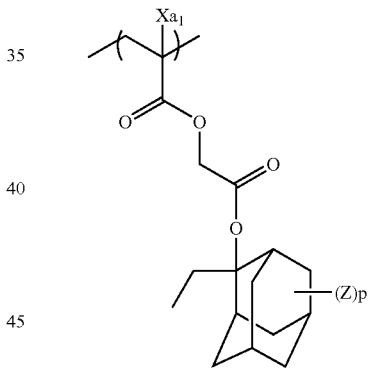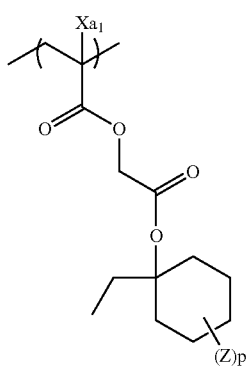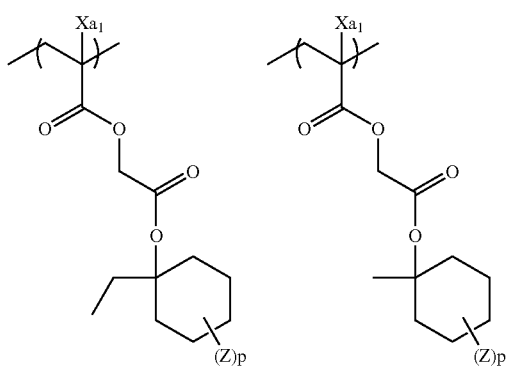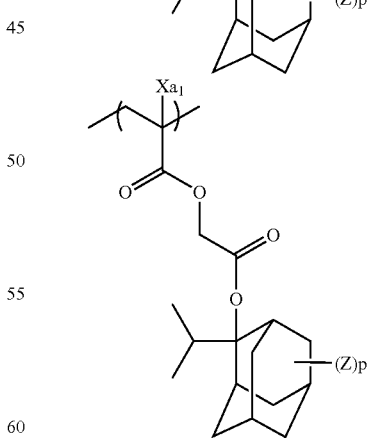
In the present invention, the acid-decomposable groups may be used in combination. Preferred combinations of repeating units having acid-decomposable groups will be shown below. In the following formulae, R represents a hydrogen atom, $CH_3$, $CF_3$ or $CH_2OH$.

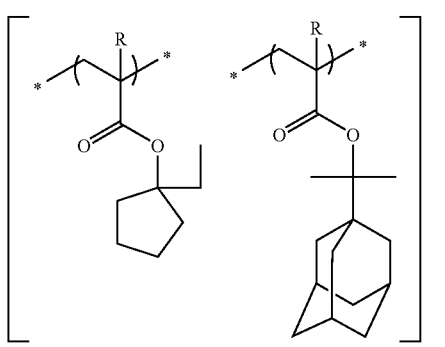
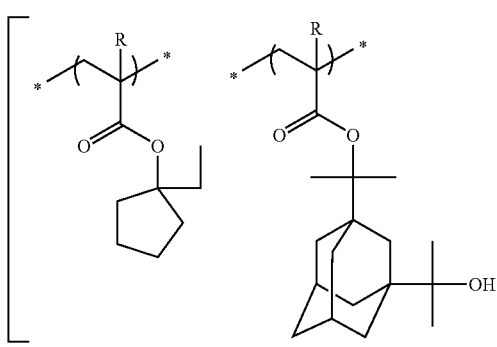
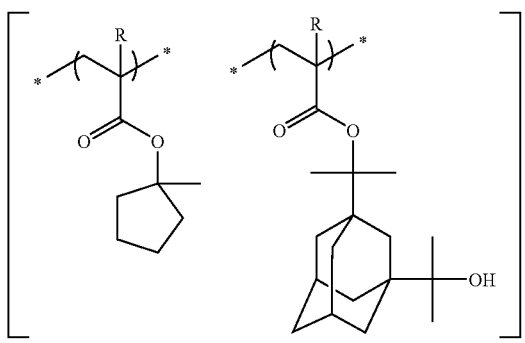
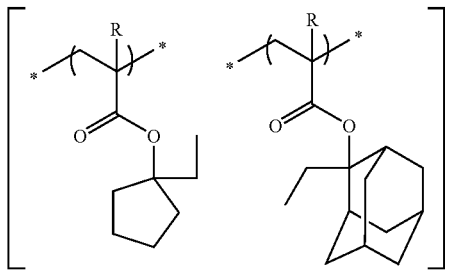
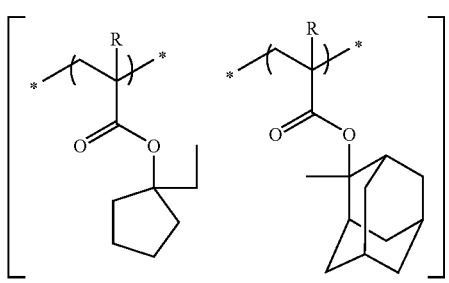
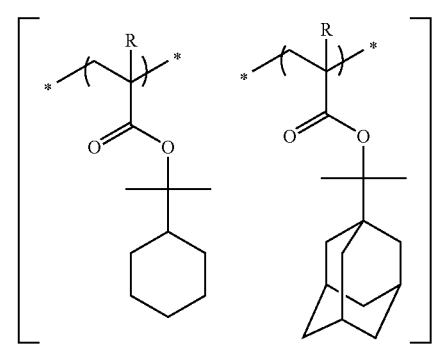
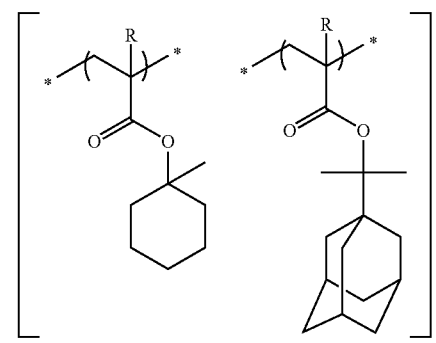
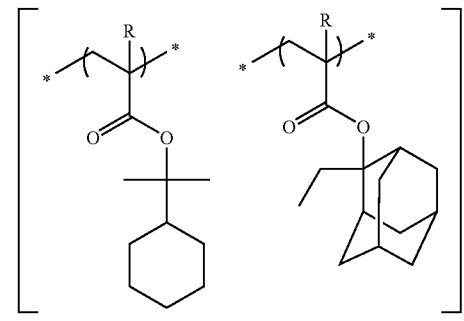
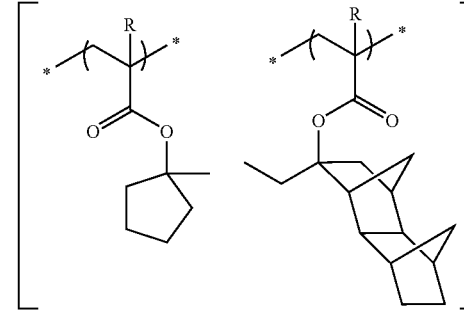
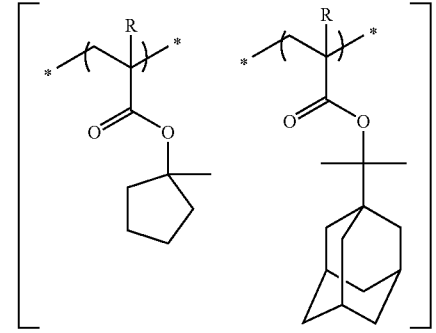

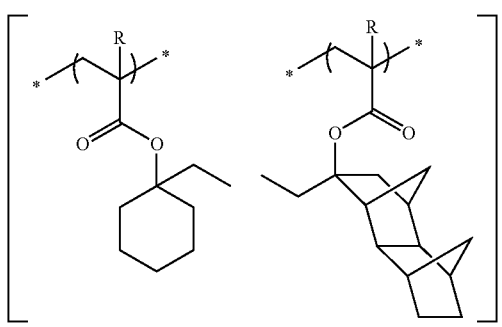

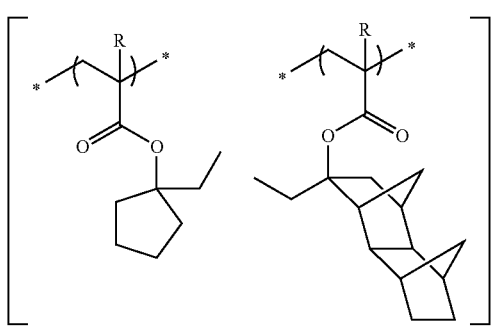

It is preferred for the resin (A) to further have a repeating unit having at least one group selected from among a lactone group, a hydroxyl group, a cyano group and an alkali soluble group.

The repeating unit having a lactone group that may be contained in the resin (A) will now be described.

Any lactone groups can be employed as long as a lactone structure is contained therein. However, 5 to 7-membered ring lactone structures are preferred, and in particular, those resulting from condensation of 5 to 7-membered ring lactone structures with other cyclic structures effected in a fashion to form a bicyclo structure or spiro structure are preferred. The possession of the repeating unit having the lactone structure represented by any of the following general formulae (LC1-1) to (LC1-17) is more preferred. The lactone structures may be directly bonded to the principal chain. Preferred lactone structures are those of the formulae (LC1-1), (LC1-4), (LC1-5), (LC1-6), (LC1-13), (LC1-14) and (LC1-17). The use of these specified lactone structures would ensure improvement in line edge roughness and development defect.

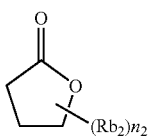

LC1-1

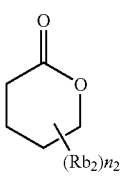

LC1-2

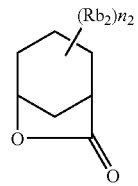

LC1-3

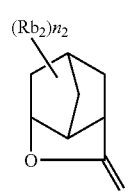

LC1-4

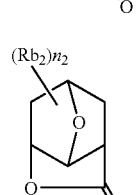

LC1-5

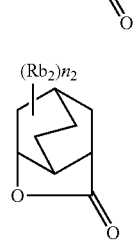

LC1-6

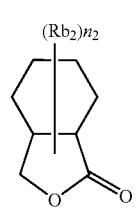

LC1-7

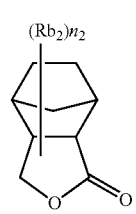

LC1-8

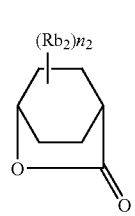

LC1-9

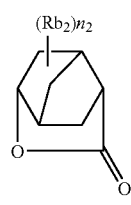

LC1-10

LC1-11

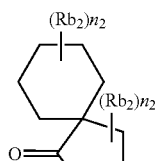

LC1-12

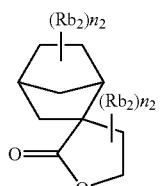

LC1-13

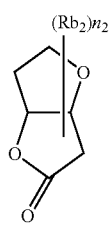

LC1-14

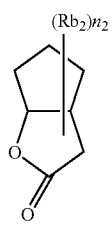

LC1-15

LC1-16

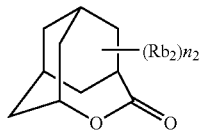

LC1-17

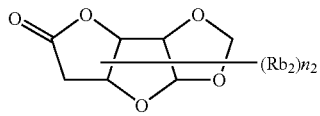

The inclusion of a substituent ($Rb_2$) on the portion of the lactone structure is optional. As a preferred substituent ($Rb_2$), there can be mentioned an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, an acid-decomposable group or the like. Of these, an alkyl group having 1 to 4 carbon atoms, a cyano group and an acid-decomposable group are more preferred. In the formulae, $n_2$ is an integer of 0 to 4. When $n_2$ is 2 or greater, the plurality of present substituents ($Rb_2$) may be identical to or different from each other. Further, the plurality of present substituents ($Rb_2$) may be bonded with each other to thereby form a ring.

As the repeating unit with a lactone structure represented by any of the general formulae (LC1-1) to (LC1-17), there can be mentioned the repeating units represented by the following general formula (AII).

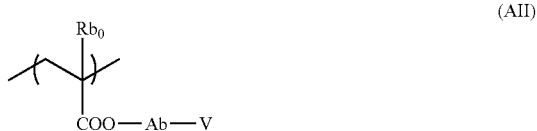

(AII)

In the general formula (AII), $Rb_0$ represents a hydrogen atom, a halogen atom or an optionally substituted alkyl group having 1 to 4 carbon atoms. As a preferred possible substituent of the alkyl group represented by $Rb_0$, there can be mentioned a hydroxyl group or a halogen atom. As the halogen atom represented by $Rb_0$, there can be mentioned a fluorine atom, a chlorine atom, a bromine atom or an iodine atom. As $Rb_0$, a hydrogen atom, a methyl group, a hydroxymethyl group and a trifluoromethyl group are preferred, and a hydrogen atom and a methyl group are especially preferred.

Ab represents a single bond, an alkylene group, a bivalent connecting group with an alicyclic hydrocarbon structure of a single ring or multiple rings, an ether group, an ester group, a carbonyl group, or a bivalent connecting group resulting from a combination thereof. A single bond and a bivalent connecting group of the formula $-Ab_1-CO_2-$ are preferred.

$Ab_1$ is a linear or branched alkylene group or a monocyclic or polycyclic alkylene group, being preferably a methylene group, an ethylene group, a cyclohexylene group, an adamantylene group or a norbornylene group.

V represents a group with a structure represented by any of the general formulae (LC1-1) to (LC1-17).

Examples of the repeating units having a lactone group will now be shown, which however in no way limit the scope of the present invention. In the formulae, Rx represents H, $CH_3$, $CH_2OH$ or $CF_3$.

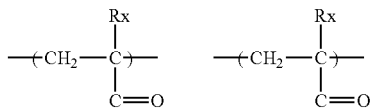
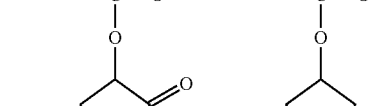
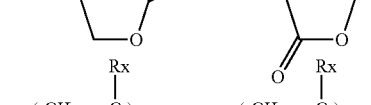
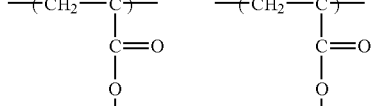
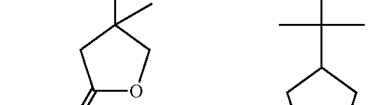
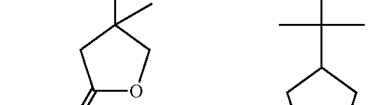

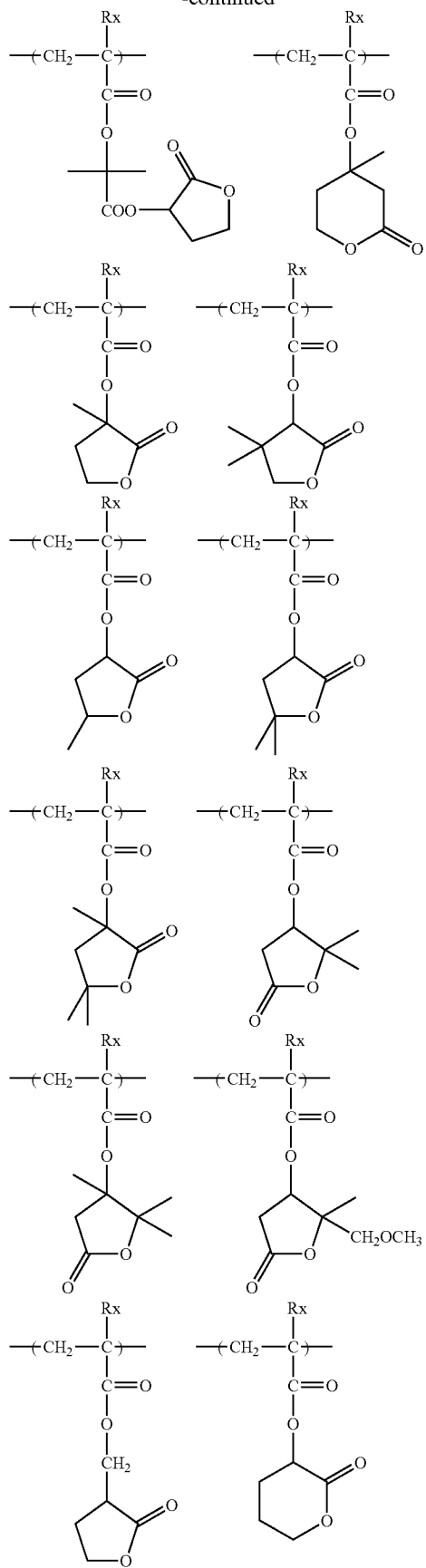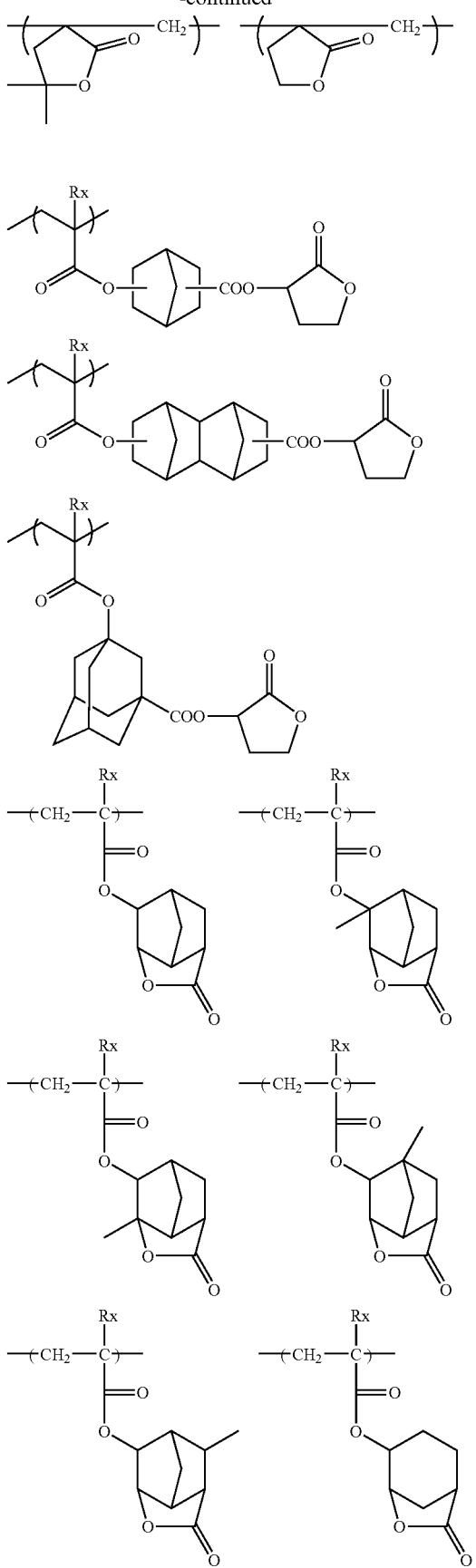

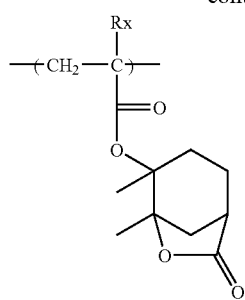
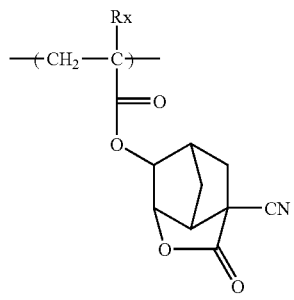
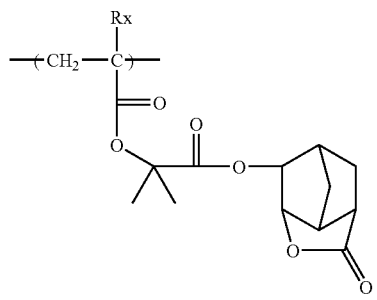
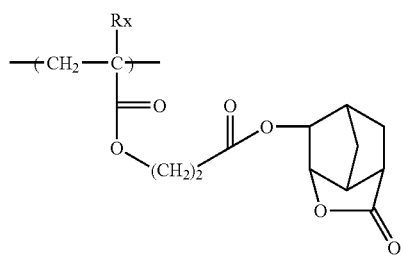
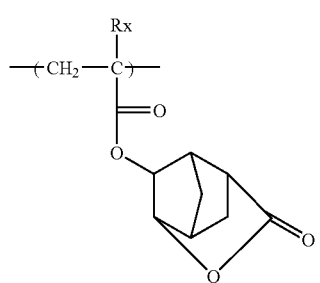
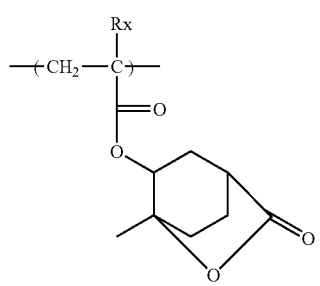
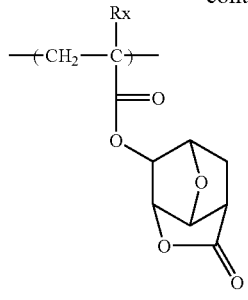
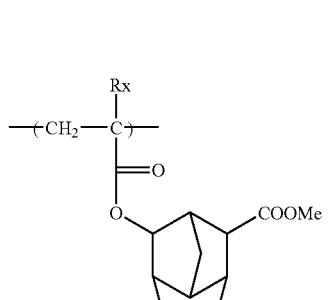
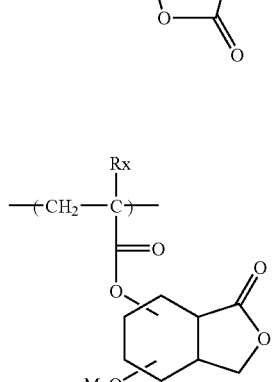
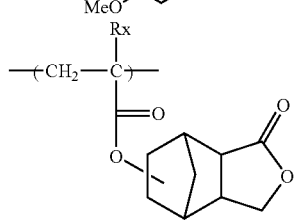
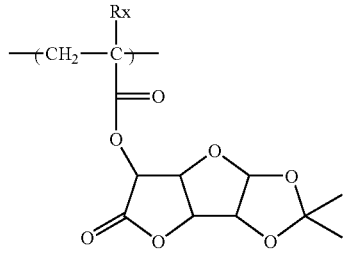
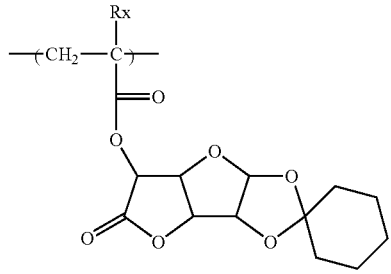

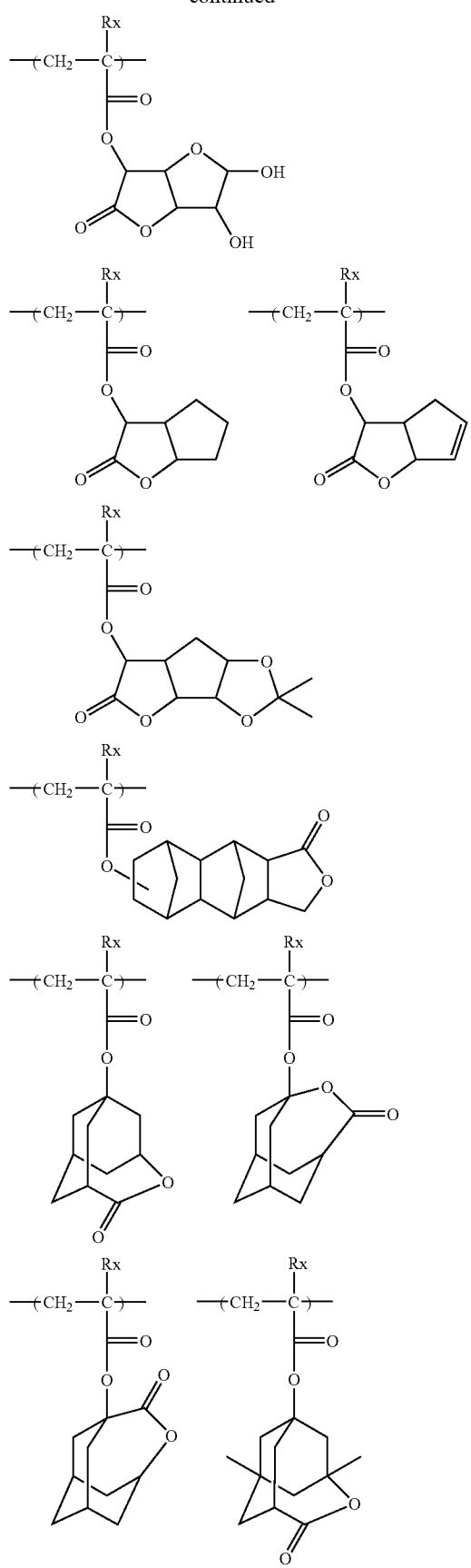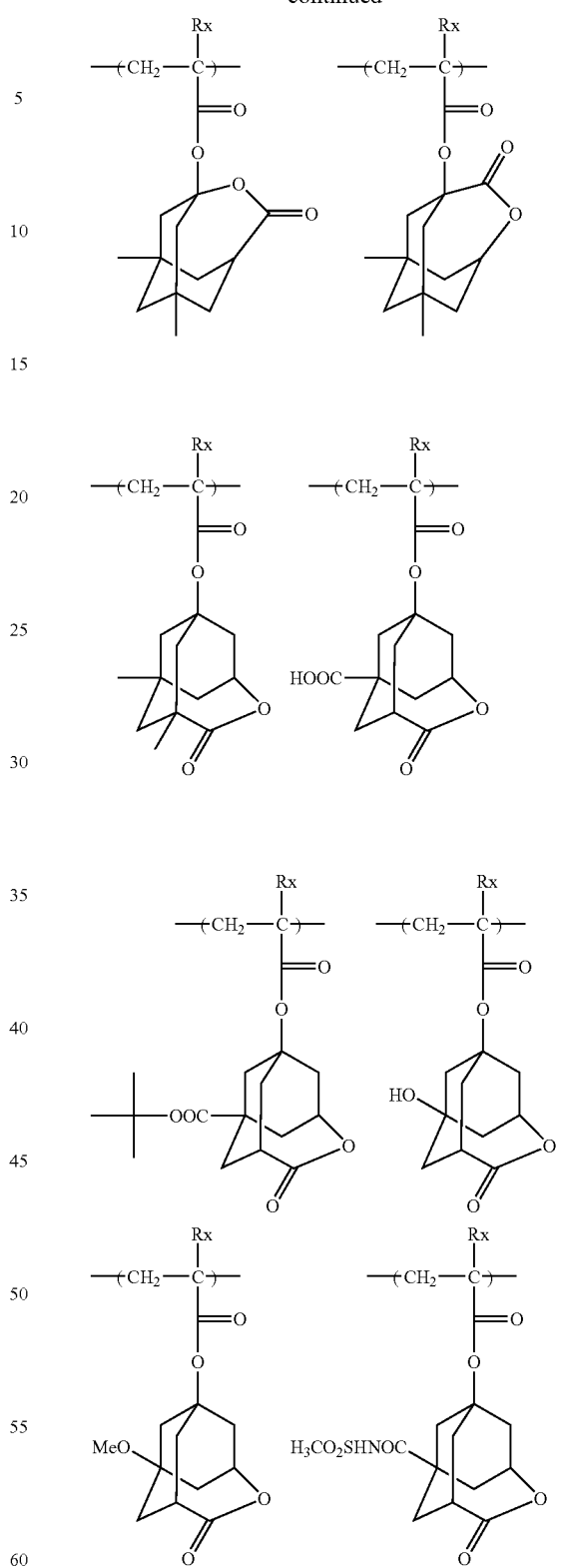
The repeating units having especially preferred lactone groups will be shown below. An improvement in pattern profile and optical density dependence can be attained by selection of the most appropriate lactone group. In the formulae, Rx represents H, $CH_3$, $CH_2OH$ or $CF_3$.

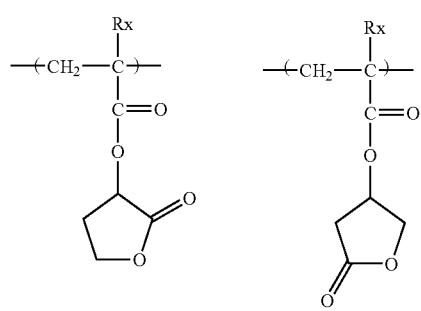
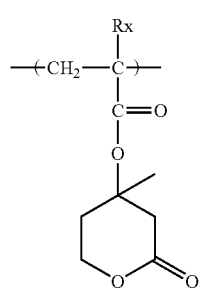
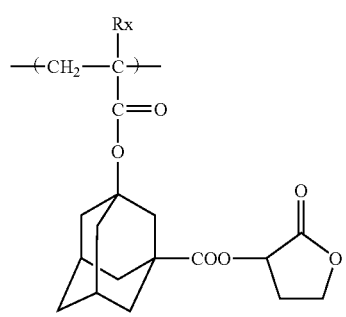
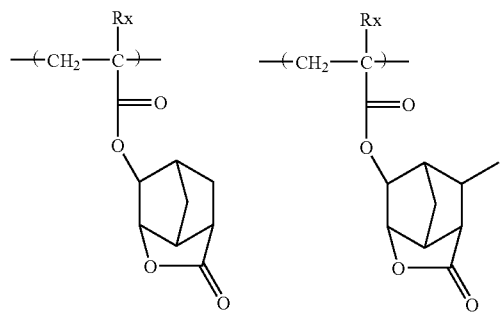
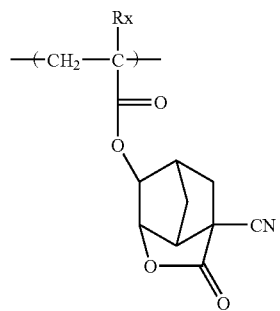
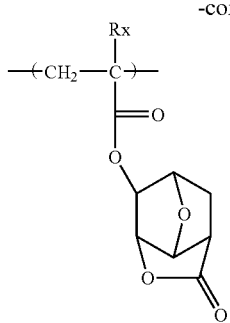
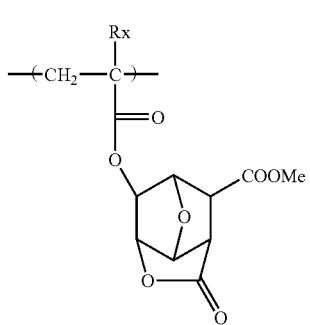
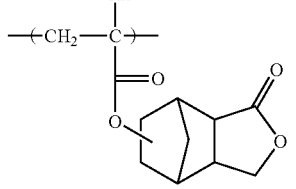
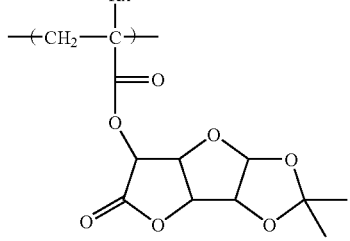
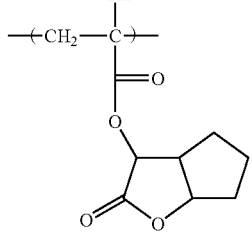
Preferably, the resin (A) for use in the present invention contains a repeating unit with a lactone group represented by the following general formula (2).
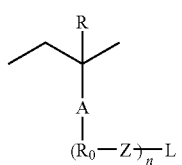
(2)

In the general formula (2),

R represents a hydrogen atom, a halogen atom or an optionally substituted alkyl group;

A represents:

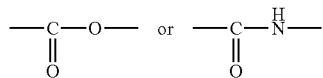

$R_0$, each independently in the presence of two or more groups, represents an optionally substituted alkylene group, an optionally substituted cycloalkylene group or a combination thereof.

Z, each independently in the presence of two or more groups, represents an ether bond, an ester bond, an amido bond, a urethane bond or a urea bond. Of these, an ether bond and an ester bond are preferred, and an ester bond is especially preferred.

L represents a substituent with a lactone structure; and n represents the number of repetitions and is an integer of 1 to 5, preferably 0 or 1.

A further detailed description will be made with respect to the general formula (2).

The alkyl group represented by R is preferably an alkyl group having 1 to 4 carbon atoms, more preferably a methyl group or an ethyl group and most preferably a methyl group. As substituents on R, there can be mentioned, for example, a halogen atom such as a fluorine atom, a chlorine atom or a bromine atom, a mercapto group, a hydroxyl group, an alkoxy group such as a methoxy group, an ethoxy group, an isopropoxy group, a t-butoxy group or a benzyloxy group, an acyl group such as an acetyl group or a propionyl group, and an acetoxy group. R is preferably a hydrogen atom, a methyl group, a trifluoromethyl group or a hydroxymethyl group.

The group represented by $R_0$ is not particularly limited as long as it is a chain alkylene group or a cycloalkylene group. The chain alkylene group is preferably a chain alkylene group having 1 to 10 carbon atoms, more preferably 1 to 5 carbon atoms, for example, a methylene group, an ethylene group, a propylene group or the like. The cycloalkylene group is preferably a cycloalkylene group having 4 to 20 carbon atoms. As such, there can be mentioned, for example, cyclohexylene, cyclopentylene, norbornylene, adamantylene or the like. The chain alkylene groups are preferred from the viewpoint of the exertion of the effect of the present invention. A methylene group is especially preferred.

The substituent with a lactone structure represented by L is the same as the above-mentioned lactone group and is not limited as long as the lactone structure is contained. As particular examples thereof, there can be mentioned the lactone structures of the general formulae (LC1-1) to (LC1-17). Of these, the structure of the general formula (LC1-4) is especially preferred. In the general formulae (LC1-1) to (LC1-17), $n_2$ is more preferably 2 or less.

L is preferably a monovalent organic group with an unsubstituted lactone structure or a monovalent organic group with a lactone structure having a methyl group, a cyano group or an alkoxycarbonyl group as a substituent. L is more preferably a monovalent organic group with a lactone structure having a cyano group as a substituent (cyanolactone).

As especially preferred lactone repeating units, there can be mentioned the repeating units of the following general formula (2-1).

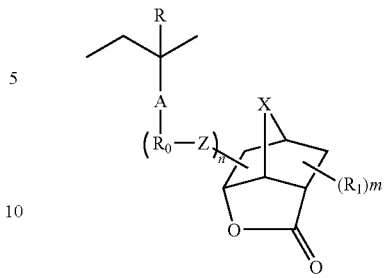

(2-1)

In the general formula (2-1),

R, A, $R_0$, Z and n are as defined above with respect to the general formula (2).

$R_1$, each independently in the presence of two or more groups, represents an optionally substituted alkyl group, an optionally substituted cycloalkyl group, an optionally substituted ester group, a cyano group, a hydroxyl group or an alkoxy group. In the presence of two or more groups, two $R_1$s may be bonded with each other to thereby form a ring.

X represents an alkylene group, an oxygen atom or a sulfur atom, and m is the number of substituents and is an integer of 0 to 5. m is preferably 0 or 1.

A further detailed description will be made with respect to the general formula (2-1).

The preferred examples of the groups represented by R and $R_0$ are the same as mentioned with respect to the general formula (2).

The alkyl group represented by $R_1$ is preferably an alkyl group having 1 to 4 carbon atoms, more preferably a methyl group or an ethyl group and most preferably a methyl group. As the cycloalkyl group, there can be mentioned a cyclopropyl group, a cyclobutyl group, a cyclopentyl group or a cyclohexyl group. As the ester group, there can be mentioned a methoxycarbonyl group, an ethoxycarbonyl group, an n-butoxycarbonyl group, a t-butoxycarbonyl group or the like. As the substituent therefor, there can be mentioned a hydroxyl group, an alkoxy group such as a methoxy group or an ethoxy group, a cyano group, or a halogen atom such as a fluorine atom.

$R_1$ is more preferably a methyl group, a cyano group or an alkoxycarbonyl group, still more preferably a cyano group.

As the alkylene group represented by X, there can be mentioned a methylene group, an ethylene group or the like. X is preferably an oxygen atom or a methylene group, more preferably a methylene group.

When m is 1 or greater, the substitution site of at least one $R_1$ is preferably the α-position or β-position of the carbonyl group of the lactone. The substitution at the α-position is especially preferred.

Specific examples of the repeating units having groups with a lactone structure expressed by the general formula (2) will be shown below, which however in no way limit the scope of the present invention.

In the following specific examples, R represents a hydrogen atom, an optionally substituted alkyl group or a halogen atom. Preferably, R represents a hydrogen atom, a methyl group, a hydroxymethyl group or an acetoxymethyl group.

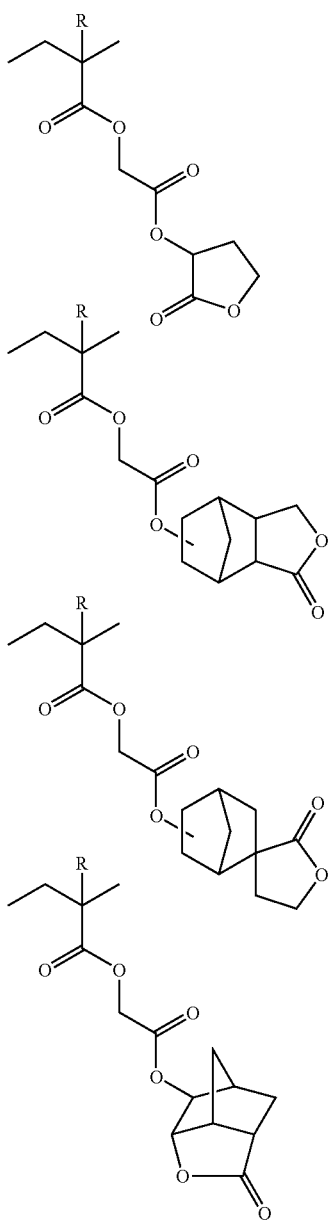
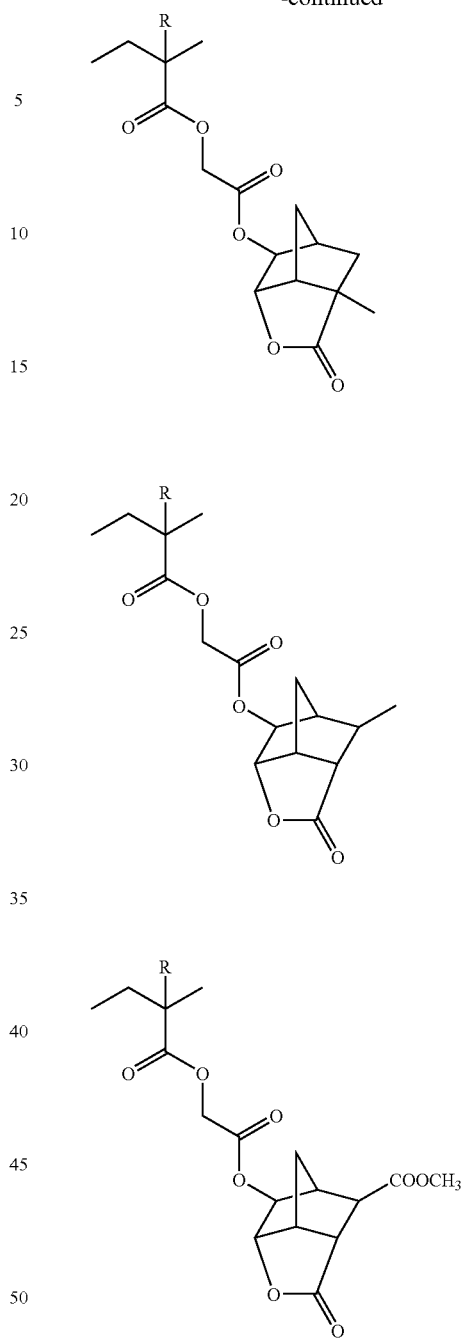
Especially preferred specific examples of the repeating units of the general formula (2-1) are as follows.
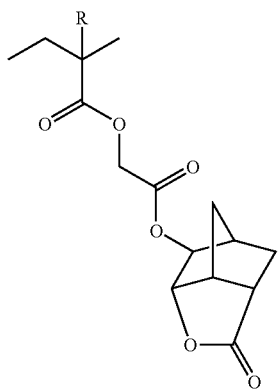
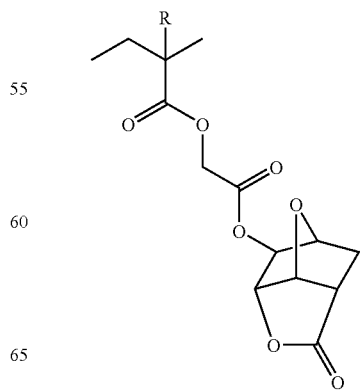

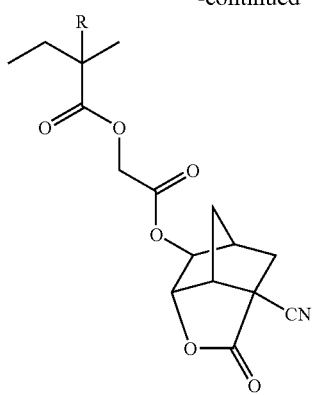
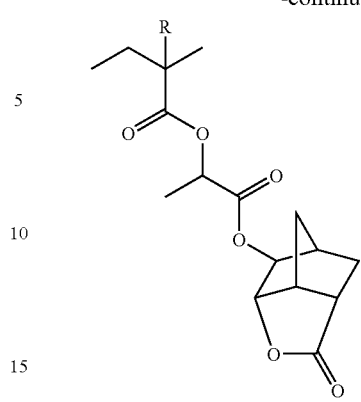
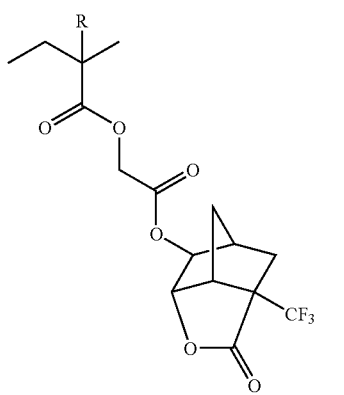
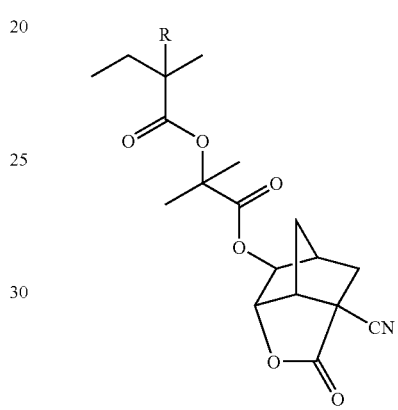
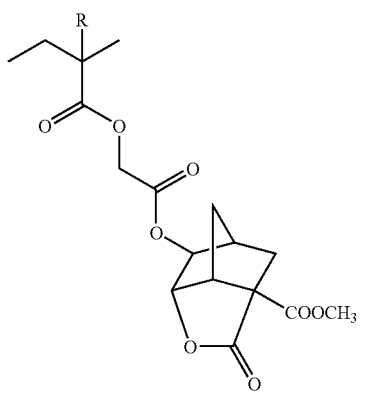
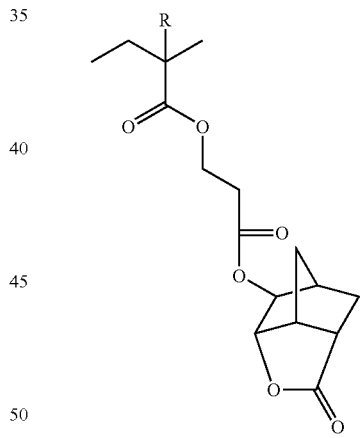
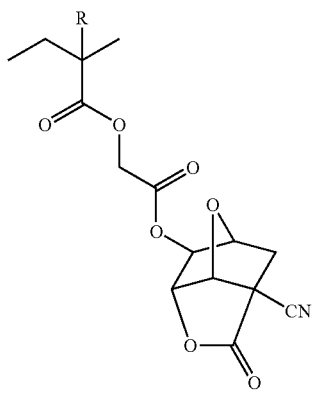
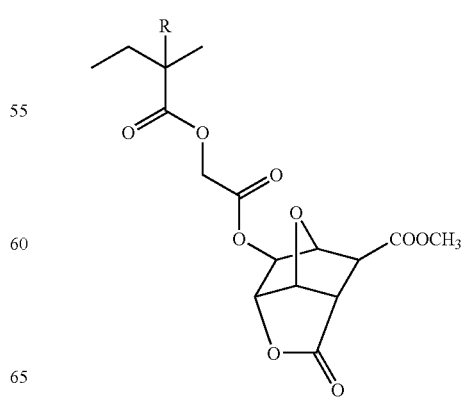

67
-continued
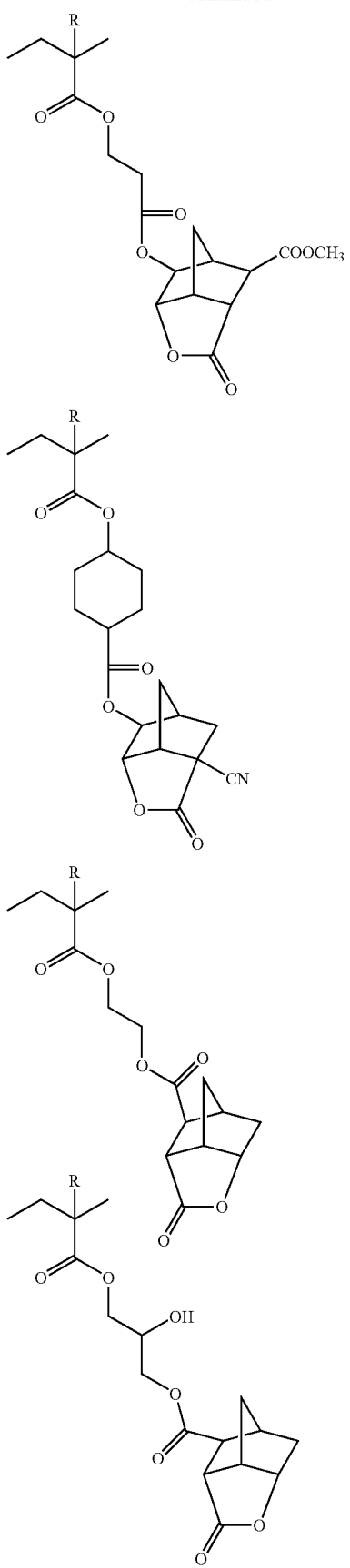
68
-continued
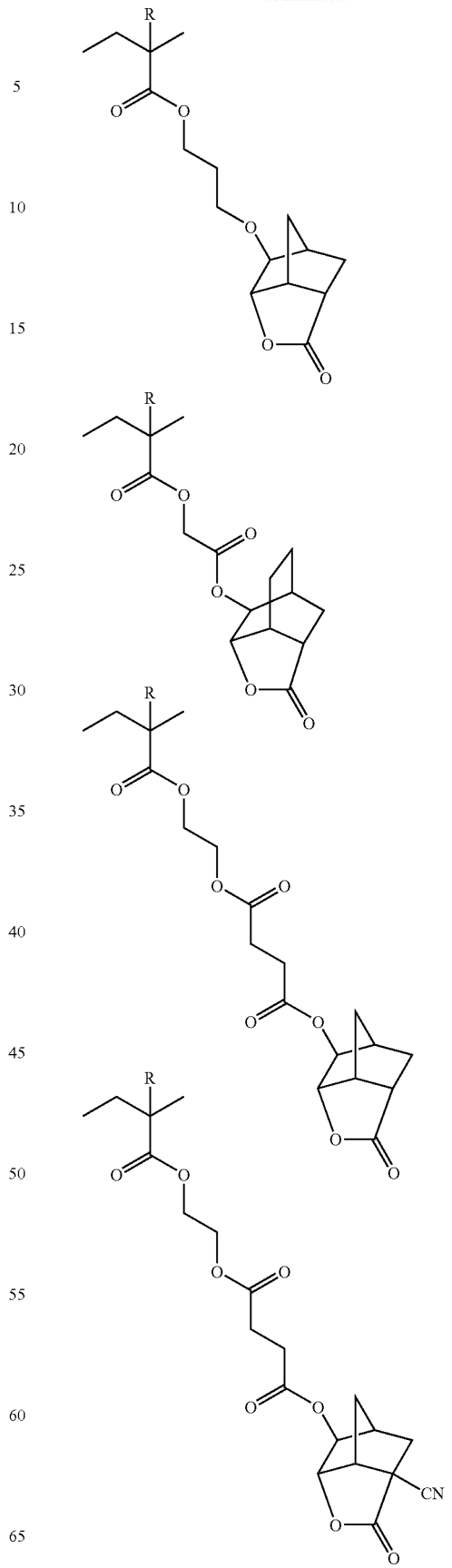

-continued

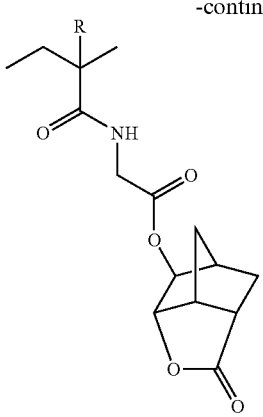

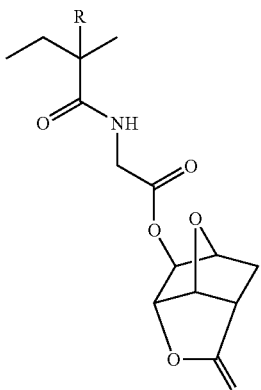

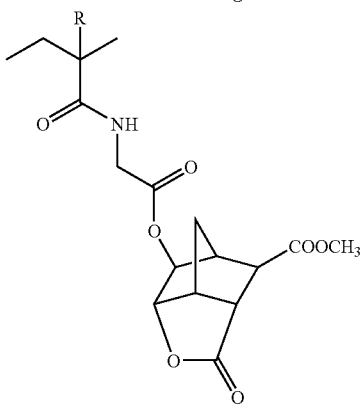

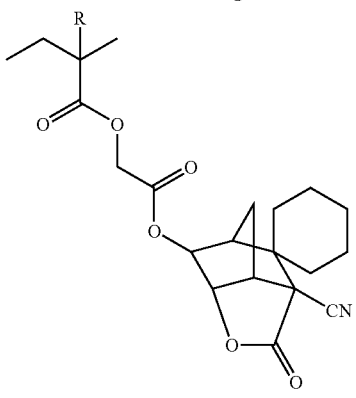

Each of the repeating units having a lactone group is generally present in the form of optical isomers. Any of the optical isomers may be used. It is both appropriate to use a single type of optical isomer alone and to use a plurality of optical isomers in the form of a mixture. When a single type of optical isomer is mainly used, the optical purity (ee) thereof is preferably 90 or higher, more preferably 95 or higher.

The content of repeating units having a lactone group based on all the repeating units of the resin (A) is preferably in the range of 15 to 60 mol %, more preferably 20 to 50 mol % and still more preferably 30 to 50 mol %. Two or more types of lactone repeating units selected from among those of the general formula (1) can be simultaneously employed in order to enhance the effects of the present invention. In the simultaneous employment, it is preferred to select the two or more types from the lactone repeating units of the general formula (I) in which n is 1. It is also preferred to simultaneously employ any of the lactone repeating units of the general formula (AII) in which Ab is a single bond and any of the lactone repeating units of the general formula (I) in which n is 1.

It is preferred for the resin (A) to have a repeating unit other than the repeating units of the above general formulae, having a hydroxyl group or a cyano group. The containment of this repeating unit would realize enhancements of adhesion to substrate and developer affinity. The repeating unit having a hydroxyl group or a cyano group is preferably a repeating unit having an alicyclic hydrocarbon structure substituted with a hydroxyl group or a cyano group. Regarding the alicyclic hydrocarbon structure substituted with a hydroxyl group or a cyano group, the alicyclic hydrocarbon structure preferably consists of an adamantyl group, a diamantyl group or a norbornane group. As preferred alicyclic hydrocarbon structures substituted with a hydroxyl group or a cyano group, there can be mentioned the partial structures of the following general formulae (VIIa) to (VIId).

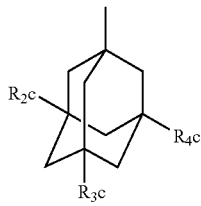
(VIIa)

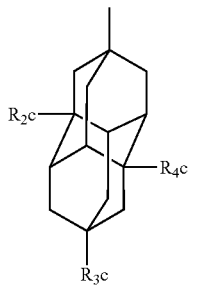
(VIIb)

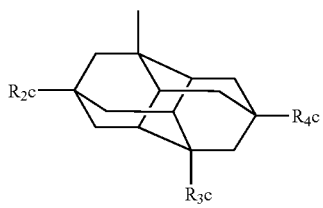
(VIIc)

-continued (VIId)
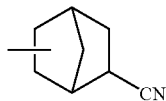

In the general formulae (VIIa) to (VIIc),
each of $R_2c$ to $R_4c$ independently represents a hydrogen atom, a hydroxyl group or a cyano group, provided that at least one of the $R_2c$ to $R_4c$ represents a hydroxyl group or a cyano group. Preferably, one or two of the $R_2c$ to $R_4c$ are hydroxyl groups and the remainder is a hydrogen atom. In the general formula (VIIa), more preferably, two of the $R_2c$ to $R_4c$ are hydroxyl groups and the remainder is a hydrogen atom.

As the repeating units having any of the partial structures of the general formulae (VIIa) to (VIId), there can be mentioned those of the following general formulae (AIIa) to (AIId).

(AIIa)
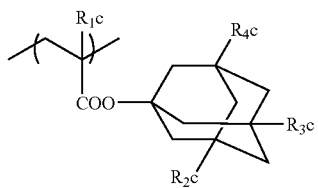

(AIIb)
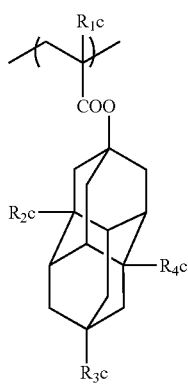

(AIIc)
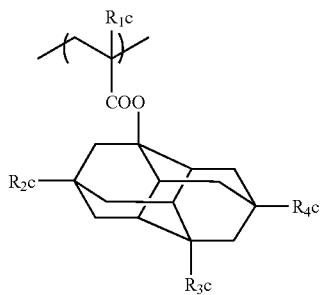

(AIId)
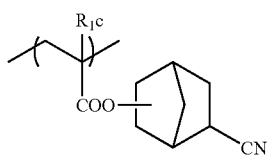

In the general formulae (AIIa) to (AIId),
$R_1c$ represents a hydrogen atom, a methyl group, a trifluoromethyl group or a hydroxymethyl group.
$R_2c$ to $R_4c$ have the same meaning as those of the general formulae (VIIa) to (VIIc).

The content of repeating units having a hydroxyl group or a cyano group, based on all the repeating units of the resin (A), is preferably in the range of 5 to 40 mol %, more preferably 5 to 30 mol % and still more preferably 10 to 25 mol % (provided that none of the above-mentioned repeating units with acid-decomposable groups having a hydroxyl group or a cyano group is contained).

Specific examples of the repeating units having a hydroxyl group or a cyano group will be shown below, which however in no way limit the scope of the present invention.

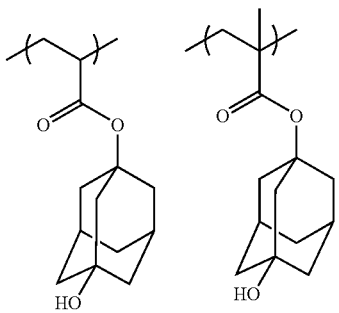

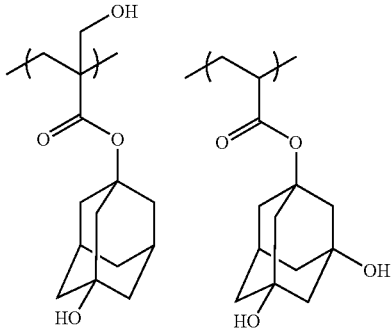

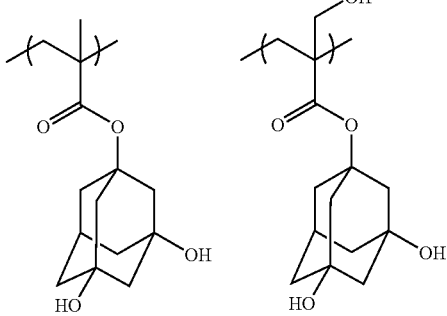

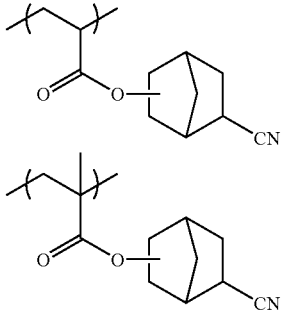

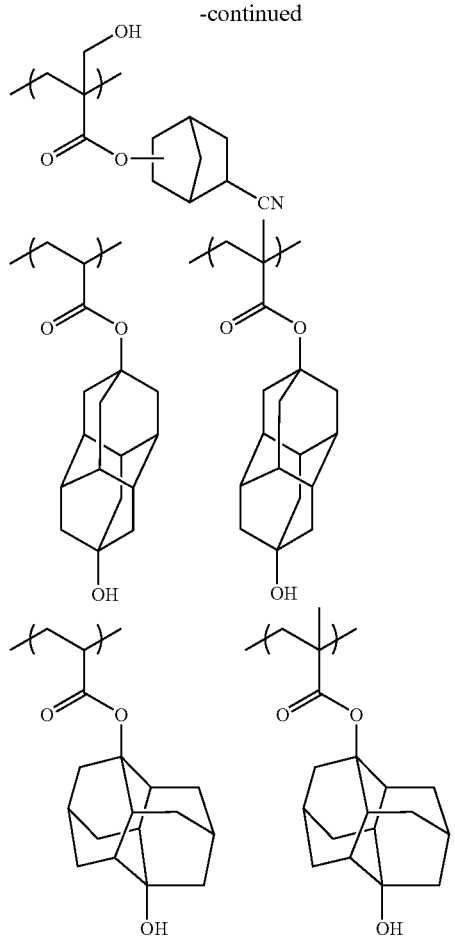

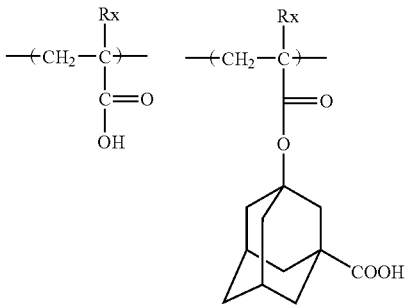

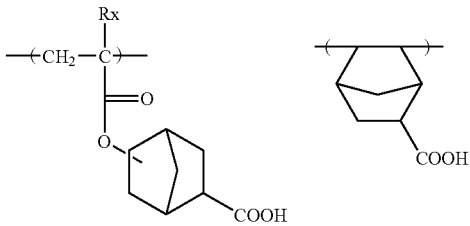

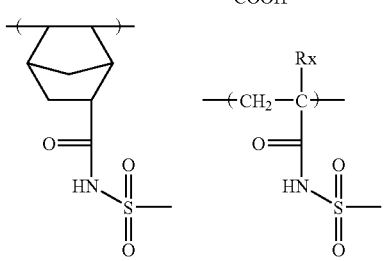

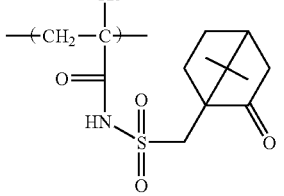

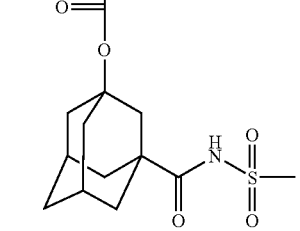

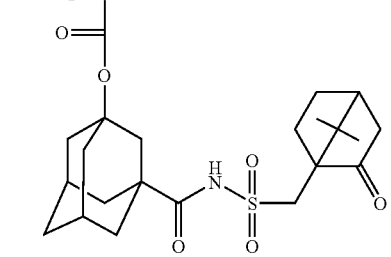

In the formulae, Rx represents H, CH₃, CF₃, or CH₂OH.

It is preferred for the resin as the component (A) to contain a repeating unit having an alkali-soluble group. As the alkali-soluble group, there can be mentioned a carboxyl group, a sulfonamido group, a sulfonylimido group, a bisulfonylimido group or an aliphatic alcohol substituted at its α-position with an electron-withdrawing group (for example, a hexafluoroisopropanol group). The possession of a repeating unit having a carboxyl group is more preferred. The incorporation of the repeating unit having an alkali-soluble group would increase the resolving power in contact hole usage. The repeating unit having an alkali-soluble group is preferably any of a repeating unit wherein the alkali-soluble group is directly bonded to the principal chain of a resin such as a repeating unit of acrylic acid or methacrylic acid, a repeating unit wherein the alkali-soluble group is bonded via a connecting group to the principal chain of a resin and a repeating unit wherein the alkali-soluble group is introduced in a terminal of a polymer chain by the use of a chain transfer agent or polymerization initiator having the alkali-soluble group in the stage of polymerization. The connecting group may have a monocyclic or polycyclic hydrocarbon structure. The repeating unit of acrylic acid or methacrylic acid is especially preferred.

The content of repeating units having an alkali-soluble group based on all the repeating units of the resin (A) is preferably in the range of 0 to 20 mol %, more preferably 3 to 15 mol % and still more preferably 5 to 10 mol %.

Specific examples of the repeating units having an alkali-soluble group will be shown below, which however in no way limit the scope of the present invention.

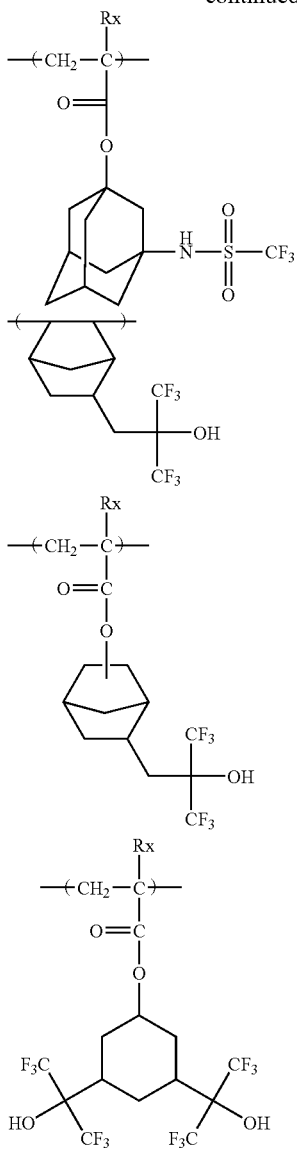

The repeating unit having at least one group selected from among a lactone group, a hydroxyl group, a cyano group and an alkali soluble group is preferably a repeating unit having at least two groups selected from among a lactone group, a hydroxyl group, a cyano group and an alkali soluble group, more preferably a repeating unit having a cyano group and a lactone group. A repeating unit of the structure wherein the above lactone structure (LC1-4) is substituted with a cyano group is especially preferred.

The resin (A) for use in the present invention may further contain any of the repeating units of the general formula (III) having neither a hydroxyl group nor a cyano group.

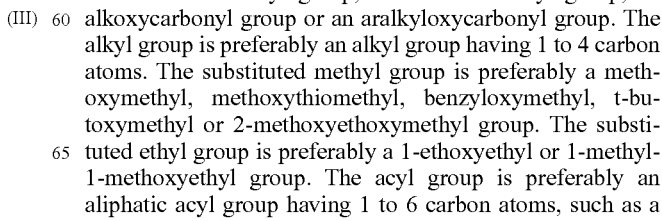

(III)

In the general formula (III), $R_5$ represents a hydrocarbon group having at least one cyclic structure in which neither a hydroxyl group nor a cyano group is contained.

Ra represents a hydrogen atom, an alkyl group or a group of the formula —$CH_2$—O—$Ra_2$ in which $Ra_2$ represents a hydrogen atom, an alkyl group or an acyl group. Ra is preferably a hydrogen atom, a methyl group, a hydroxymethyl group and a trifluoromethyl group, especially preferably a hydrogen atom and a methyl group.

The cyclic structures contained in $R_5$ include a monocyclic hydrocarbon group and a polycyclic hydrocarbon group. As the monocyclic hydrocarbon group, there can be mentioned, for example, a cycloalkyl group having 3 to 12 carbon atoms, such as a cyclopentyl group, a cyclohexyl group, a cycloheptyl group or a cyclooctyl group, or a cycloalkenyl group having 3 to 12 carbon atoms, such as a cyclohexenyl group. Preferably, the monocyclic hydrocarbon group is a monocyclic hydrocarbon group having 3 to 7 carbon atoms. A cyclopentyl group and a cyclohexyl group are more preferred.

The polycyclic hydrocarbon groups include ring-assembly hydrocarbon groups and crosslinked-ring hydrocarbon groups. Examples of the ring-assembly hydrocarbon groups include a bicyclohexyl group, a perhydronaphthalene group and the like. As the crosslinked-ring hydrocarbon rings, there can be mentioned, for example, bicyclic hydrocarbon rings, such as pinane, bornane, norpinane, norbornane and bicyclooctane rings (e.g., bicyclo[2.2.2]octane ring or bicyclo[3.2.1]octane ring); tricyclic hydrocarbon rings, such as homobledane, adamantane, tricyclo[$5.2.1.0^{2,6}$]decane and tricyclo[$4.3.1.1^{2,5}$]undecane rings; and tetracyclic hydrocarbon rings, such as tetracyclo[$4.4.0.1^{2,5}.1^{7,10}$]dodecane and perhydro-1,4-methano-5,8-methanonaphthalene rings. Further, the crosslinked-ring hydrocarbon rings include condensed-ring hydrocarbon rings, for example, condensed rings resulting from condensation of multiple 5- to 8-membered cycloalkane rings, such as perhydronaphthalene (decalin), perhydroanthracene, perhydrophenanthrene, perhydroacenaphthene, perhydrofluorene, perhydroindene and perhydrophenarene rings.

As preferred crosslinked-ring hydrocarbon rings, there can be mentioned, for example, a norbornyl group, an adamantyl group, a bicyclooctanyl group and a tricyclo[$5.2.1.0^{2,6}$]decanyl group. As more preferred crosslinked-ring hydrocarbon rings, there can be mentioned a norbornyl group and an adamantyl group.

These alicyclic hydrocarbon groups may have substituents. As preferred substituents, there can be mentioned, for example, a halogen atom, an alkyl group, a hydroxyl group protected by a protective group and an amino group protected by a protective group. The halogen atom is preferably a bromine, chlorine or fluorine atom, and the alkyl group is preferably a methyl, ethyl, butyl or t-butyl group. The alkyl group may further have a substituent. As the optional further substituent, there can be mentioned a halogen atom, an alkyl group, a hydroxyl group protected by a protective group or an amino group protected by a protective group.

As the protective group, there can be mentioned, for example, an alkyl group, a cycloalkyl group, an aralkyl group, a substituted methyl group, a substituted ethyl group, an alkoxycarbonyl group or an aralkyloxycarbonyl group. The alkyl group is preferably an alkyl group having 1 to 4 carbon atoms. The substituted methyl group is preferably a methoxymethyl, methoxythiomethyl, benzyloxymethyl, t-butoxymethyl or 2-methoxyethoxymethyl group. The substituted ethyl group is preferably a 1-ethoxyethyl or 1-methyl-1-methoxyethyl group. The acyl group is preferably an aliphatic acyl group having 1 to 6 carbon atoms, such as a formyl, acetyl, propionyl, butyryl, isobutyryl, valeryl or pivaloyl group. The alkoxycarbonyl group is, for example, an alkoxycarbonyl group having 1 to 4 carbon atoms.

The content of any of the repeating units of the general formula (III) having neither a hydroxyl group nor a cyano group, based on all the repeating units of the resin (A), is preferably in the range of 0 to 40 mol %, more preferably 0 to 20 mol %.

Specific examples of the repeating units of the general formula (III) will be shown below, which however in no way limit the scope of the present invention. In the formulae, Ra represents H, $CH_3$, $CH_2OH$, or $CF_3$.

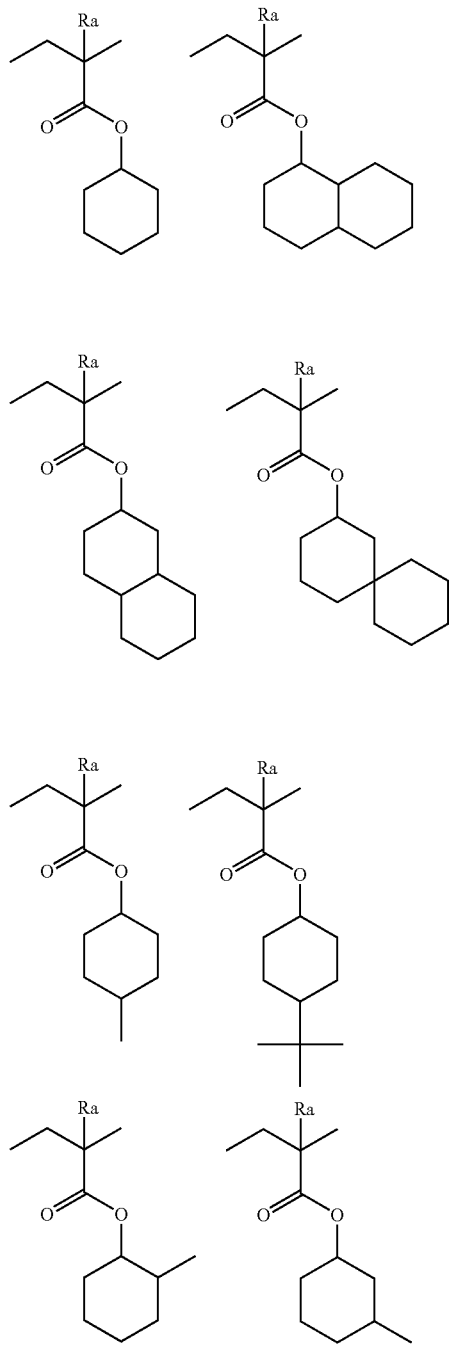

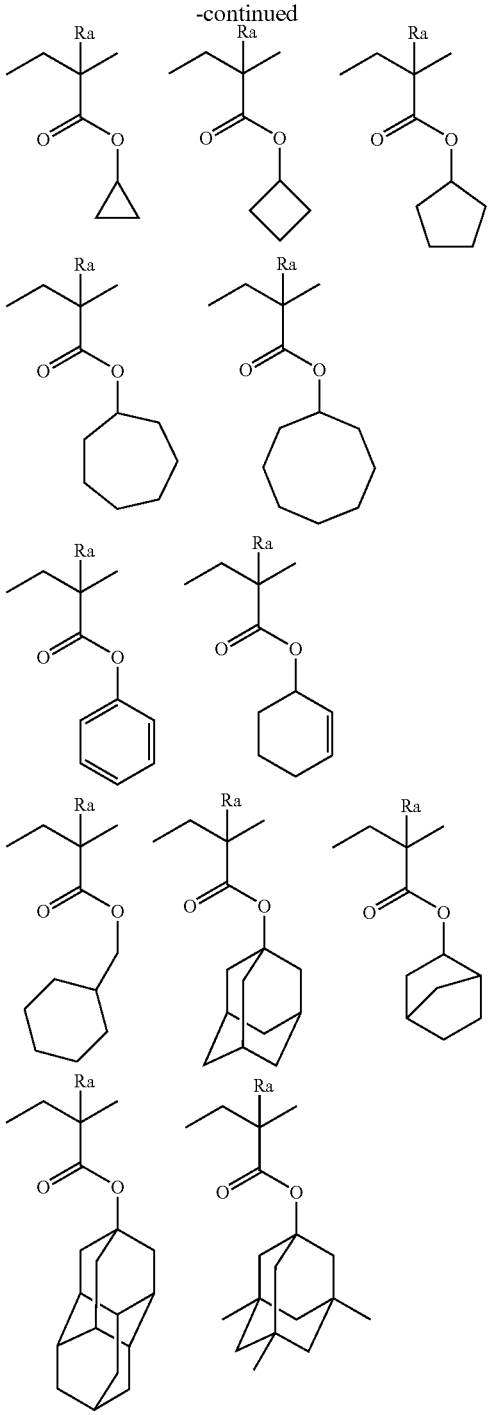

The resin (A) may have, in addition to the foregoing repeating structural units, various repeating structural units for the purpose of regulating the dry etching resistance, standard developer adaptability, substrate adhesion, resist profile and generally required properties of the resist such as resolving power, heat resistance and sensitivity.

As such repeating structural units, there can be mentioned those corresponding to the following monomers, which however are nonlimiting.

The use of such repeating structural units would enable fine regulation of the required properties of the resin (A), especially:

(1) solubility in application solvents,
(2) film forming easiness (glass transition point),
(3) alkali developability,
(4) film thinning (selections of hydrophilicity/hydrophobicity and alkali-soluble group),
(5) adhesion of unexposed area to substrate,
(6) dry etching resistance, etc.

As appropriate monomers, there can be mentioned, for example, a compound having an unsaturated bond capable of addition polymerization, selected from among acrylic esters, methacrylic esters, acrylamides, methacrylamides, allyl compounds, vinyl ethers, vinyl esters and the like.

In addition, any unsaturated compound capable of addition polymerization that is copolymerizable with monomers corresponding to the above various repeating structural units may be copolymerized therewith.

The molar ratios of individual repeating structural units contained in the resin (A) are appropriately determined from the viewpoint of regulation of not only the dry etching resistance of the resist but also the standard developer adaptability, substrate adhesion, resist profile and generally required properties of the resist such as the resolving power, heat resistance and sensitivity.

When the actinic ray-sensitive or radiation-sensitive resin composition of the present invention is one for ArF exposure, it is preferred for the resin as the component (A) to have no aromatic group from the viewpoint of transparency to ArF beams. Further, it is preferred for the resin (A) not to contain a fluorine atom and a silicon atom from the viewpoint of compatibility with a hydrophobic resin (HR) to be described hereinbelow.

In the resin (A), preferably, all the repeating units consist of (meth)acrylate repeating units. In this case, use can be made of any of a resin wherein all the repeating units consist of methacrylate repeating units, a resin wherein all the repeating units consist of acrylate repeating units and a resin wherein all the repeating units consist of methacrylate repeating units and acrylate repeating units. However, it is preferred for the acrylate repeating units to account for 50 mol % or less of all the repeating units. It is more preferred to employ a copolymer containing 20 to 50 mol % of (meth)acrylate repeating units having an acid-decomposable group according to the general formula (AI), 20 to 50 mol % of (meth)acrylate repeating units having a lactone group, 5 to 30 mol % of (meth)acrylate repeating units having an alicyclic hydrocarbon structure substituted with a hydroxyl group or a cyano group and 0 to 20 mol % of other (meth)acrylate repeating units.

In the event of exposure of the actinic ray-sensitive or radiation-sensitive resin composition of the present invention to KrF excimer laser beams, electron beams, X-rays or high-energy light rays of 50 nm or less wavelength (EUV, etc.), it is preferred for the resin (A) to have not only the repeating units of the general formula (AI) but also hydroxystyrene repeating units. More preferably, the resin (A) has hydroxystyrene repeating units, hydroxystyrene repeating units protected by an acid-decomposable group and acid-decomposable repeating units of a (meth)acrylic acid tertiary alkyl ester, etc.

As preferred repeating units having an acid-decomposable group, there can be mentioned, for example, the repeating units derived from t-butoxycarbonyloxystyrene, a 1-alkoxyethoxystyrene and a (meth)acrylic acid tertiary alkyl ester. The repeating units derived from a 2-alkyl-2-adamantyl (meth)acrylate and a dialkyl(1-adamantyl)methyl (meth) acrylate are more preferred.

The resin (A) can be synthesized by conventional techniques (for example, radical polymerization). As general synthetic methods, there can be mentioned, for example, a batch polymerization method in which a monomer species and an initiator are dissolved in a solvent and heated so as to accomplish polymerization and a dropping polymerization method in which a solution of monomer species and initiator is added by dropping to a heated solvent over a period of 1 to 10 hours. The dropping polymerization method is preferred. As a reaction solvent, there can be mentioned, for example, an ether, such as tetrahydrofuran, 1,4-dioxane or diisopropyl ether; a ketone, such as methyl ethyl ketone or methyl isobutyl ketone; an ester solvent, such as ethyl acetate; an amide solvent, such as dimethylformamide or dimethylacetamide; or a solvent capable of dissolving the composition of the present invention, such as propylene glycol monomethyl ether acetate, propylene glycol monomethyl ether or cyclohexanone, to be hereinafter described. It is preferred to perform the polymerization with the use of the same solvent as employed in the photosensitive composition of the present invention. This would inhibit any particle generation during storage.

The polymerization reaction is preferably carried out in an atmosphere of inert gas, such as nitrogen or argon. The polymerization is initiated by the use of a commercially available radical initiator (azo initiator, peroxide, etc.) as a polymerization initiator. Among the radical initiators, an azo initiator is preferred. An azo initiator having an ester group, a cyano group or a carboxyl group is especially preferred. As preferred initiators, there can be mentioned azobisisobutyronitrile, azobisdimethylvaleronitrile, dimethyl 2,2'-azobis(2-methylpropionate) and the like. According to necessity, a supplementation of initiator or divided addition thereof may be effected. After the completion of the reaction, the reaction mixture is poured into a solvent. The desired polymer is recovered by a method for powder or solid recovery, etc. The concentration during the reaction is in the range of 5 to 50 mass %, preferably 10 to 30 mass %. The reaction temperature is generally in the range of 10° to 150° C., preferably 300 to 120° C. and more preferably 600 to 100° C.

The weight average molecular weight of the resin (A) in terms of polystyrene molecular weight as measured by GPC is preferably in the range of 1000 to 200,000, more preferably 2000 to 20,000, still more preferably 3000 to 15,000 and further preferably 3000 to 10,000. The regulation of the weight average molecular weight to 1000 to 200,000 would prevent deteriorations of heat resistance and dry etching resistance and also prevent deterioration of developability and increase of viscosity leading to a poor film forming property.

Use is made of the resin whose degree of dispersal (molecular weight distribution) is generally in the range of 1 to 3, preferably 1 to 2.6, more preferably 1 to 2 and most preferably 1.4 to 1.7. The lower the molecular weight distribution, the better the resolving power and resist profile and the smoother the side wall of the resist pattern to thereby attain excellence in roughness.

The amount of resin (A) contained in the actinic ray-sensitive or radiation-sensitive resin composition of the present invention is preferably in the range of 50 to 99 mass %, more preferably 60 to 98 mass % based on the total solid content of the composition.

In the present invention, the resins (A) may be used either individually or in combination.

3. Resin not Having any Group that is Decomposed by the Action of an Acid (Resin (D))

The photosensitive composition of the present invention may contain a resin (D) not having any group that is decomposed by the action of an acid. The expression "not having any group that is decomposed by the action of an acid" means that no decomposability by the action of an acid is exhibited in the image forming process generally employed for the photosensitive composition of the present invention, or the decomposability is extremely low, so that substantially no group contributory to the image formation by acid-induced decomposition is contained. As such a resin, there can be mentioned a resin having an alkali-soluble group or a resin having a group that is decomposed by the action of an alkali so as to increase its solubility in an alkali developer.

The resin (D) is preferably a resin having at least one repeating unit derived from a (meth)acrylic acid derivative and/or an alicyclic olefin derivative.

The alkali-soluble group that can be contained in the resin (D) is preferably a carboxyl group, a phenolic hydroxyl group, an aliphatic hydroxyl group substituted at its 1-position or 2-position with an electron withdrawing group, an amino group substituted with an electron withdrawing group (for example, a sulfonamido group, a sulfonimido group or a bissulfonylimido group) or a methylene group or methine group substituted with an electron withdrawing group (for example, a methylene group or methine group substituted with at least two groups selected from among ketone and ester groups).

The group decomposable by the action of an alkali so as to increase its solubility in an alkali developer that can be contained in the resin (D) is preferably a lactone group or an acid anhydride group, more preferably a lactone group. As the repeating unit having the group decomposable by the action of an alkali so as to increase its solubility in an alkali developer, in particular, there can be mentioned any of the following repeating units.

The resin (D) may have a repeating unit having a functional group other than those mentioned above. In the repeating unit having such other functional group, an appropriate functional group can be introduced taking into account the dry etching resistance, hydrophilic/hydrophobic property, interaction, etc.

As such, in particular, there can be mentioned a repeating unit having a polar functional group such as a hydroxyl group, a cyano group, a carbonyl group or an ester group, a repeating unit having a monocyclic or polycyclic hydrocarbon structure, a repeating unit having a silicon atom, a halogen atom or a fluoroalkyl group, or a repeating unit having two or more of these functional groups.

Specific examples of the preferred repeating units that can construct the resin (D) are shown below.

(D-1)

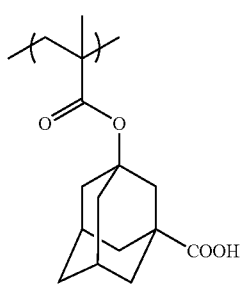
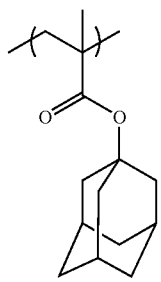

(D-2)

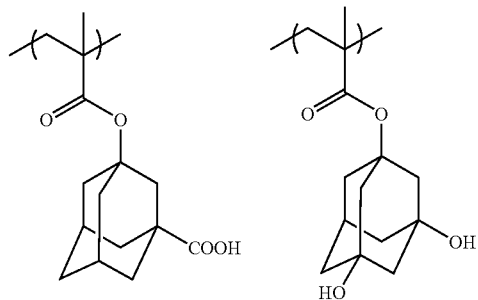

(D-3)

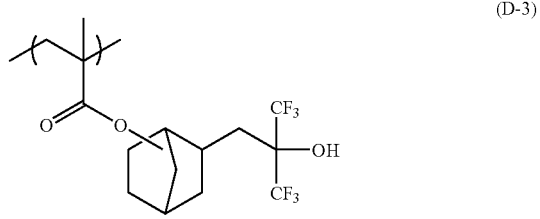

(D-4)

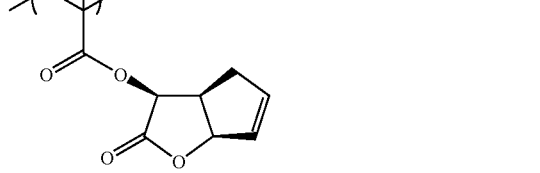

(D-5)

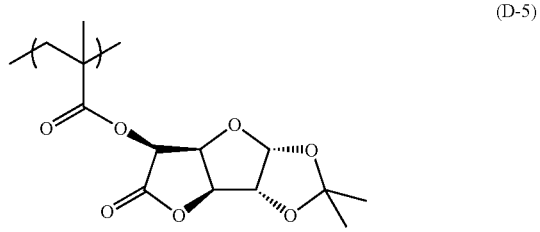

(D-6)

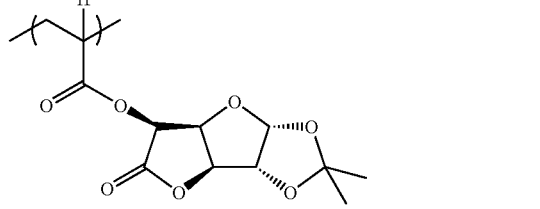

(D-7)

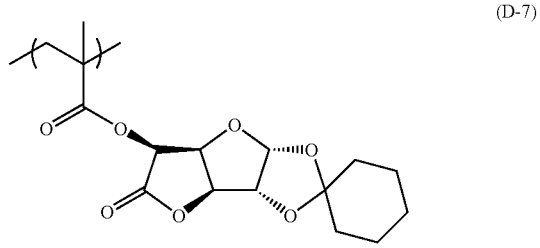

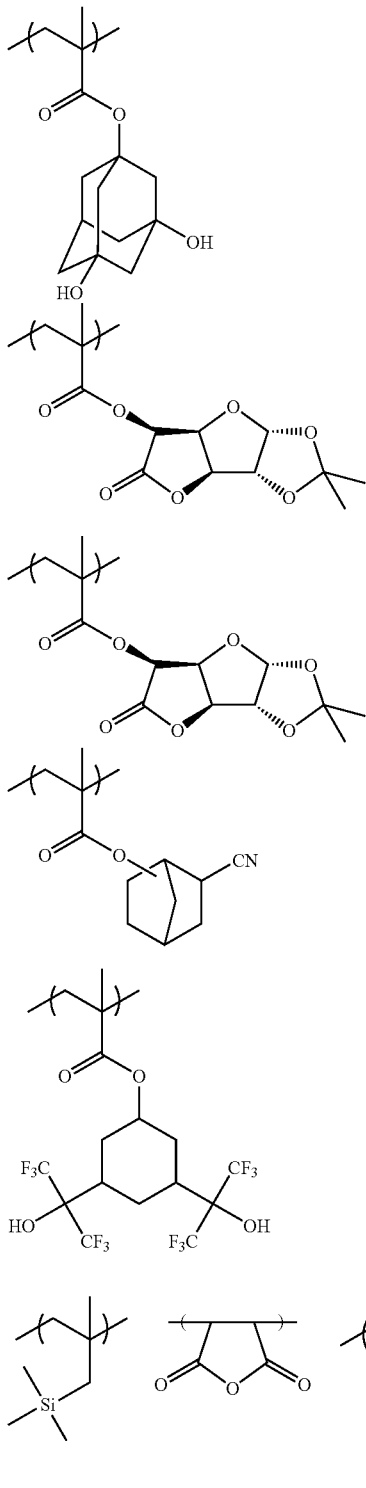

The ratio of resin (D) added is preferably in the range of 0 to 30 mass %, more preferably 0 to 20 mass % and still more preferably 0 to 15 mass % based on the mass of the resin (A).

4. Solvent

The photosensitive composition of the present invention may contain a solvent. The solvent is not limited as long as it can be used in the preparation of a positive resist composition through dissolution of the above-mentioned components. As the solvent, there can be mentioned, for example, an organic solvent, such as an alkylene glycol monoalkyl ether carboxylate, an alkylene glycol monoalkyl ether, an alkyl lactate, an alkyl alkoxypropionate, a cyclolactone (preferably having 4 to 10 carbon atoms), an optionally cyclized monoketone compound (preferably having 4 to 10 carbon atoms), an alkylene carbonate, an alkyl alkoxyacetate or an alkyl pyruvate.

As preferred alkylene glycol monoalkyl ether carboxylates, there can be mentioned, for example, propylene glycol monomethyl ether acetate, propylene glycol monoethyl ether acetate, propylene glycol monopropyl ether acetate, propylene glycol monobutyl ether acetate, propylene glycol monomethyl ether propionate, propylene glycol monoethyl ether propionate, ethylene glycol monomethyl ether acetate and ethylene glycol monoethyl ether acetate.

As preferred alkylene glycol monoalkyl ethers, there can be mentioned, for example, propylene glycol monomethyl ether, propylene glycol monoethyl ether, propylene glycol monopropyl ether, propylene glycol monobutyl ether, ethylene glycol monomethyl ether and ethylene glycol monoethyl ether.

As preferred alkyl lactates, there can be mentioned, for example, methyl lactate, ethyl lactate, propyl lactate and butyl lactate.

As preferred alkyl alkoxypropionates, there can be mentioned, for example, ethyl 3-ethoxypropionate, methyl 3-methoxypropionate, methyl 3-ethoxypropionate and ethyl 3-methoxypropionate.

As preferred cyclolactones, there can be mentioned, for example, β-propiolactone, β-butyrolactone, γ-butyrolactone, α-methyl-γ-butyrolactone, β-methyl-γ-butyrolactone, γ-valerolactone, γ-caprolactone, γ-octanoic lactone and α-hydroxy-γ-butyrolactone.

As preferred optionally cyclized monoketone compounds, there can be mentioned, for example, 2-butanone, 3-methylbutanone, pinacolone, 2-pentanone, 3-pentanone, 3-methyl-2-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 2-heptanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexen-2-one, 3-penten-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone and 3-methylcycloheptanone.

As preferred alkylene carbonates, there can be mentioned, for example, propylene carbonate, vinylene carbonate, ethylene carbonate and butylene carbonate.

As preferred alkyl alkoxyacetates, there can be mentioned, for example, acetic acid 2-methoxyethyl ester, acetic acid 2-ethoxyethyl ester, acetic acid 2-(2-ethoxyethoxy)ethyl ester, acetic acid 3-methoxy-3-methylbutyl ester and acetic acid 1-methoxy-2-propyl ester.

As preferred alkyl pyruvates, there can be mentioned, for example, methyl pyruvate, ethyl pyruvate and propyl pyruvate.

As a preferably employable solvent, there can be mentioned a solvent having a boiling point of 130° C. or above measured at ordinary temperature under ordinary pressure.

For example, there can be mentioned cyclopentanone, γ-butyrolactone, cyclohexanone, ethyl lactate, ethylene glycol monoethyl ether acetate, propylene glycol monomethyl ether acetate, ethyl 3-ethoxypropionate, ethyl pyruvate, acetic acid 2-ethoxyethyl ester, acetic acid 2-(2-ethoxyethoxy)ethyl ester or propylene carbonate.

In the present invention, these solvents may be used either individually or in combination.

In the present invention, a mixed solvent consisting of a mixture of a solvent having a hydroxyl group in its structure and a solvent having no hydroxyl group may be used as the organic solvent.

As the solvent having a hydroxyl group, there can be mentioned, for example, ethylene glycol, ethylene glycol monomethyl ether, ethylene glycol monoethyl ether, propylene glycol, propylene glycol monomethyl ether, propylene glycol monoethyl ether, ethyl lactate or the like. Of these, propylene glycol monomethyl ether and ethyl lactate are especially preferred.

As the solvent having no hydroxyl group, there can be mentioned, for example, propylene glycol monomethyl ether acetate, ethyl ethoxypropionate, 2-heptanone, γ-butyrolactone, cyclohexanone, butyl acetate, N-methylpyrrolidone, N,N-dimethylacetamide, dimethyl sulfoxide or the like. Of these, propylene glycol monomethyl ether acetate, ethyl ethoxypropionate, 2-heptanone, γ-butyrolactone, cyclohexanone and butyl acetate are especially preferred. Propylene glycol monomethyl ether acetate, ethyl ethoxypropionate and 2-heptanone are most preferred.

The mixing ratio (mass) of a solvent having a hydroxyl group and a solvent having no hydroxyl group is in the range of 1/99 to 99/1, preferably 10/90 to 90/10 and more preferably 20/80 to 60/40. The mixed solvent containing 50 mass % or more of a solvent having no hydroxyl group is especially preferred from the viewpoint of uniform applicability.

It is preferred for the solvent to be a mixed solvent consisting of two or more solvents containing propylene glycol monomethyl ether acetate.

5. Acid Diffusion Inhibitor (C)

The positive photosensitive composition of the present invention may contain two or more types of acid diffusion inhibitors capable of controlling the diffusion of the acids generated from the sulfonic acid generators (B) so as to decrease any performance alteration over time from exposure to heating.

The capability of inhibition of the acid diffusion can be judged on the basis of, as an index, a sensitivity decrease at the optimum exposure intensity in the procedure including exposure operation, development and pattern formation.

Further, containing two or more types of acid diffusion inhibitors contributes to inhibition of the "pattern collapse", that is desired in lithography. The particular reason therefor has not been elucidated, but it is presumed that such pattern collapse inhibition would result from the stepwise multistage control of diffusion of the generated acid, which is itself realized by the joint use of a multiplicity of different types of acid diffusion inhibitors.

As examples of the acid diffusion inhibitors, there can be mentioned a basic compound and a carboxylic acid onium salt.

As preferred basic compounds, there can be mentioned the compounds having the structures of the following formulae (A) to (E).

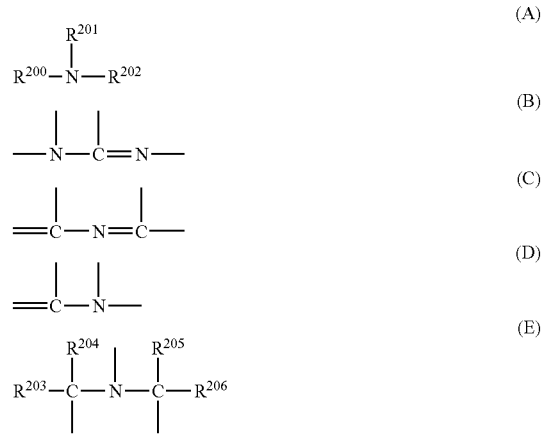

In the general formulae (A) and (E), $R^{200}$, $R^{201}$ and $R^{202}$ may be identical to or different from each other and each represent a hydrogen atom, an alkyl group (preferably having 1 to 20 carbon atoms), a cycloalkyl group (preferably having 3 to 20 carbon atoms) or an aryl group (having 6 to 20 carbon atoms). $R^{201}$ and $R^{202}$ may be bonded with each other to thereby form a ring.

$R^{203}$, $R^{204}$, $R^{205}$ and $R^{206}$ may be identical to or different from each other and each represent an alkyl group having 1 to 20 carbon atoms.

With respect to the above alkyl group, as a preferred substituted alkyl group, there can be mentioned an aminoalkyl group having 1 to 20 carbon atoms, a hydroxyalkyl group having 1 to 20 carbon atoms or a cyanoalkyl group having 1 to 20 carbon atoms.

More preferably, in these general formulae (A) and (E) the alkyl group is unsubstituted.

As preferred compounds, there can be mentioned guanidine, aminopyrrolidine, pyrazole, pyrazoline, piperazine, aminomorpholine, aminoalkylmorpholine, piperidine and the like. Further, as preferred compounds, there can be mentioned compounds with an imidazole structure, a diazabicyclo structure, an onium hydroxide structure, an onium carboxylate structure, a trialkylamine structure, an aniline structure or a pyridine structure, alkylamine derivatives having a hydroxyl group and/or an ether bond, aniline derivatives having a hydroxyl group and/or an ether bond and the like.

As the compounds with an imidazole structure, there can be mentioned imidazole, 2,4,5-triphenylimidazole, benzimidazole, 2-phenylbenzoimidazole and the like. As the compounds with a diazabicyclo structure, there can be mentioned 1,4-diazabicyclo[2,2,2]octane, 1,5-diazabicyclo[4,3,0]non-5-ene, 1,8-diazabicyclo[5,4,0]undec-7-ene and the like. As the compounds with an onium hydroxide structure, there can be mentioned tetrabutylammonium hydroxide, a triarylsulfonium hydroxide, phenacylsulfonium hydroxide, and sulfonium hydroxides having a 2-oxoalkyl group such as triphenylsulfonium hydroxide, tris(t-butylphenyl)sulfonium hydroxide, bis(t-butylphenyl)iodonium hydroxide, phenacylthiophenium hydroxide, 2-oxopropylthiophenium hydroxide and the like. As the compounds with an onium carboxylate structure, there can be mentioned those having a carboxylate at the anion moiety of the compounds with an onium hydroxide structure, for example, an acetate, adamantane-1-carboxylate, a perfluoroalkyl carboxylate and the like. As the compounds with a trialkylamine structure, there can be mentioned tri(n-butyl)amine, tri(n-octyl)amine and the like.

As the aniline compounds, there can be mentioned 2,6-diisopropylaniline, N,N-dimethylaniline, N,N-dibutylaniline, N,N-dihexylaniline and the like. As the alkylamine derivatives having a hydroxyl group and/or an ether bond, there can be mentioned ethanolamine, diethanolamine, triethanolamine, N-phenyldiethanolamine, tris(methoxyethoxyethyl) amine and the like. As the aniline derivatives having a hydroxyl group and/or an ether bond, there can be mentioned N,N-bis(hydroxyethyl)aniline and the like.

As preferred basic compounds, there can be further mentioned an amine compound having a phenoxy group, an ammonium salt compound having a phenoxy group, an amine compound having a sulfonic ester group and an ammonium salt compound having a sulfonic ester group.

As the amine compound, use can be made of primary, secondary and tertiary amine compounds. An amine compound having its at least one alkyl group bonded to the nitrogen atom thereof is preferred. Among the amine compounds, a tertiary amine compound is more preferred. Of the amine compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. Of the amine compounds, it is preferred for the alkyl chain to contain an oxygen atom so as to form an oxyalkylene group. The number of oxyalkylene groups in each molecule is one or more, preferably 3 to 9 and more preferably 4 to 6. The oxyalkylene group is preferably an oxyethylene group ($—CH_2CH_2O—$) or an oxypropylene group ($—CH(CH_3)CH_2O—$ or $—CH_2CH_2CH_2O—$), more preferably an oxyethylene group.

As the ammonium salt compound, use can be made of primary, secondary, tertiary and quaternary ammonium salt compounds. An ammonium salt compound having its at least one alkyl group bonded to the nitrogen atom thereof is preferred. Of the ammonium salt compounds, as long as at least one alkyl group (preferably having 1 to 20 carbon atoms) is bonded to the nitrogen atom, a cycloalkyl group (preferably having 3 to 20 carbon atoms) or an aryl group (preferably having 6 to 12 carbon atoms) besides the alkyl group may be bonded to the nitrogen atom. Of the ammonium salt compounds, it is preferred for the alkyl chain to contain an oxygen atom so as to form an oxyalkylene group. The number of oxyalkylene groups in each molecule is one or more, preferably 3 to 9 and more preferably 4 to 6. The oxyalkylene group is preferably an oxyethylene group ($—CH_2CH_2O—$) or an oxypropylene group ($—CH(CH_3)CH_2O—$ or $—CH_2CH_2CH_2O—$), more preferably an oxyethylene group. As the anion of the ammonium salt compounds, there can be mentioned a halogen atom, a sulfonate, a borate, a phosphate or the like. Of these, a halogen atom and a sulfonate are preferred. Among halogen atoms, chloride, bromide and iodide are especially preferred. Among sulfonates, an organic sulfonate having 1 to 20 carbon atoms is especially preferred. As the organic sulfonate, there can be mentioned an aryl sulfonate and an alkyl sulfonate having 1 to 20 carbon atoms. The alkyl group of the alkyl sulfonate may have a substituent. As the substituent, there can be mentioned, for example, fluorine, chlorine, bromine, an alkoxy group, an acyl group, an aryl group or the like. As specific examples of the alkyl sulfonates, there can be mentioned methane sulfonate, ethane sulfonate, butane sulfonate, hexane sulfonate, octane sulfonate, benzyl sulfonate, trifluoromethane sulfonate, pentafluoroethane sulfonate, nonafluorobutane sulfonate and the like. As the aryl group of the aryl sulfonate, there can be mentioned a benzene ring, a naphthalene ring or an anthracene ring. The benzene ring, naphthalene ring or anthracene ring may have a substituent. As preferred substituents, there can be mentioned a linear or branched alkyl group having 1 to 6 carbon atoms and a cycloalkyl group having 3 to 6 carbon atoms. As specific examples of the linear or branched alkyl groups and cycloalkyl groups, there can be mentioned methyl, ethyl, n-propyl, isopropyl, n-butyl, i-butyl, t-butyl, n-hexyl, cyclohexyl and the like. As other substituents, there can be mentioned an alkoxy group having 1 to 6 carbon atoms, a halogen atom, cyano, nitro, an acyl group, an acyloxy group and the like.

The amine compound having a phenoxy group and ammonium salt compound having a phenoxy group are those having a phenoxy group at the end of the alkyl group of the amine compound or ammonium salt compound opposed to the nitrogen atom. The phenoxy group may have a substituent. As the substituent of the phenoxy group, there can be mentioned, for example, an alkyl group, an alkoxy group, a halogen atom, a cyano group, a nitro group, a carboxyl group, a carboxylic ester group, a sulfonic ester group, an aryl group, an aralkyl group, an acyloxy group, an aryloxy group or the like. The substitution position of the substituent may be any of 2- to 6-positions. The number of substituents is optional within the range of 1 to 5.

It is preferred that at least one oxyalkylene group exist between the phenoxy group and the nitrogen atom. The number of oxyalkylene groups in each molecule is one or more, preferably 3 to 9 and more preferably 4 to 6. The oxyalkylene group is preferably an oxyethylene group ($—CH_2CH_2O—$) or an oxypropylene group ($—CH(CH_3)CH_2O—$ or $—CH_2CH_2CH_2O—$), more preferably an oxyethylene group.

The sulfonic ester group of the amine compound having a sulfonic ester group or ammonium salt compound having a sulfonic ester group may be any of an alkylsulfonic ester, a cycloalkylsulfonic ester and an arylsulfonic ester. In the alkylsulfonic ester, the alkyl group preferably has 1 to 20 carbon atoms. In the cycloalkylsulfonic ester, the cycloalkyl group preferably has 3 to 20 carbon atoms. In the arylsulfonic ester, the aryl group preferably has 6 to 12 carbon atoms. The alkylsulfonic ester, cycloalkylsulfonic ester and arylsulfonic ester may have substituents. As preferred substituents, there can be mentioned a halogen atom, a cyano group, a nitro group, a carboxyl group, a carboxylic ester group and a sulfonic ester group.

It is preferred for at least one oxyalkylene group to exist between the sulfonic ester group and the nitrogen atom. The number of oxyalkylene groups in each molecule is one or more, preferably 3 to 9 and more preferably 4 to 6. The oxyalkylene group is preferably an oxyethylene group ($—CH_2CH_2O—$) or an oxypropylene group ($—CH(CH_3)CH_2O—$ or $—CH_2CH_2CH_2O—$), more preferably an oxyethylene group.

These basic compounds are used either individually or in combination.

The amount of basic compound used is generally in the range of 0.001 to 10 mass %, preferably 0.01 to 5 mass % based on the solid content of the photosensitive composition.

With respect to the ratio of the acid generator to basic compound used in the composition, preferably, the acid generator/basic compound (molar ratio)=1.0 to 300. The reason for this is that the molar ratio is preferred to be 1.0 or higher from the viewpoint of sensitivity and resolving power. The molar ratio is preferred to be 300 or below from the viewpoint of the inhibition of any resolving power deterioration due to thickening of resist pattern over time from exposure to a heating treatment. The acid generator/basic compound (molar ratio) is more preferably in the range of 1.5 to 200, still more preferably 2.0 to 150.

The carboxylic acid onium salt will be described below.

As the carboxylic acid onium salt, there can be mentioned a carboxylic acid sulfonium salt, a carboxylic acid iodonium salt, a carboxylic acid ammonium salt or the like. The especially preferred carboxylic acid onium salts are the iodonium salt and the sulfonium salt. It is preferred for the carboxylate residue of the carboxylic acid onium salt for use in the present invention to be one containing neither an aromatic group nor a carbon-carbon double bond. The especially preferred anion moiety thereof is a linear, or branched, or monocyclic, or polycyclic alkyl carboxylate anion, whose alkyl moiety has 1 to 30 carbon atoms. A more preferred anion moiety is an anion of carboxylic acid wherein the alkyl group is partially or wholly fluorinated. The alkyl chain may contain an oxygen atom. Accordingly, there would be achieved securement of the transparency in 220 nm or shorter light, enhancement of the sensitivity and resolving power and improvement of the dependency on density distribution and exposure margin.

As the fluorinated carboxylic acid anion, there can be mentioned any of the anions of fluoroacetic acid, difluoroacetic acid, trifluoroacetic acid, pentafluoropropionic acid, heptafluorobutyric acid, nonafluoropentanoic acid, perfluorododecanoic acid, perfluorotridecanoic acid, perfluorocyclohexanecarboxylic acid and 2,2-bistrifluoromethylpropionic acid, or the like.

These carboxylic acid onium salts can be synthesized by reacting a sulfonium hydroxide, an iodonium hydroxide or an ammonium hydroxide and a carboxylic acid with silver oxide in an appropriate solvent.

The content of each carboxylic acid onium salt in the composition is generally in the range of 0.1 to 20 mass %, preferably 0.5 to 10 mass % and more preferably 1 to 7 mass % based on the total solids of the composition.

6. Surfactant

The photosensitive composition of the present invention preferably further contains a surfactant, and more preferably contains any one, or two or more members, of fluorinated and/or siliconized surfactants (fluorinated surfactant, siliconized surfactant and surfactant containing both fluorine and silicon atoms).

The photosensitive composition of the present invention when containing the above surfactant would, in the use of an exposure light source of 250 nm or below, especially 220 nm or below, realize favorable sensitivity and resolving power and produce a resist pattern with less adhesion and development defects.

As the fluorinated and/or siliconized surfactants, there can be mentioned, for example, those described in JP-A's-62-36663, 61-226746, 61-226745, 62-170950, 63-34540, 7-230165, 8-62834, 9-54432, 9-5988 and 2002-277862 and U.S. Pat. Nos. 5,405,720, 5,360,692, 5,529,881, 5,296,330, 5,436,098, 5,576,143, 5,294,511 and 5,824,451. Any of the following commercially available surfactants can be used as is.

As useful commercially available surfactants, there can be mentioned, for example, fluorinated surfactants/siliconized surfactants, such as Eftop EF301 and EF303 (produced by Shin-Akita Kasei Co., Ltd.), Florad FC 430, 431 and 4430 (produced by Sumitomo 3M Ltd.), Megafac F171, F173, F176, F189, F113, F110, F177, F120 and R08 (produced by Dainippon Ink & Chemicals, Inc.), Surflon S-382, SC101, 102, 103, 104, 105 and 106 (produced by Asahi Glass Co., Ltd.), Troy Sol S-366 (produced by Troy Chemical Co., Ltd.), GF-300 and GF-150 (produced by TOAGOSEI CO., LTD.), Sarfron S-393 (produced by SEIMI CHEMICAL CO., LTD.), Eftop EF121, EF122A, EF122B, RF122C, EF125M, EF135M, EF351, EF352, EF801, EF802 and EF601 (produced by JEMCO INC.), PF636, PF656, PF6320 and PF6520 (produced by OMNOVA), and FTX-204G, 208G, 218G, 230G, 204D, 208D, 212D, 218D and 222D (produced by NEOS). Further, polysiloxane polymer KP-341 (produced by Shin-Etsu Chemical Co., Ltd.) can be employed as the siliconized surfactant.

As the surfactant, besides the above publicly known surfactants, use can be made of a surfactant based on a polymer having a fluorinated aliphatic group derived from a fluorinated aliphatic compound, produced by a telomerization technique (also called a telomer process) or an oligomerization technique (also called an oligomer process). The fluorinated aliphatic compound can be synthesized by the process described in JP-A-2002-90991.

The polymer having a fluorinated aliphatic group is preferably a copolymer from a monomer having a fluorinated aliphatic group and a poly(oxyalkylene) acrylate and/or poly(oxyalkylene) methacrylate, which copolymer may have an irregular distribution or may result from block copolymerization. As the poly(oxyalkylene) group, there can be mentioned a poly(oxyethylene) group, a poly(oxypropylene) group, a poly(oxybutylene) group or the like. Further, use can be made of a unit having alkylene groups of different chain lengths in a single chain, such as poly(oxyethylene-oxypropylene-oxyethylene block concatenation) or poly(oxyethylene-oxypropylene block concatenation). Moreover, the copolymer from a monomer having a fluorinated aliphatic group and a poly(oxyalkylene) acrylate (or methacrylate) is not limited to two-monomer copolymers and may be a three or more monomer copolymer obtained by simultaneous copolymerization of two or more different monomers having a fluorinated aliphatic group, two or more different poly(oxyalkylene) acrylates (or methacrylates), etc.

For example, as such a surfactant which is commercially available, there can be mentioned Megafac F178, F-470, F-473, F-475, F-476 or F-472 (produced by Dainippon Ink & Chemicals, Inc.). Further, there can be mentioned a copolymer from an acrylate (or methacrylate) having a $C_6F_{13}$ group and a poly(oxyalkylene) acrylate (or methacrylate), a copolymer from an acrylate (or methacrylate) having a $C_3F_7$ group, poly(oxyethylene) acrylate (or methacrylate) and poly(oxypropylene) acrylate (or methacrylate), or the like.

In the present invention, surfactants other than the fluorinated and/or siliconized surfactants can also be employed. In particular, there can be mentioned, for example, nonionic surfactants including a polyoxyethylene alkyl ether such as polyoxyethylene lauryl ether, polyoxyethylene stearyl ether, polyoxyethylene cetyl ether or polyoxyethylene oleyl ether, a polyoxyethylene alkylaryl ether such as polyoxyethylene octylphenol ether or polyoxyethylene nonylphenol ether, a polyoxyethylene-polyoxypropylene block copolymer, a sorbitan fatty acid ester such as sorbitan monolaurate, sorbitan monopalmitate, sorbitan monostearate, sorbitan monooleate, sorbitan trioleate or sorbitan tristearate, a polyoxyethylene sorbitan fatty acid ester such as polyoxyethylene sorbitan monolaurate, polyoxyethylene sorbitan monopalmitate, polyoxyethylene sorbitan monostearate, polyoxyethylene sorbitan trioleate or polyoxyethylene sorbitan tristearate, or the like.

These surfactants may be used either individually or in combination.

The amount of each surfactant used is preferably in the range of 0 to 2 mass %, more preferably 0.0001 to 2 mass %, and still more preferably 0.0005 to 1 mass % based on the total mass of the photosensitive composition (excluding the solvent).

7. Dissolution Inhibiting Compound

The photosensitive composition of the present invention may contain a dissolution inhibiting compound of 3000 or less molecular weight that is decomposed by the action of an acid to thereby increase the solubility in an alkali developer (hereinafter also referred to as "dissolution inhibiting compound").

From the viewpoint of preventing any lowering of 220 nm or shorter transmission, the dissolution inhibiting compound is preferably an alicyclic or aliphatic compound having an acid-decomposable group, such as any of cholic acid derivatives having an acid-decomposable group described in Proceeding of SPIE, 2724, 355 (1996). The acid-decomposable group and alicyclic structure are the same as described with respect to the resin as the component (A).

When the actinic ray-sensitive or radiation-sensitive resin composition of the present invention is exposed to a KrF excimer laser or irradiated with electron beams, preferred use is made of one having a structure resulting from substitution of the phenolic hydroxyl group of a phenol compound with an acid-decomposable group. The phenol compound preferably contains 1 to 9 phenol skeletons, more preferably 2 to 6 phenol skeletons.

In the present invention, the molecular weight of each dissolution inhibiting compound is 3000 or less, preferably 300 to 3000 and more preferably 500 to 2500.

The amount of dissolution inhibiting compound added is preferably in the range of 3 to 50 mass %, more preferably 5 to 40 mass % based on the total solids of the actinic ray-sensitive or radiation-sensitive resin composition.

Specific examples of the dissolution inhibiting compounds will be shown below, which however in no way limit the scope of the present invention.

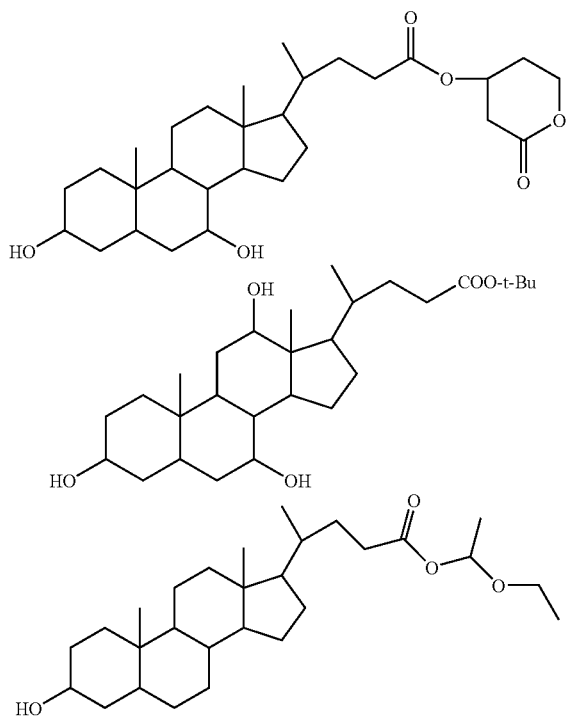

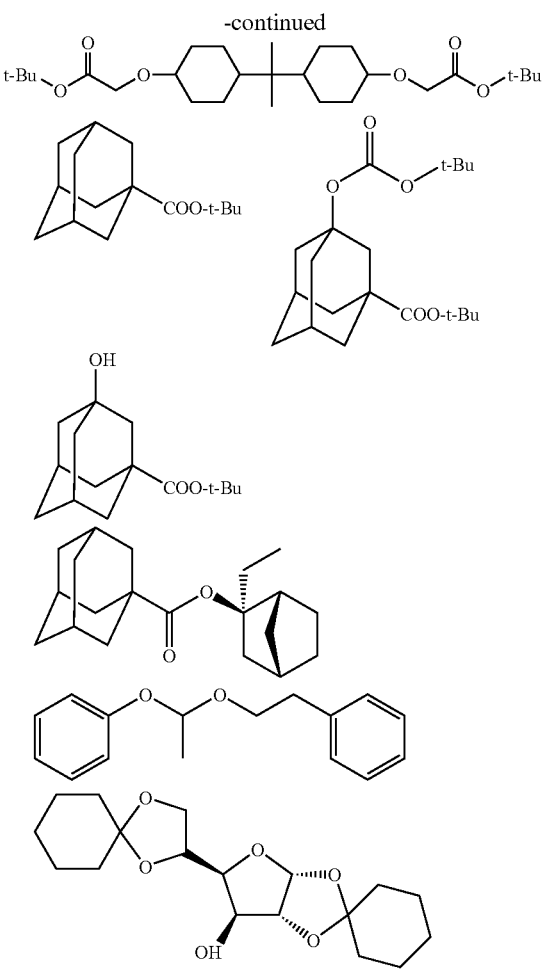

-continued

8. Other Additives

The actinic ray-sensitive or radiation-sensitive resin composition of the present invention may further according to necessity contain a dye, a plasticizer, a photosensitizer, a light absorber, a compound capable of increasing the solubility in a developer (for example, a phenolic compound of 1000 or less molecular weight or a carboxylated alicyclic or aliphatic compound), etc.

The above phenolic compound of 1000 or less molecular weight can be easily synthesized by persons of ordinary skill in the art to which the present invention pertains while consulting the processes described in, for example, JP-As 4-122938 and 2-28531, U.S. Pat. No. 4,916,210 and EP 219294.

As the carboxylated alicyclic or aliphatic compound, there can be mentioned, for example, a carboxylic acid derivative of steroid structure such as cholic acid, deoxycholic acid or lithocholic acid, an adamantanecarboxylic acid derivative, adamantanedicarboxylic acid, cyclohexanecarboxylic acid, cyclohexanedicarboxylic acid or the like. These are however nonlimiting.

[Method of Forming Pattern]

From the viewpoint of enhancement of resolving power, it is preferred for the actinic ray-sensitive or radiation-sensitive resin composition of the present invention to be used with a coating thickness of 10 to 500 nm. More preferably, the actinic ray-sensitive or radiation-sensitive resin composition is used with a coating thickness of 20 to 300 nm. This coating thickness can be attained by setting the solid content of the photosensitive composition within an appropriate range so as to cause the composition to have an appropriate viscosity, thereby improving the applicability and film forming property.

The total solids content of the actinic ray-sensitive or radiation-sensitive resin composition is generally in the range of 1 to 20 mass %, preferably 1 to 15 mass % and more preferably 1 to 10 mass %.

The actinic ray-sensitive or radiation-sensitive resin composition of the present invention is used in such a manner that the above components are dissolved in a given organic solvent, preferably the above mixed solvent, and filtered and applied onto a given support in the following manner. The filter medium for the filtration preferably consists of a polytetrafluoroethylene, polyethylene or nylon having a pore size of 0.1 µm or less, especially 0.05 µm or less and more especially 0.03 µm or less.

For example, an actinic ray-sensitive or radiation-sensitive resin composition is applied onto a substrate, such as one for use in the production of precision integrated circuit elements (e.g., silicon/silicon dioxide coating), by appropriate application means, such as a spinner or coater, and dried to thereby form a film.

The film is exposed through a given mask to actinic rays or radiation, preferably baked (heated), and developed and rinsed. Accordingly, a desirable pattern can be obtained.

As the actinic rays or radiation, there can be mentioned infrared rays, visible light, ultraviolet rays, far ultraviolet rays, extreme ultraviolet rays, X-rays, electron beams or the like. Without dependence upon the type of light source employed, a pattern improved in the exposure latitude, LWR and pattern collapse performance can be obtained from the photosensitive composition of the present invention. As practical actinic rays or radiation, use is made of far ultraviolet rays of preferably 250 nm or less, more preferably 220 nm or less and especially preferably 1 to 200 nm wavelength, such as a KrF excimer laser (248 nm), an ArF excimer laser (193 nm) and an F2 excimer laser (157 nm), as well as X-rays, electron beams and the like. Preferred use is made of an ArF excimer laser, an $F_2$ excimer laser, EUV (13 nm) and electron beams.

Prior to the formation of a film, the substrate may be coated with an antireflection film.

As the antireflection film, use can be made of not only an inorganic film of titanium, titanium oxide, titanium nitride, chromium oxide, carbon, amorphous silicon or the like but also an organic film composed of a light absorber and a polymer material. Also, as the organic antireflection film, use can be made of commercially available organic antireflection films, such as the DUV30 Series and DUV40 Series produced by Brewer Science Inc. and AR-2, AR-3 and AR-5 produced by Shipley Co., Ltd.

In the development step, an alkali developer is used as follows. As the alkali developer for a positive resist composition, use can be made of any of alkaline aqueous solutions of an inorganic alkali such as sodium hydroxide, potassium hydroxide, sodium carbonate, sodium silicate, sodium metasilicate or aqueous ammonia, a primary amine such as ethylamine or n-propylamine, a secondary amine such as diethylamine or di-n-butylamine, a tertiary amine such as triethylamine or methyldiethylamine, an alcoholamine such as dimethylethanolamine or triethanolamine, a quaternary ammonium salt such as tetramethylammonium hydroxide or tetraethylammonium hydroxide, a cycloamine such as pyrrole or piperidine, or the like.

Before the use of the above alkali developer, appropriate amounts of an alcohol and a surfactant may be added thereto.

The alkali concentration of the alkali developer is generally in the range of 0.1 to 20 mass %.

The pH value of the alkali developer is generally in the range of 10.0 to 15.0.

Before the use of the above alkaline aqueous solution, appropriate amounts of an alcohol and a surfactant may be added thereto.

Pure water can be used as the rinse liquid. Before the use, an appropriate amount of surfactant may be added thereto.

The development operation or rinse operation may be followed by the operation for removing any developer or rinse liquid adhering onto the pattern by the use of a supercritical fluid.

At the time of irradiation with actinic rays or radiation, exposure (liquid immersion exposure) may be carried out after filling the interstice between film and lens with a liquid (liquid immersion medium, liquid for liquid immersion) of refractive index higher than that of air. This would bring about an enhancement of resolving power. Any liquid with a refractive index higher than that of air can be employed as the liquid immersion medium. Preferably, pure water is employed.

The liquid for liquid immersion for use in the liquid immersion exposure will now be described.

The liquid for liquid immersion preferably consists of a liquid being transparent in exposure wavelength whose temperature coefficient of refractive index is as low as possible so as to ensure minimization of any distortion of optical image projected on the film. Especially in the use of an ArF excimer laser (wavelength: 193 nm) as an exposure light source, however, it is more preferred to use water from not only the above viewpoints but also the viewpoints of easy procurement and easy handling.

Further, from the viewpoint of refractive index increase, use can be made of a medium of 1.5 or higher refractive index. Such a medium may be an aqueous solution or an organic solvent.

In the use of water as a liquid for liquid immersion, a slight proportion of additive (liquid) that would not dissolve the resist film on a wafer and would be negligible with respect to its influence on an optical coat for an under surface of lens element may be added in order to not only decrease the surface tension of water but also increase a surface activating power. The additive is preferably an aliphatic alcohol with a refractive index approximately equal to that of water, for example, methyl alcohol, ethyl alcohol, isopropyl alcohol or the like. The addition of an alcohol with a refractive index approximately equal to that of water is advantageous in that even when the alcohol component is evaporated from water to thereby cause a change of content concentration, the change of refractive index of the liquid as a whole can be minimized. On the other hand, when a substance being opaque in 193 nm rays or an impurity whose refractive index is greatly different from that of water is mixed therein, the mixing would invite a distortion of optical image projected on the resist film. Accordingly, it is preferred to use distilled water as the liquid immersion water. Furthermore, use may be made of pure water having been filtered through an ion exchange filter or the like.

Desirably, the electrical resistance of the water is 18.3 MΩcm or higher, and the TOC (organic matter concentration) thereof is 20 ppb or below. Prior deaeration of the water is desired.

Raising the refractive index of the liquid for liquid immersion would enable an enhancement of lithography performance. From this viewpoint, an additive suitable for refractive index increase may be added to the water, or heavy water ($D_2O$) may be used in place of water.

In the exposure of the film of the actinic ray-sensitive or radiation-sensitive resin composition of the present invention via the liquid immersion medium, a hydrophobic resin (HR) may be further added according to necessity. This would bring about uneven localization of the hydrophobic resin (HR) on the surface layer of the resist film. When the liquid immersion medium is water, there would be attained an improvement of receding contact angle on the surface of the film with reference to water upon formation of the film, and accordingly an enhancement of the liquid immersion water tracking property. Although the hydrophobic resin (HR) is not particularly limited as long as an improvement of receding contact angle on the surface is realized by the addition thereof, it is preferred to employ a resin having at least either a fluorine atom or a silicon atom. The receding contact angle of the film is preferably in the range of 60° to 90°, more preferably 70° or higher. The amount of resin added can be appropriately regulated so that the receding contact angle of the film falls within the above range. However, the addition amount is preferably in the range of 0.1 to 10 mass %, more preferably 0.1 to 5 mass % based on the total solids of the composition. Although the hydrophobic resin (HR) is unevenly localized on the interface as aforementioned, differing from the surfactant, the hydrophobic resin does not necessarily have to have a hydrophilic group in its molecule and does not need to contribute toward uniform mixing of polar/nonpolar substances.

The receding contact angle refers to a contact angle determined when the contact line at a droplet-substrate interface draws back. It is generally known that the receding contact angle is useful in the simulation of droplet mobility in a dynamic condition. In a simple definition, the receding contact angle can be defined as the contact angle exhibited at the recession of the droplet interface at the time of, after application of a droplet discharged from a needle tip onto a substrate, re-indrawing the droplet into the needle. Generally, the receding contact angle can be measured according to a method of contact angle measurement known as the dilation/contraction method.

In the operation of liquid immersion exposure, it is needed for the liquid for liquid immersion to move on a wafer while tracking the movement of an exposure head involving high-speed scanning on the wafer and thus forming an exposure pattern. Therefore, the contact angle of the liquid for liquid immersion with respect to the resist film in dynamic condition is important, and it is required for the resist to be capable of tracking the high-speed scanning of the exposure head without leaving any droplets.

The fluorine atom or silicon atom of the hydrophobic resin (HR) may be present in the principal chain of the resin or may be a substituent on the side chain thereof.

The hydrophobic resin (HR) is preferably a resin having an alkyl group containing a fluorine atom, a cycloalkyl group containing a fluorine atom or an aryl group containing a fluorine atom as a partial structure containing a fluorine atom.

The alkyl group containing a fluorine atom (preferably having 1 to 10 carbon atoms, more preferably 1 to 4 carbon atoms) is a linear or branched alkyl group having at least one hydrogen atom thereof substituted with a fluorine atom. Further, other substituents may be possessed.

The cycloalkyl group containing a fluorine atom is a monocyclic or polycyclic alkyl group having at least one hydrogen atom thereof substituted with a fluorine atom. Further, other substituents may be contained.

As the aryl group containing a fluorine atom, there can be mentioned one having at least one hydrogen atom of an aryl group, such as a phenyl or naphthyl group, substituted with a fluorine atom. Further, other substituents may be contained.

As preferred alkyl groups containing a fluorine atom, cycloalkyl groups containing a fluorine atom and aryl groups containing a fluorine atom, there can be mentioned groups of the following general formulae (F2) to (F4), which however in no way limit the scope of the present invention.

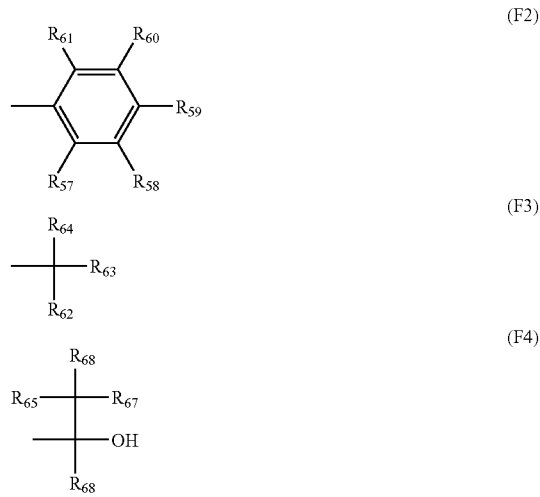

In the general formulae (F2) to (F4), each of $R_{57}$ to $R_{68}$ independently represents a hydrogen atom, a fluorine atom or an alkyl group, provided that at least one of each of $R_{57}$-$R_{61}$, $R_{62}$-$R_{64}$ and $R_{65}$-$R_{68}$ represents a fluorine atom or an alkyl group (preferably having 1 to 4 carbon atoms) having at least one hydrogen atom thereof substituted with a fluorine atom. It is preferred that all of $R_{57}$-$R_{61}$ and $R_{65}$-$R_{67}$ represent fluorine atoms. Each of $R_{62}$, $R_{63}$ and $R_{68}$ preferably represents an alkyl group (especially having 1 to 4 carbon atoms) having at least one hydrogen atom thereof substituted with a fluorine atom, more preferably a perfluoroalkyl group having 1 to 4 carbon atoms. $R_{62}$ and $R_{63}$ may be bonded with each other to thereby form a ring.

Specific examples of the groups of the general formula (F2) include a p-fluorophenyl group, a pentafluorophenyl group, a 3,5-di(trifluoromethyl)phenyl group and the like.

Specific examples of the groups of the general formula (F3) include a trifluoromethyl group, a pentafluoropropyl group, a pentafluoroethyl group, a heptafluorobutyl group, a hexafluoroisopropyl group, a heptafluoroisopropyl group, a hexafluoro(2-methyl)isopropyl group, a nonafluorobutyl group, an octafluoroisobutyl group, a nonafluorohexyl group, a nonafluoro-t-butyl group, a perfluoroisopentyl group, a perfluorooctyl group, a perfluoro(trimethyl)hexyl group, a 2,2,3,3-tetrafluorocyclobutyl group, a perfluorocyclohexyl group and the like. Of these, a hexafluoroisopropyl group, a heptafluoroisopropyl group, a hexafluoro(2-methyl)isopropyl group, an octafluoroisobutyl group, a nonafluoro-t-butyl group and a perfluoroisopentyl group are preferred. A hexafluoroisopropyl group and a heptafluoroisopropyl group are more preferred.

Specific examples of the groups of the general formula (F4) include —C(CF$_3$)$_2$OH, —C(C$_2$F$_5$)$_2$OH, —C(CF$_3$)(CF$_3$)OH, —CH(CF$_3$)OH and the like. —C(CF$_3$)$_2$OH is preferred.

Specific examples of the repeating units having a fluorine atom will be shown below, which however in no way limit the scope of the present invention.

In the specific examples, $X_1$ represents a hydrogen atom, —$CH_3$, —F or —$CF_3$.
$X_2$ represents —F or —$CF_3$.
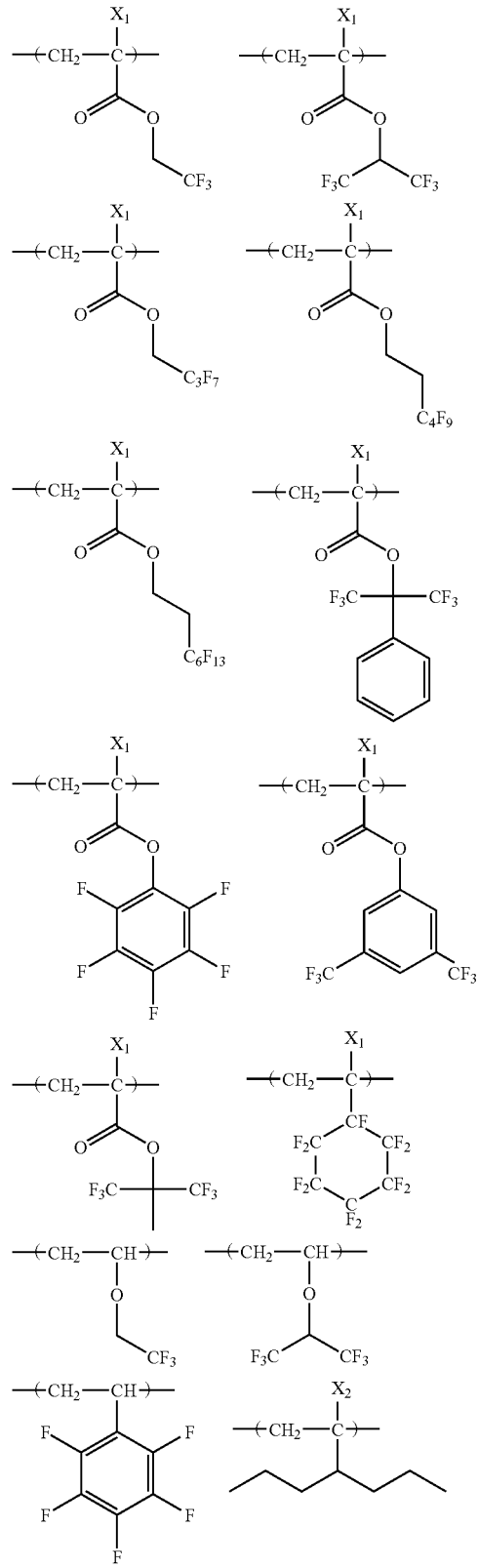
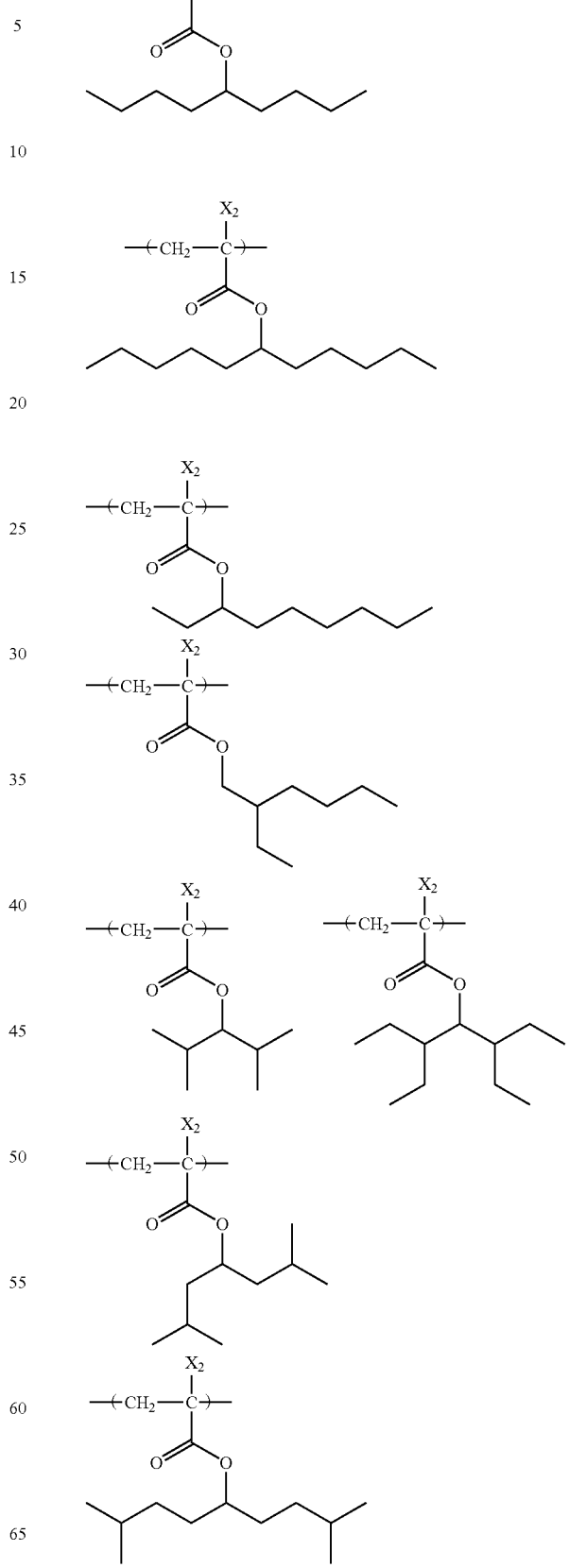

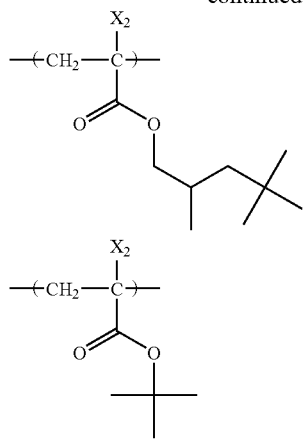

The hydrophobic resin (HR) may contain a silicon atom. The hydrophobic resin (HR) is preferably a resin having an alkylsilyl structure (preferably a trialkylsilyl group) or a cyclosiloxane structure as a partial structure having a silicon atom.

As the alkylsilyl structure or cyclosiloxane structure, there can be mentioned, for example, any of the groups of the following general formulae (CS-1) to (CS-3) or the like.

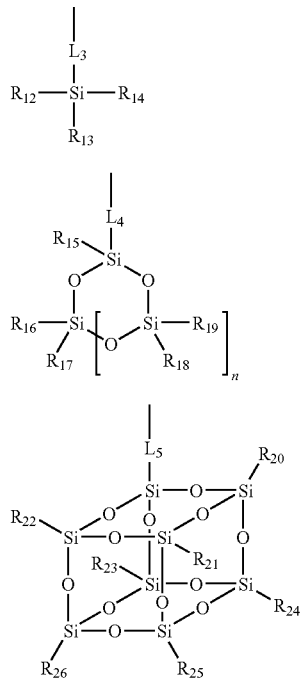

In the general formulae (CS-1) to (CS-3), each of $R_{12}$ to $R_{26}$ independently represents a linear or branched alkyl group (preferably having 1 to 20 carbon atoms) or a cycloalkyl group (preferably having 3 to 20 carbon atoms).

Each of $L_3$ to $L_5$ represents a single bond or a bivalent connecting group. As the bivalent connecting group, there can be mentioned any one or a combination of two or more groups selected from the group consisting of an alkylene group, a phenylene group, an ether group, a thioether group, a carbonyl group, an ester group, an amido group, a urethane group and a urea group.

In the formulae, n is an integer of 1 to 5.

Specific examples of the repeating units having the groups of the general formulae (CS-1) to (CS-3) will be shown below, which however in no way limit the scope of the present invention.

In the specific examples, $X_1$ represents a hydrogen atom, —$CH_3$, —F or —$CF_3$.

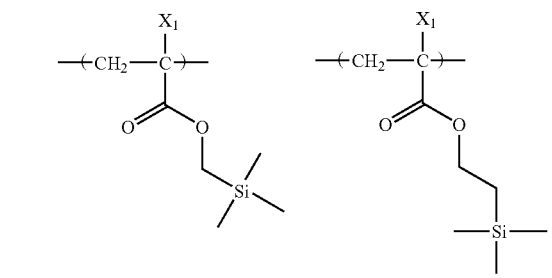

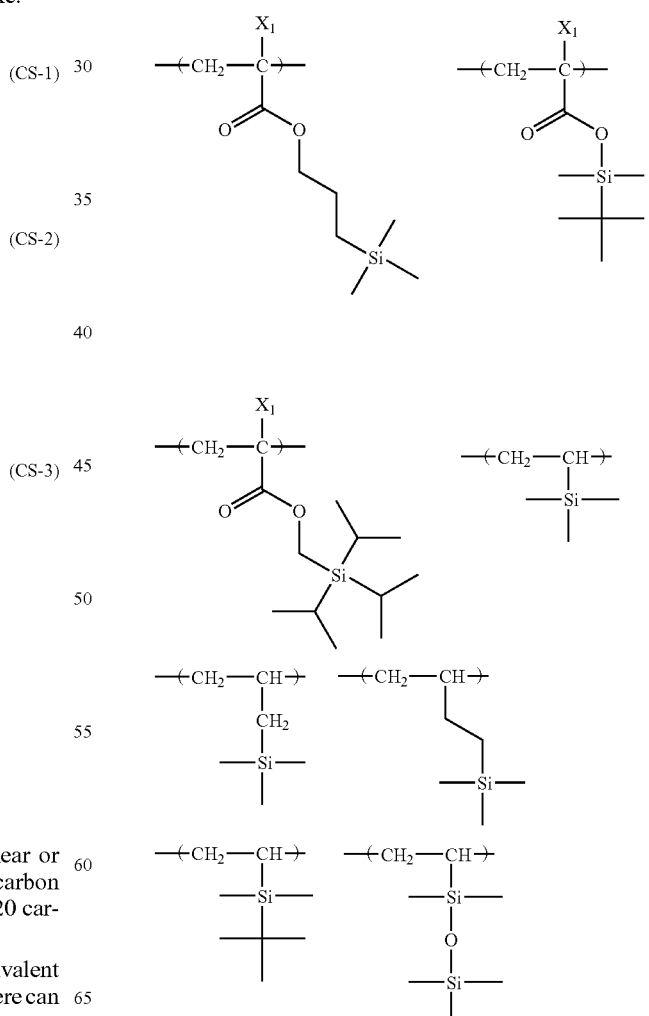

-continued

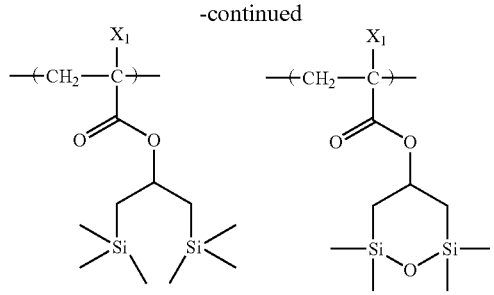

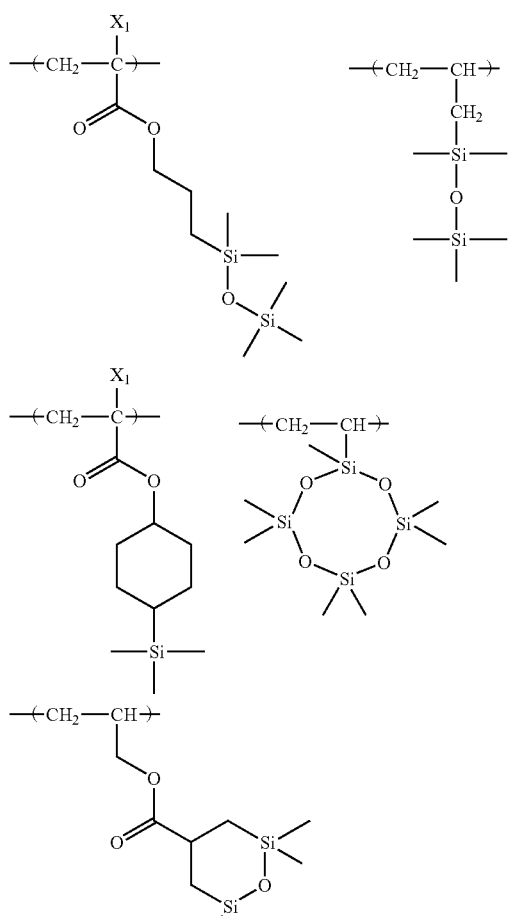

R = CH$_3$, C$_2$H$_5$, C$_3$H$_7$, C$_4$H$_9$

-continued

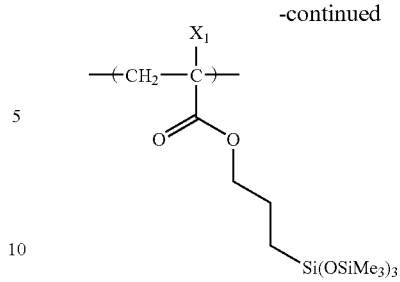

Moreover, the hydrophobic resin (HR) may have at least one group selected from among the following groups (x) to (z):

(x) an alkali soluble group, (y) a group that is decomposed by the action of an alkali developer, resulting in an increase of solubility in the alkali developer, and (z) a group that is decomposed by the action of an acid.

As the alkali soluble group (x), there can be mentioned a phenolic hydroxyl group, a carboxylate group, a fluoroalcohol group, a sulfonate group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, a tris(alkylsulfonyl)methylene group or the like.

As preferred alkali soluble groups, there can be mentioned a fluoroalcohol group (preferably hexafluoroisopropanol), a sulfonimido group and a bis(carbonyl)methylene group.

As the repeating unit having an alkali soluble group (x), preferred use is made of any of a repeating unit resulting from direct bonding of an alkali soluble group to the principal chain of a resin like a repeating unit of acrylic acid or methacrylic acid, a repeating unit resulting from bonding, via a connecting group, of an alkali soluble group to the principal chain of a resin and a repeating unit resulting from polymerization with the use of a chain transfer agent or polymerization initiator having an alkali soluble group to thereby introduce the same in a polymer chain terminal.

The content of repeating units having an alkali soluble group (x) is preferably in the range of 1 to 50 mol %, more preferably 3 to 35 mol % and still more preferably 5 to 20 mol % based on all the repeating units of the polymer.

Specific examples of the repeating units having an alkali soluble group (x) will be shown below, which however in no way limit the scope of the present invention.

In the formulae, R represents H, CH$_3$, CF$_3$ or CH$_2$OH.

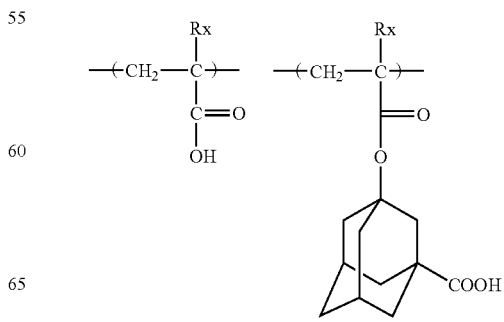

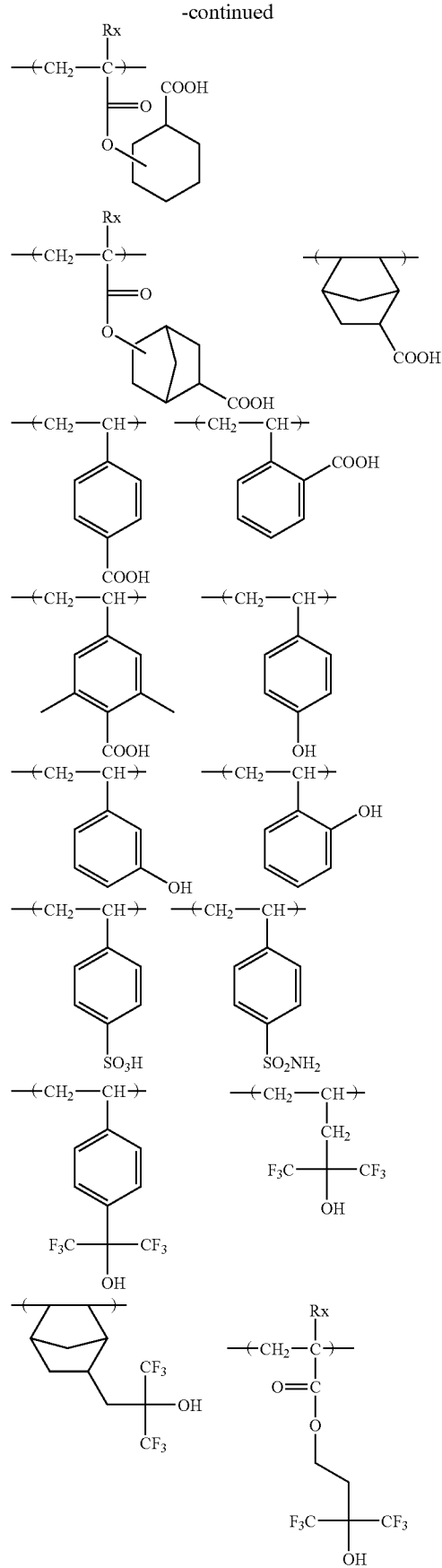
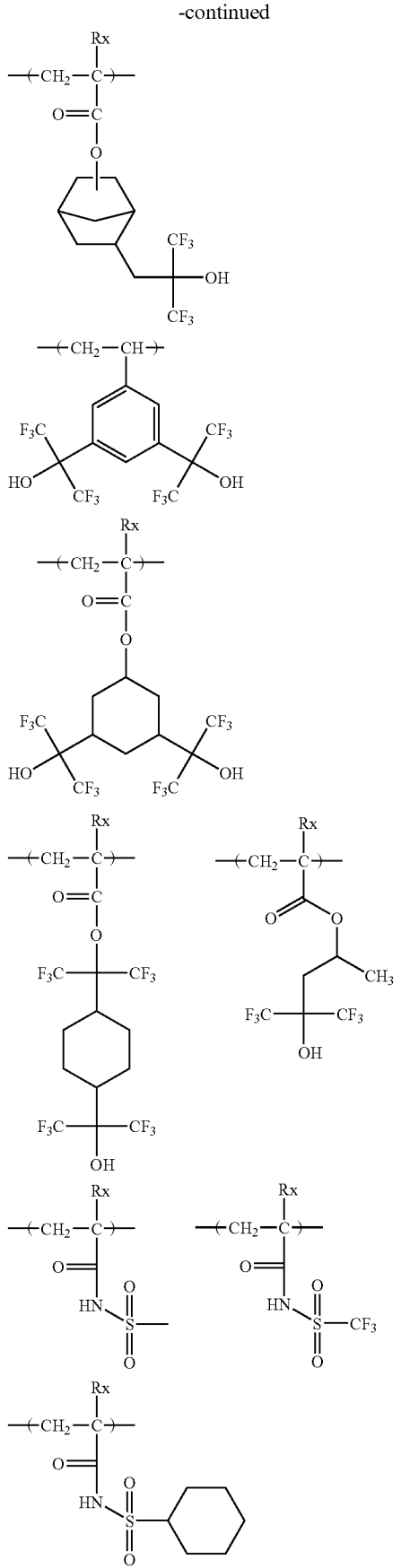

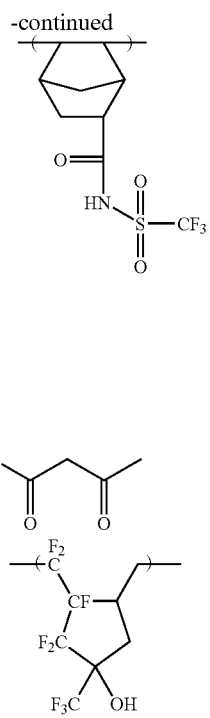

As the group (y) that is decomposed by the action of an alkali developer, resulting in an increase of solubility in the alkali developer, there can be mentioned, for example, a group having a lactone structure, an acid anhydride group, an acid imide group or the like. A group having a lactone structure is preferred.

As the repeating unit having a group (y) that is decomposed by the action of an alkali developer, resulting in an increase of solubility in the alkali developer, preferred use is made of both of a repeating unit resulting from bonding of a group (y) that is decomposed by the action of an alkali developer, resulting in an increase of solubility in the alkali developer, to the principal chain of a resin such as a repeating unit of acrylic ester or methacrylic ester, and a repeating unit resulting from polymerization with the use of a chain transfer agent or polymerization initiator having a group (y) resulting in an increase of solubility in an alkali developer to thereby introduce the same in a polymer chain terminal.

The content of repeating units having a group (y) resulting in an increase of solubility in an alkali developer is preferably in the range of 1 to 40 mol %, more preferably 3 to 30 mol % and still more preferably 5 to 15 mol % based on all the repeating units of the polymer.

As specific examples of the repeating units having a group (y) resulting in an increase of solubility in an alkali developer, there can be mentioned those similar to the repeating units having a lactone structure set forth with respect to the resins as the component (A).

As the repeating unit having a group (z) that is decomposed by the action of an acid in the hydrophobic resin (HR), there can be mentioned those similar to the repeating units having an acid decomposable group set forth with respect to the resin (A). The content of repeating units having a group (z) that is decomposed by the action of an acid in the hydrophobic resin (HR) is preferably in the range of 1 to 80 mol %, more preferably 10 to 80 mol % and still more preferably 20 to 60 mol % based on all the repeating units of the polymer.

The hydrophobic resin (HR) may further have any of the repeating units of the following general formula (IV).

In the general formula (IV), $R_{c31}$ represents a hydrogen atom, an alkyl group, an alkyl group substituted with a fluorine atom, a cyano group or $-CH_2-O-Rac_2$ group, wherein $Rac_2$ represents a hydrogen atom, an alkyl group or an acyl group. $R_{c31}$ is preferably a hydrogen atom, a methyl group, a hydroxymethyl group or a trifluoromethyl group, especially preferably a hydrogen atom or a methyl group.

$R_{c32}$ represents a group having any of an alkyl group, a cycloalkyl group, an alkenyl group and a cycloalkenyl group. These groups may optionally be substituted with a fluorine atom or a silicon atom.

$L_{c3}$ represents a single bond or a bivalent connecting group.

In the general formula (IV), the alkyl group represented by $R_{c32}$ is preferably a linear or branched alkyl group having 3 to 20 carbon atoms.

The cycloalkyl group is preferably a cycloalkyl group having 3 to 20 carbon atoms.

The alkenyl group is preferably an alkenyl group having 3 to 20 carbon atoms.

The cycloalkenyl group is preferably a cycloalkenyl group having 3 to 20 carbon atoms.

Preferably, $R_{c32}$ represents an unsubstituted alkyl group or an alkyl group substituted with a fluorine atom.

The bivalent connecting group represented by $L_{c3}$ is preferably an alkylene group (preferably having 1 to 5 carbon atoms), an oxy group, a phenylene group or an ester bond (group of the formula $-COO-$).

Further, the hydrophobic resin (HR) may preferably have any of the repeating units of general formula (CII-AB) below.

In the general formula (CII-AB), each of $R_{c11'}$ and $R_{c12'}$ independently represents a hydrogen atom, a cyano group, a halogen atom or an alkyl group.

$Zc'$ represents an atomic group for forming an alicyclic structure which contains two bonded carbon atoms (C—C).

Specific examples of the repeating units of the general formula (III) and general formula (CII-AB) will be shown below, which however in no way limit the scope of the present invention. In the formulae, Ra represents H, $CH_3$, $CH_2OH$, $CF_3$ or CN.

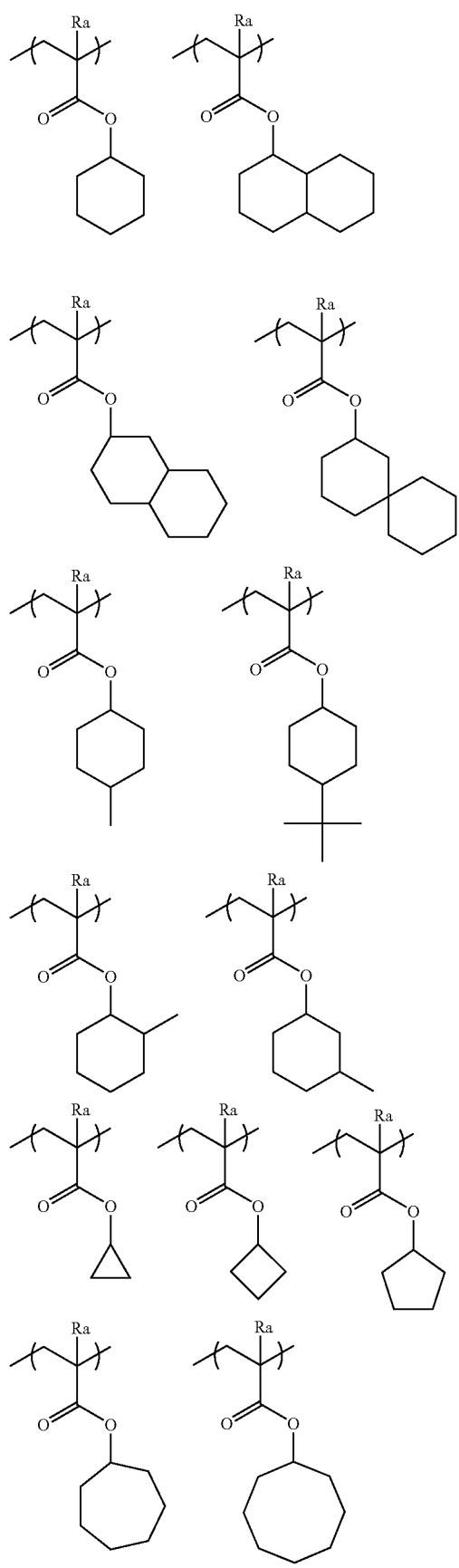
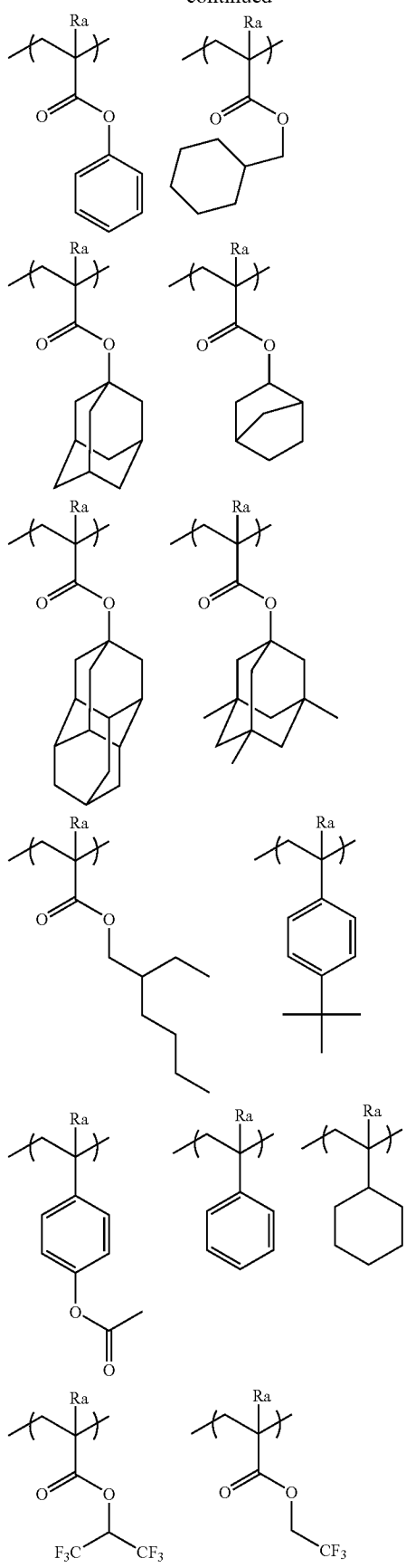

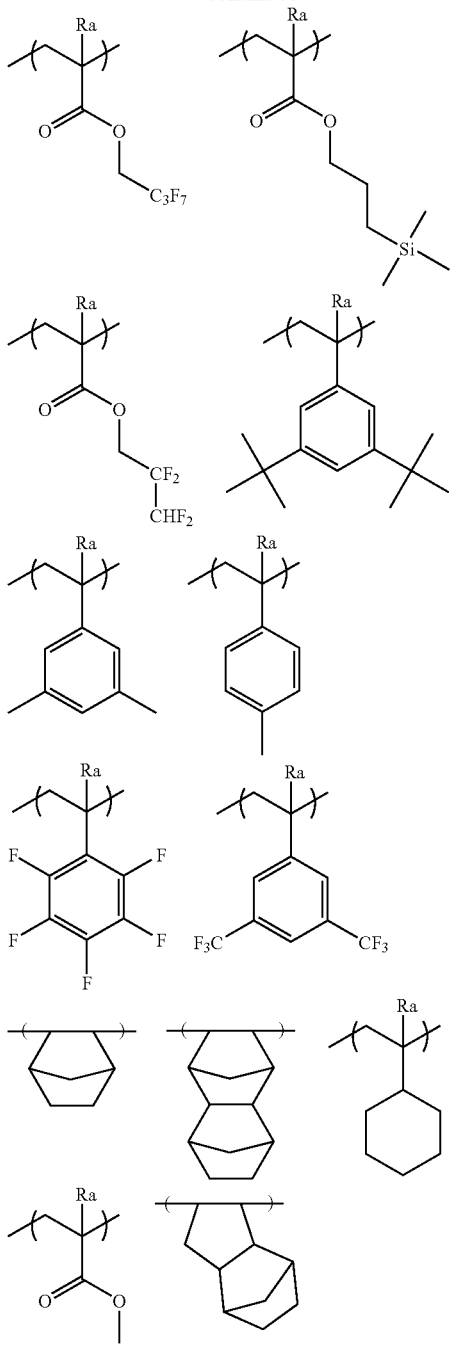

When the hydrophobic resin (HR) has a fluorine atom, the content of fluorine atom(s) is preferably in the range of 5 to 80 mass %, more preferably 10 to 80 mass %, based on the molecular weight of the hydrophobic resin (HR). The repeating unit containing a fluorine atom preferably exists in the hydrophobic resin (HR) in an amount of 10 to 100 mass %, more preferably 30 to 100 mass %.

When the hydrophobic resin (HR) has a silicon atom, the content of silicon atom(s) is preferably in the range of 2 to 50 mass %, more preferably 2 to 30 mass %, based on the molecular weight of the hydrophobic resin (HR). The repeating unit containing a silicon atom preferably exists in the hydrophobic resin (HR) in an amount of 10 to 100 mass %, more preferably 20 to 100 mass %.

The weight average molecular weight of the hydrophobic resin (HR) in terms of standard polystyrene molecular weight is preferably in the range of 1,000 to 100,000, more preferably 1,000 to 50,000 and still more preferably 2,000 to 15,000.

Impurities, such as metals, should naturally be of low quantity in the hydrophobic resin (HR), as for the resin as the component (A). The content of residual monomers and oligomer components is preferably 0 to 10 mass %, more preferably 0 to 5 mass % and still more preferably 0 to 1 mass %. Accordingly, there can be obtained a resist being free from a change of in-liquid foreign matter, sensitivity, etc. over time. From the viewpoint of resolving power, resist profile, side wall of resist pattern, roughness, etc., the molecular weight distribution (Mw/Mn, also referred to as the degree of dispersal) thereof is preferably in the range of 1 to 5, more preferably 1 to 3 and still more preferably 1 to 2.

A variety of commercially available products can be used as the hydrophobic resin (HR), and also the resin can be synthesized in accordance with conventional methods (for example, radical polymerization). As general synthesizing methods, there can be mentioned, for example, a batch polymerization method in which a monomer species and an initiator are dissolved in a solvent and heated to thereby carry out polymerization, a dropping polymerization method in which a solution of monomer species and initiator is dropped into a hot solvent over a period of 1 to 10 hours, and the like. The dropping polymerization method is preferred. As a reaction solvent, there can be mentioned, for example, an ether such as tetrahydrofuran, 1,4-dioxane or diisopropyl ether, a ketone such as methyl ethyl ketone or methyl isobutyl ketone, an ester solvent such as ethyl acetate, an amide solvent such as dimethylformamide or dimethylacetamide, or the aforementioned solvent capable of dissolving the composition of the present invention, such as propylene glycol monomethyl ether acetate, propylene glycol monomethyl ether or cyclohexanone. Preferably, the polymerization is carried out with the use of the same solvent as that used in the composition of the present invention. This would inhibit any particle generation during storage.

The polymerization reaction is preferably carried out in an atmosphere consisting of an inert gas, such as nitrogen or argon. In the initiation of polymerization, a commercially available radical initiator (azo initiator, peroxide, etc.) is used as the polymerization initiator. Among the radical initiators, an azo initiator is preferred, and azo initiators having an ester group, a cyano group and a carboxyl group are more preferred. As specific preferred initiators, there can be mentioned azobisisobutyronitrile, azobisdimethylvaleronitrile, dimethyl 2,2'-azobis(2-methylpropionate) and the like. The reaction concentration is in the range of 5 to 50 mass %, preferably 30 to 50 mass %. The reaction temperature is generally in the range of 10° to 150° C., preferably 30° to 120° C. and more preferably 60° to 100° C.

After the completion of the reaction, the mixture is allowed to stand still to cool to room temperature and purified. In the purification, use is made of routine methods, such as a liquid-liquid extraction method in which residual monomers and oligomer components are removed by water washing or by the use of a combination of appropriate solvents, a method of purification in solution form such as ultrafiltration capable of extraction removal of only components of a given molecular weight or below, a re-precipitation method in which a resin solution is dropped into a poor solvent to thereby coagulate the resin in the poor solvent and thus remove residual monomers, etc. and a method of purification in solid form such as washing of a resin slurry obtained by filtration with the use of a poor solvent. For example, the reaction solution is brought into contact with a solvent wherein the resin is poorly soluble or insoluble (poor solvent) amounting to 10 or less, preferably 10 to 5 times the volume of the reaction solution to thereby precipitate the resin as a solid.

The solvent for use in the operation of precipitation or re-precipitation from a polymer solution (precipitation or re-precipitation solvent) is not limited as long as the solvent is a poor solvent for the polymer. According to the type of polymer, use can be made of any one appropriately selected from among a hydrocarbon, a halogenated hydrocarbon, a nitro compound, an ether, a ketone, an ester, a carbonate, an alcohol, a carboxylic acid, water, a mixed solvent containing these solvents and the like. Of these, it is preferred to employ a solvent containing at least an alcohol (especially methanol or the like) or water as the precipitation or re-precipitation solvent.

The amount of precipitation or re-precipitation solvent used is generally in the range of 100 to 10,000 parts by mass, preferably 200 to 2000 parts by mass and more preferably 300 to 1000 parts by mass per 100 parts by mass of the polymer solution, according to intended efficiency, yield, etc.

The temperature at which the precipitation or re-precipitation is carried out is generally in the range of about 0° to 50° C., preferably about room temperature (for example, about 20° to 35° C.), according to efficiency and operation easiness. The operation of precipitation or re-precipitation can be carried out by a publicly known method, such as a batch or continuous method, with the use of a common mixing vessel, such as an agitation vessel.

The polymer obtained by the precipitation or re-precipitation is generally subjected to common solid/liquid separation, such as filtration or centrifugal separation, and dried before use. The filtration is carried out with the use of a filter medium ensuring solvent resistance, preferably under pressure. The drying is performed at about 30° to 100° C., preferably about 30° to 50° C. at ordinary pressure or reduced pressure (preferably reduced pressure).

Alternatively, after the resin precipitation and separation, the obtained resin may be once more dissolved in a solvent and brought into contact with a solvent wherein the resin is poorly soluble or insoluble. Specifically, the method may include the steps of, after the completion of the radical polymerization reaction, bringing the polymer into contact with a solvent wherein the polymer is poorly soluble or insoluble to thereby precipitate a resin (step a), separating the resin from the solution (step b), re-dissolving the resin in a solvent to thereby obtain a resin solution (A) (step c), thereafter bringing the resin solution (A) into contact with a solvent wherein the resin is poorly soluble or insoluble amounting to less than 10 times (preferably 5 times or less) the volume of the resin solution (A) to thereby precipitate a resin solid (step d) and separating the precipitated resin (step e).

Specific examples of the hydrophobic resins (HR) will be shown below. The following Table 1 shows the molar ratio of individual repeating units (corresponding to individual repeating units in order from the left), weight average molecular weight and degree of dispersal with respect to each of the resins.

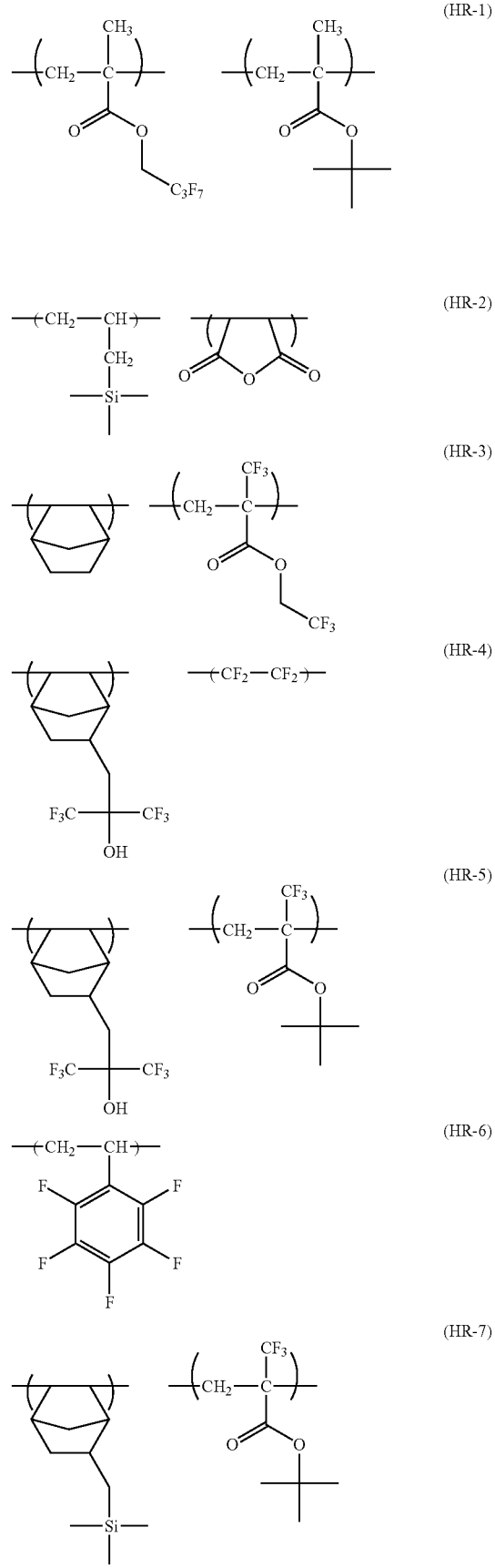

(HR-8)
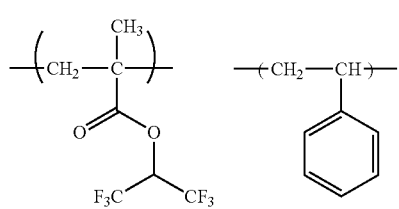
(HR-9)
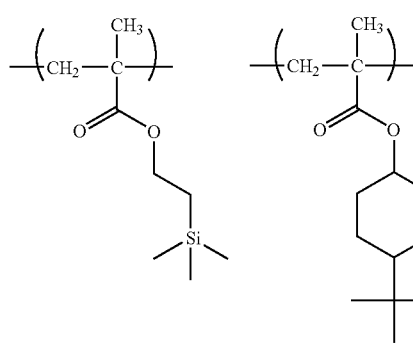
(HR-10)
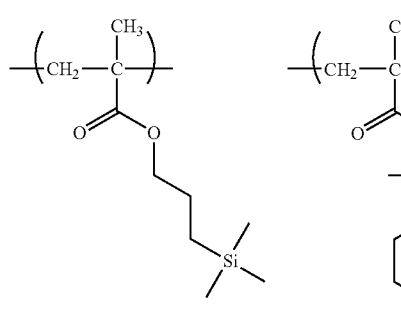
(HR-11)
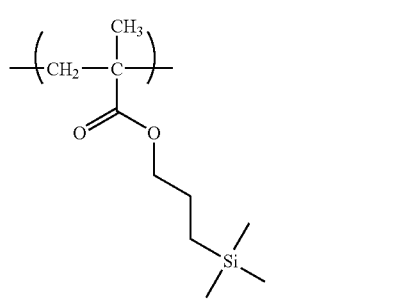
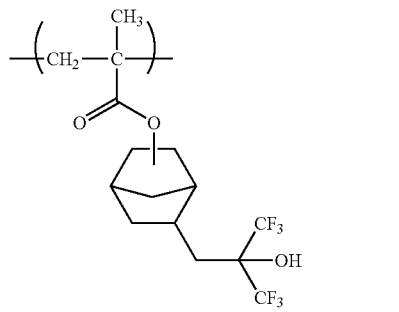
(HR-12)
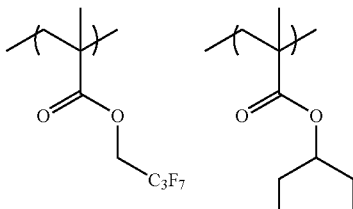
(HR-13)
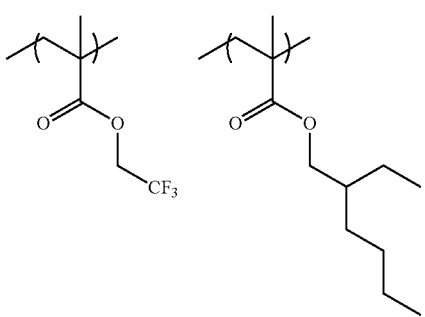
(HR-14)
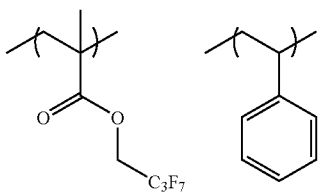
(HR-15)
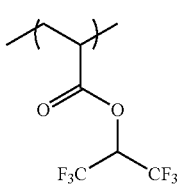
(HR-16)
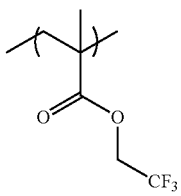
(HR-17)
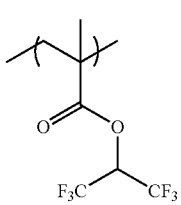

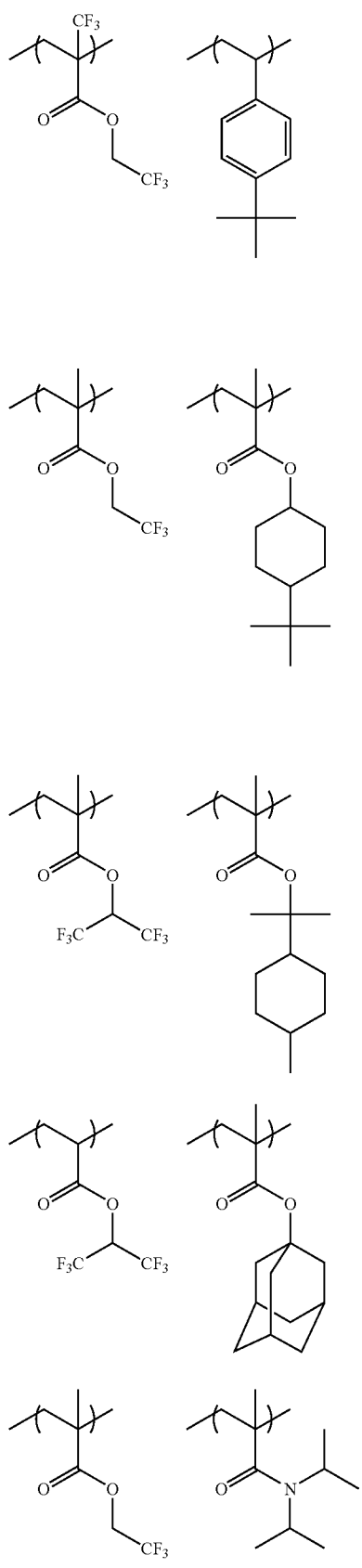

(HR-29)
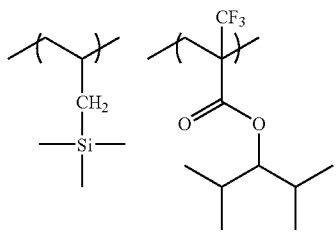
(HR-30)
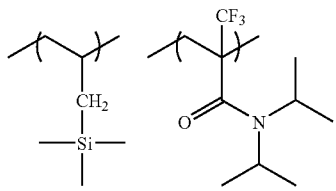
(HR-31)
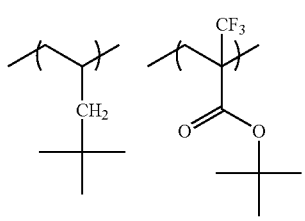
(HR-32)
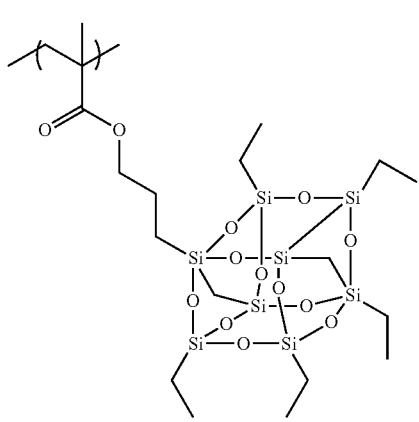
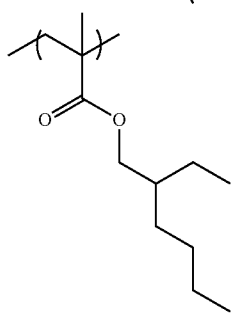
(HR-33)
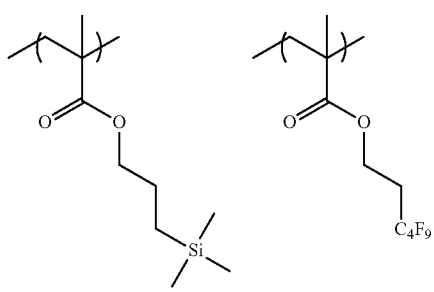
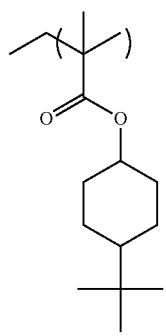
(HR-34)
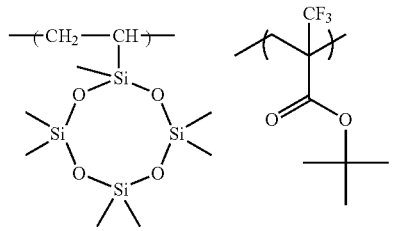
(HR-35)
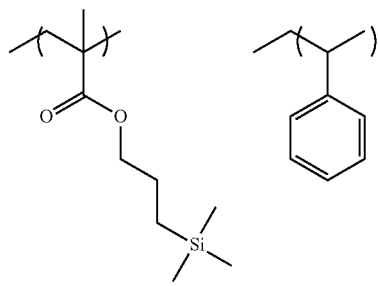
(HR-36)
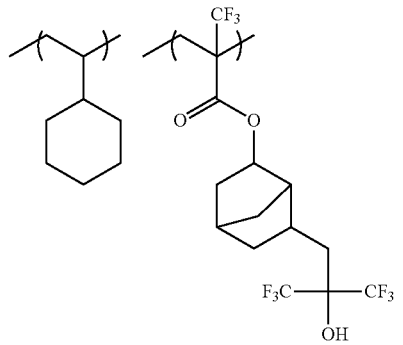
(HR-37)
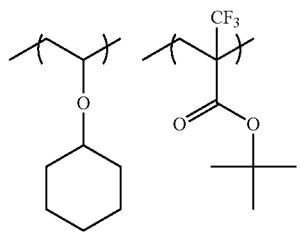

-continued
(HR-38)
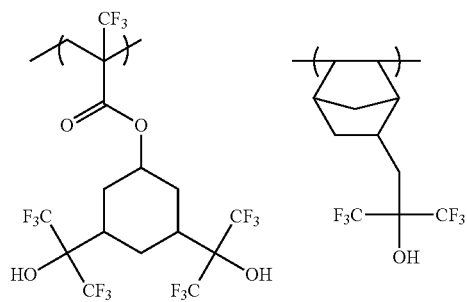
(HR-39)
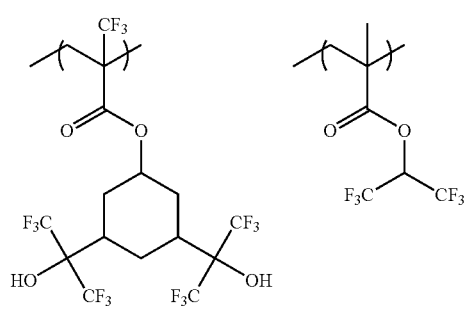
(HR-40)
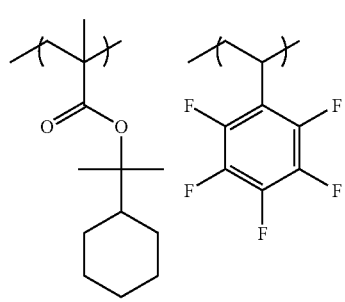
(HR-41)
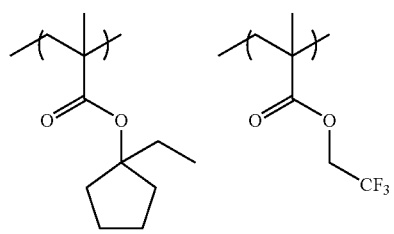
(HR-42)
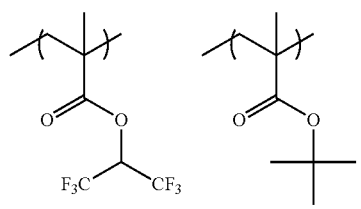
-continued
(HR-43)
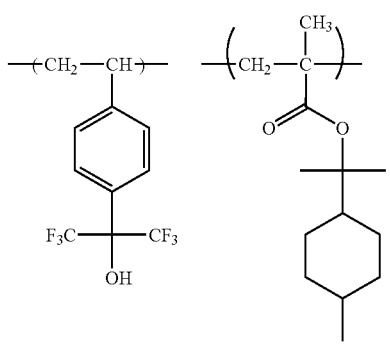
(HR-44)
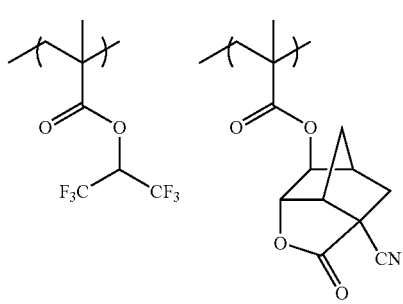
(HR-45)
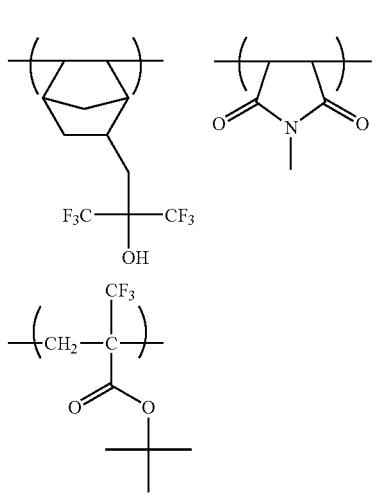
(HR-46)
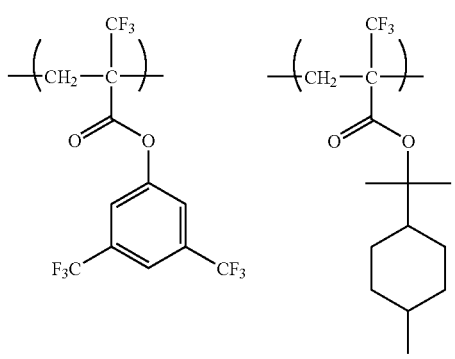

(HR-47)
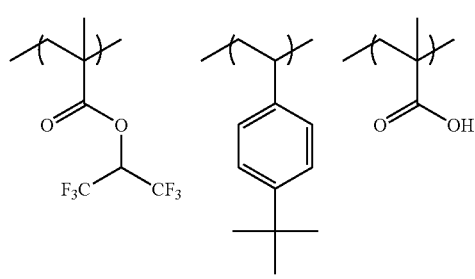
(HR-48)
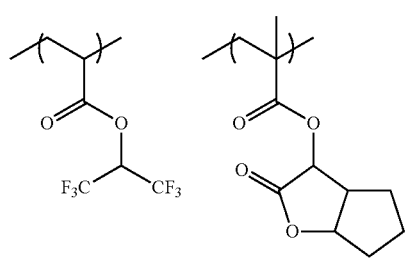
(HR-49)
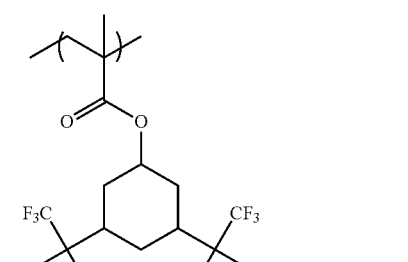
(HR-50)
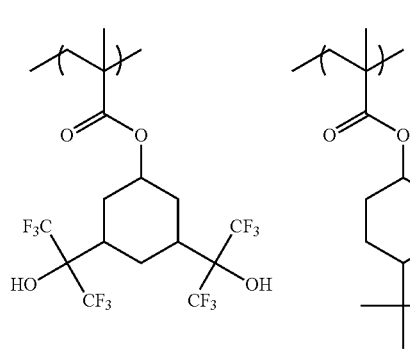
(HR-51)
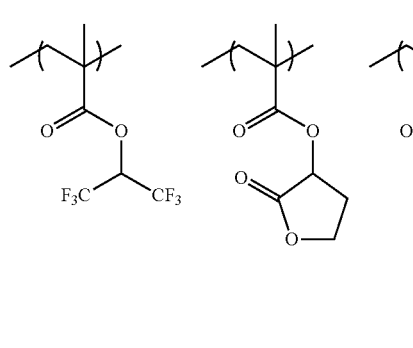
(HR-52)
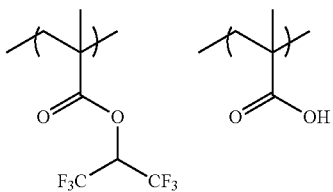
(HR-53)
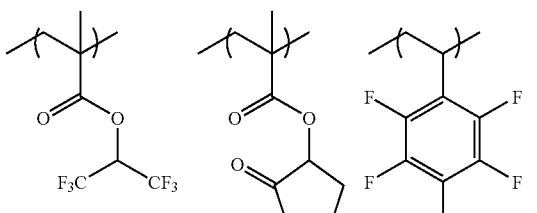
(HR-54)
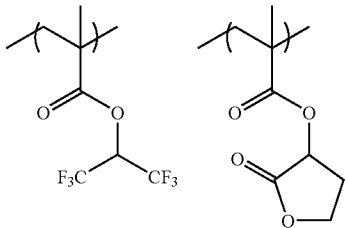
(HR-55)
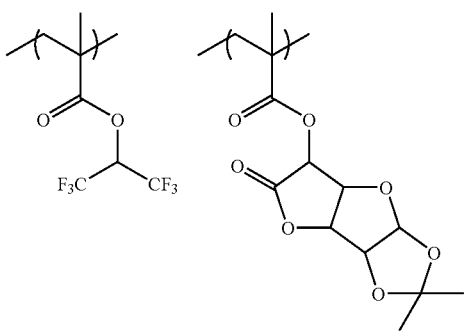
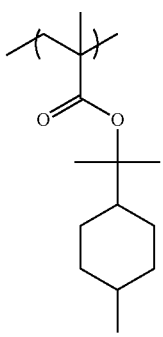

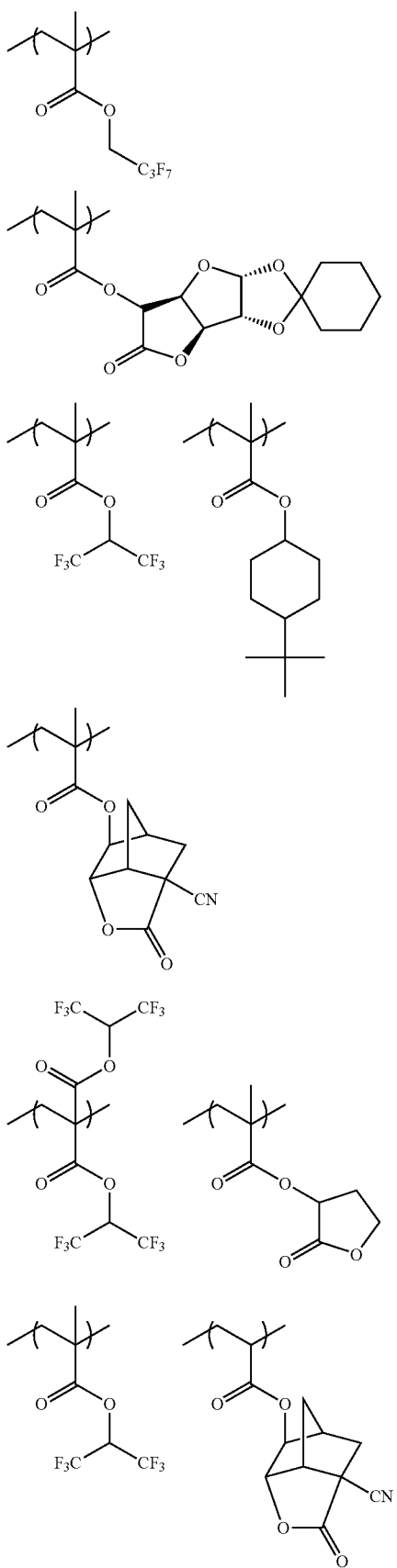
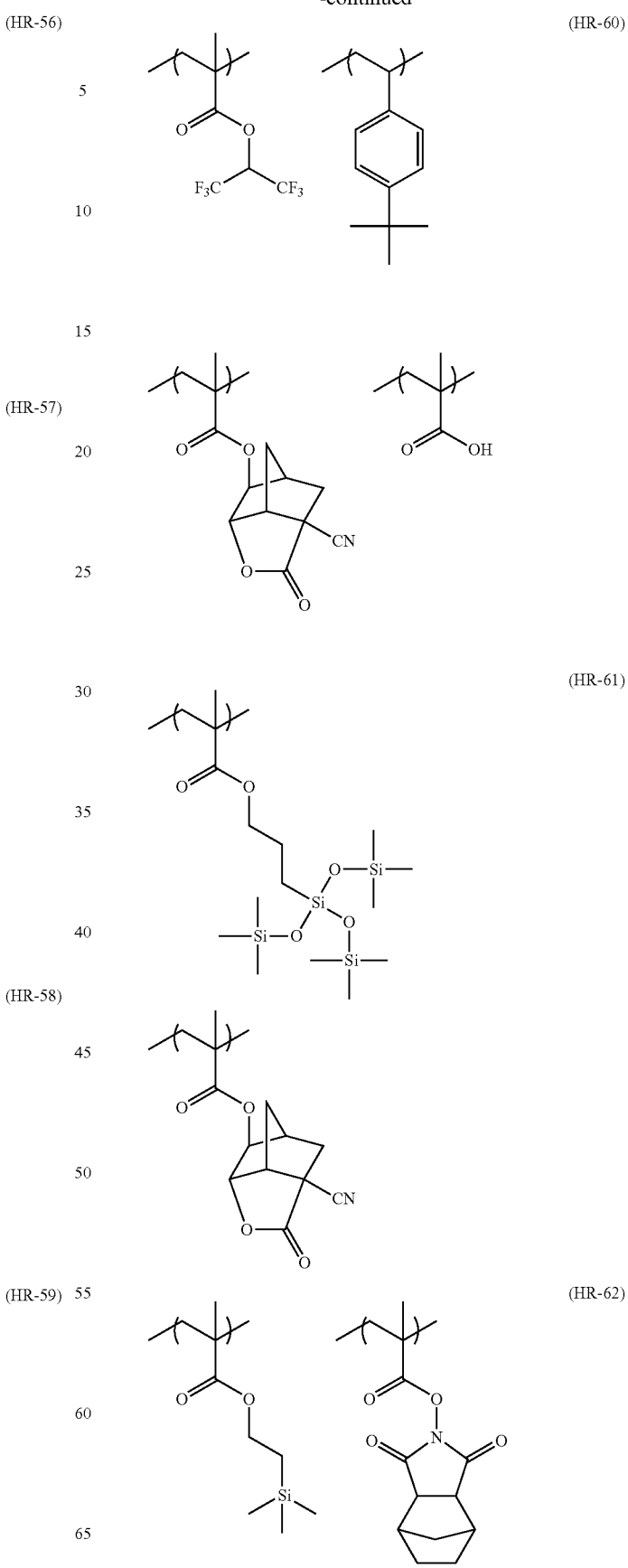

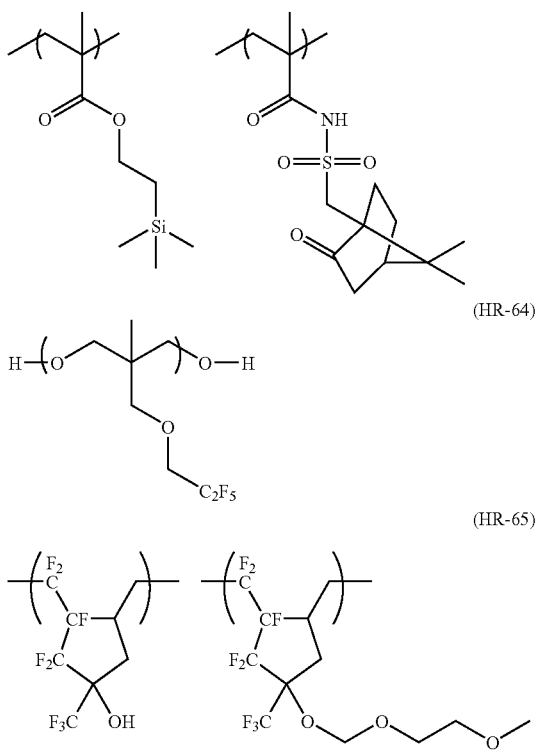

TABLE 1

| resin | composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |

For the prevention of direct contact of a film with a liquid for liquid immersion, a film that is highly insoluble in the liquid for liquid immersion (hereinafter also referred to as a "top coat") may be provided between the film from the actinic ray-sensitive or radiation-sensitive resin composition of the present invention and the liquid for liquid immersion. The functions to be fulfilled by the top coat are applicability to an upper layer portion of the film, transparency in radiation of especially 193 nm and being highly insoluble in the liquid for liquid immersion. Preferably, the top coat does not mix with the film and is uniformly applicable to an upper layer of the film.

From the viewpoint of 193 nm transparency, the top coat preferably consists of a polymer not abundantly containing an aromatic moiety. As such, there can be mentioned, for example, a hydrocarbon polymer, an acrylic ester polymer, polymethacrylic acid, polyacrylic acid, polyvinyl ether, a siliconized polymer, a fluoropolymer or the like. The aforementioned hydrophobic resins (HR) also find appropriate application in the top coat. From the viewpoint of contamination of an optical lens by leaching of impurities from the top coat into the liquid for liquid immersion, it is preferred to reduce the amount of residual monomer components of the polymer contained in the top coat.

At the detachment of the top coat, use may be made of a developer, or a separate peeling agent may be used. The peeling agent preferably consists of a solvent having a lower permeation into the resist film. Detachability by an alkali developer is preferred from the viewpoint of simultaneous attainment of the detachment step with the development processing step for the film. The top coat is preferred to be acidic from the viewpoint of detachment with the use of an alkali developer. However, from the viewpoint of non-intermixability with the resist film, the top coat may be neutral or alkaline.

The less the difference in refractive index between the top coat and the liquid for liquid immersion, the higher the resolving power. In an ArF excimer laser (wavelength: 193 nm), when water is used as the liquid for liquid immersion, the top coat for ArF liquid immersion exposure preferably has a refractive index close to that of the liquid for liquid immersion. From the viewpoint of approximation of the refractive index to that of the liquid for liquid immersion, it is preferred for the top coat to contain a fluorine atom. From the viewpoint of transparency and refractive index, it is preferred to reduce the thickness of the film.

Preferably, the top coat does not mix with the film and also does not mix with the liquid for liquid immersion. From this viewpoint, when the liquid for liquid immersion is water, it is preferred for the solvent used in the top coat to be highly insoluble in the solvent used in the actinic ray-sensitive or radiation-sensitive resin composition and be a non-water-soluble medium. When the liquid for liquid immersion is an organic solvent, the top coat may be soluble or insoluble in water.

EXAMPLES

Examples 1 to 12 and Comparative Examples 1 to 5

Synthesis of Resin (A)

(Resin (A1))

In a nitrogen stream, 78.1 g of cyclohexanone was placed in a three-necked flask and heated at 80° C. A solution obtained by dissolving the following monomer (A), monomer (B), monomer (C) and monomer (D) amounting to 18.3 g, 3.8 g, 5.5 g and 11.8 g, respectively and further 2.418 g of a polymerization initiator (dimethyl 2,2'-azobis(2-methylpropionate) (V601) produced by Wako Pure Chemical Industries, Ltd.) in 145.0 g of cyclohexanone was dropped thereinto over a period of 6 hours.

After the completion of the dropping, reaction was continued at 80° C. for 2 hours. The reaction mixture was allowed to stand still to cool and was dropped into a mixed liquid consisting of heptane/ethyl acetate (1290 g/551 g) over a period of 20 min. The thus precipitated powder was collected by filtration and dried, thereby obtaining 35 g of a desired resin (A1). The weight average molecular weight (Mw) of the obtained resin in terms of standard polystyrene molecular weight was 9200 and the degree of dispersal (Mw/Mn) thereof was 1.55.

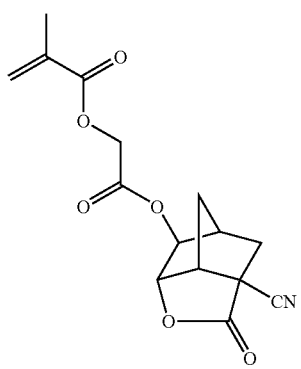

Monomer A

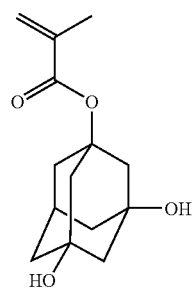

Monomer B

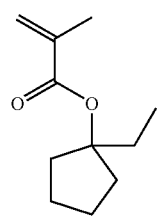

Monomer C

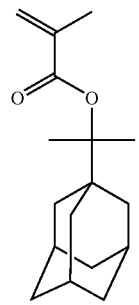

Monomer D (Resins (A2) to (A12))

Resins (A2) to (A12) were synthesized in the same manner as described for the resin (A1) (Examples 2 to 12 and Comparative Examples 1 to 5).

The structural units and compositional ratios thereof employed in the production of the resins (As) and the weight average molecular weights (Mw) and degrees of dispersal (Mw/Mn) of the obtained resins (As) are given in the following Table 2.

TABLE 2

| | Resin(A) | |
|---|---|---|
| Copolymer component and Component ratio | Weight average molecular weight | Degree of dispersal |
| (A1) A/B/C/D = 4/1/2/3 | 9200 | 1.55 |
| (A2) A/B/C/D = 4/1/2/3 | 9100 | 1.57 |
| (A3) E/B/C/F = 4/1/2/3 | 9350 | 1.53 |
| (A4) A/G/C/F = 4/1/2/3 | 9000 | 1.49 |
| (A5) A/B/C/F = 4/1/2/3 | 8900 | 1.58 |
| (A6) A/B/H/D = 4/1/3/2 | 9150 | 1.54 |
| (A7) I/G/C/J = 4/1/2/3 | 9030 | 1.44 |
| (A8) A/B/K/D = 5/1/2/2 | 9230 | 1.53 |
| (A9) I/G/L/D = 4/1/2/3 | 9350 | 1.52 |
| (A10) I/B/C/F = 4/1/2/3 | 9060 | 1.51 |
| (A11) A/B/M/N = 5/1/2/2 | 9010 | 1.53 |
| (A12) O/G/H/N = 4/1/2/3 | 9800 | 1.49 |
| (A13) A/B/C/D/P = 4/1/2/2/1 | 9000 | 1.45 |

The compounds corresponding to the brevity codes of the Table 2 are shown below.
[Resin Structural Unit]
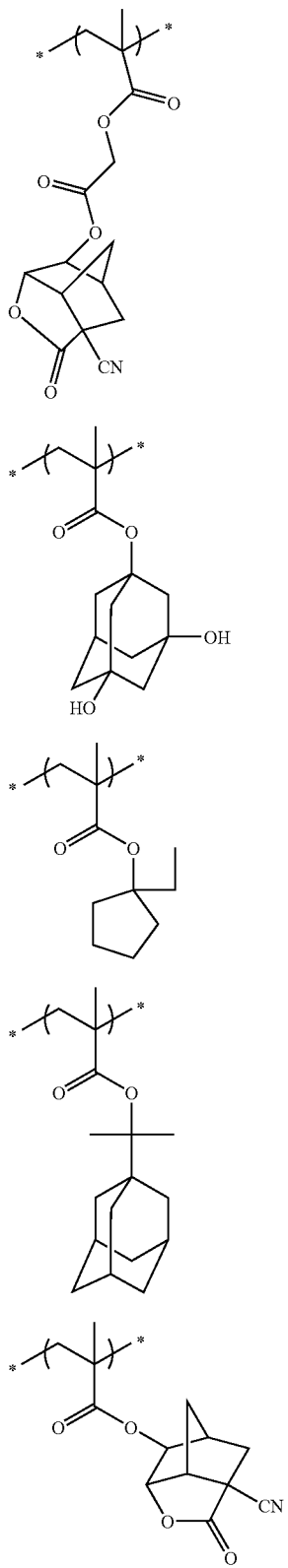
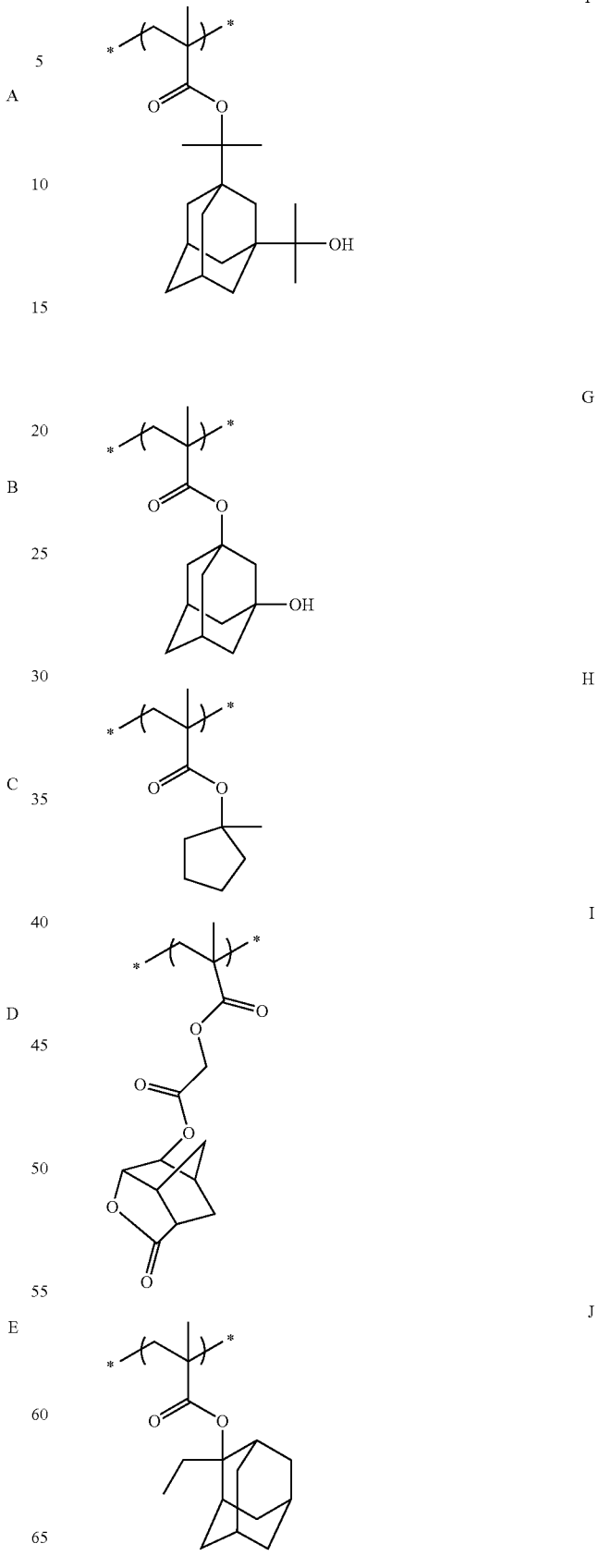

K

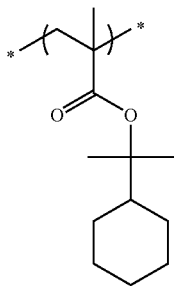

L

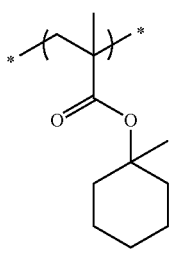

M

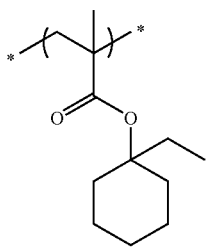

N

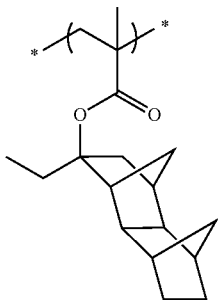

O

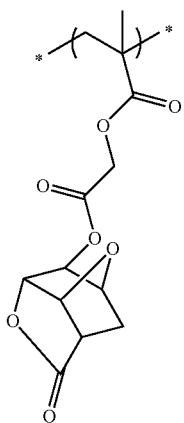

P

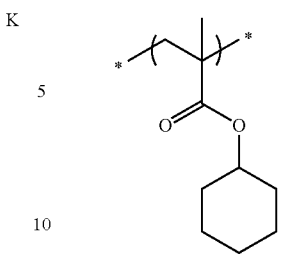

<Preparation of Resist Composition>

The components indicated in the following Table 3 were dissolved in a 6/4 mixed solvent of propylene glycol methyl ether acetate/propylene glycol methyl ether, thereby obtaining a solution of 3.5 mass % solid content. This solution was passed through a polyethylene filter of 0.03 μm pore size, thereby obtaining a positive resist solution. The thus obtained positive resist solution was evaluated by the following methods.

Resin: 50 g,
sulfonic acid generator: 4 g,
acid diffusion inhibitor: 0.12 g,
surfactant* (PF6320 (produced by OMNOVA, fluorinated):
0.05 g, and
solvent: propylene glycol methyl ether acetate/propylene glycol methyl ether=60%/40%.
* With respect to Example 18, no surfactant was used.

<Measurement of pKa>

The calculation of pKa was conducted with the use of a software package produced by ACD (Advanced Chemistry Development) "ACD/pKa DBV8.0." In the calculation, use is made of a program for calculating the acid dissociation constant (pKa) in an aqueous solution (25° C., ionic strength 0) with respect to each arbitrary organic structure. The calculation is performed using Hammett's formula, substituent constants and database of publicly known values (including 16,000 chemical structures and 31,000 or more actual measurement values). The ±95% confidence limit, ±0.2 pKa unit values are output. With respect to polybasic acids, the calculation is performed taking the statistical factor thereof into account.

<Evaluation of Resist>

An organic antireflection film ARC29A (produced by Nissan Chemical Industries, Ltd.) was applied onto a silicon wafer and baked at 205° C. for 60 sec, thereby forming a 78 nm antireflection film. The prepared positive resist composition was applied thereonto and baked at 130° C. for 60 sec, thereby forming a 120 nm resist film. The resultant wafer was exposed through a 6% half-tone mask of 75 nm 1:1 line and space pattern with the use of an ArF excimer laser scanner (manufactured by ASML, PAS5500/1100, NA0.75). Thereafter, the exposed wafer was heated at 90° C. for 60 sec, developed with an aqueous solution of tetramethylammonium hydroxide (2.38 mass %) for 30 sec, rinsed with pure water and spin dried, thereby obtaining a resist pattern.

[Exposure Latitude (EL)]

The optimum exposure intensity is defined as the exposure intensity that reproduces a 75 nm line width, line and space mask pattern. The exposure intensity width in which when the exposure intensity is varied, the pattern size allows 85 nm±10% is measured. The exposure latitude is the quotient of the value of the exposure intensity width divided by the optimum exposure intensity, the quotient expressed by a percentage. The greater the value of the exposure latitude, the less the change of performance by exposure intensity changes and the better the exposure latitude (EL).

[Evaluation of LWR]

The line pattern finished at 75 nm in the standard resist evaluation was observed by means of a scanning electron microscope (model S-9260, manufactured by Hitachi, Ltd.). With respect to a 2 μm region of each longitudinal edge of the line pattern, the distance from a reference line on which the edge was to be present was measured at 50 points. The standard deviation thereof was determined, and 3σ was computed. The smaller the value thereof, the higher the performance exhibited.

[Evaluation of Pattern Collapse]

The optimum exposure intensity refers to the exposure intensity that reproduces a 75 nm line-and-space mask pattern. The exposure intensity was increased from the optimum exposure intensity to cause the line width of the formed line pattern to be finer. The critical pattern collapse was defined as the line width allowing pattern resolution without any collapse. The smaller the value thereof, the finer the pattern is resolved without any collapse, that is, the more effective the suppression of pattern collapse and the higher the resolving power.

[Sulfonic Acid Generator]

Sulfonic acid generator A

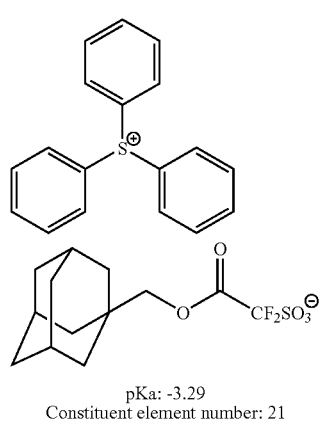

pKa: -3.29
Constituent element number: 21

Sulfonic acid generator B

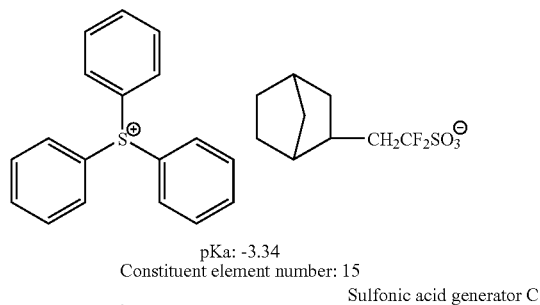

pKa: -3.34
Constituent element number: 15

Sulfonic acid generator C

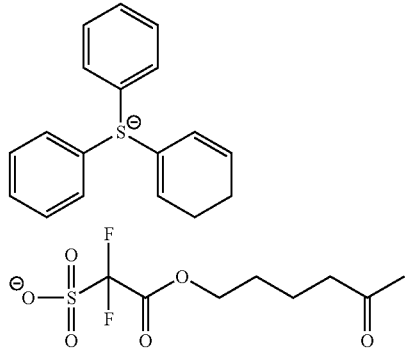

-continued

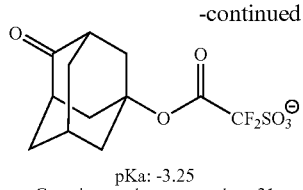

pKa: -3.25
Constituent element number: 21

Sulfonic acid generator D

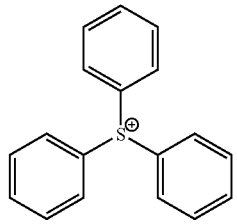

pKa: -3.30
Constituent element number: 20

Sulfonic acid generator E

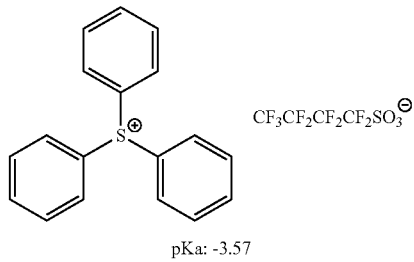

pKa: -3.57
Constituent element number: 17

Sulfonic acid generator F

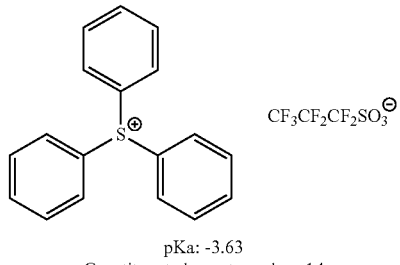

pKa: -3.63
Constituent element number: 14

Sulfonic acid generator G pKa: -3.31
Constituent element number: 17

-continued

Sulfonic acid generator H

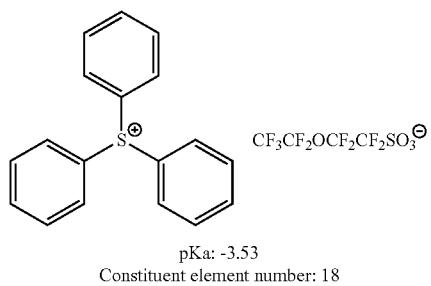

pKa: -3.53
Constituent element number: 18

Sulfonic acid generator I

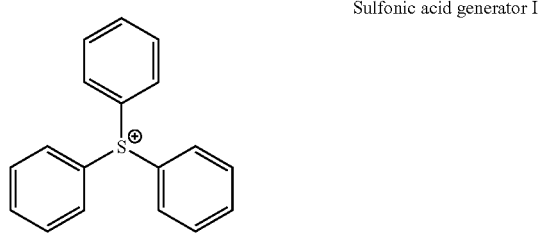

pKa: -3.21
Constituent element number: 17

Sulfonic acid generator J

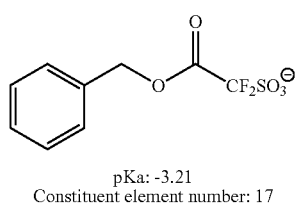

pKa: -3.63
Constituent element number: 14

Sulfonic acid generator K

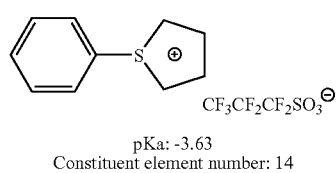

pKa: -3.57
Constituent element number: 17

-continued

Sulfonic acid generator L

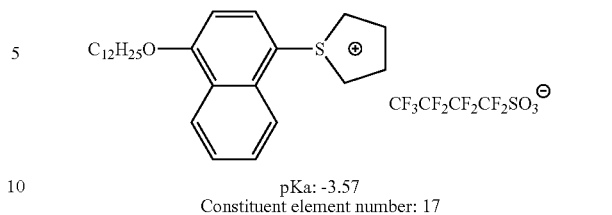

pKa: -3.57
Constituent element number: 17

Sulfonic acid generator M

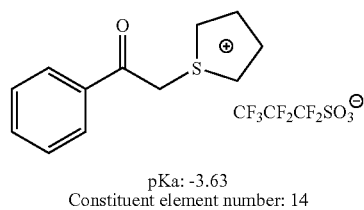

pKa: -3.63
Constituent element number: 14

Sulfonic acid generator N

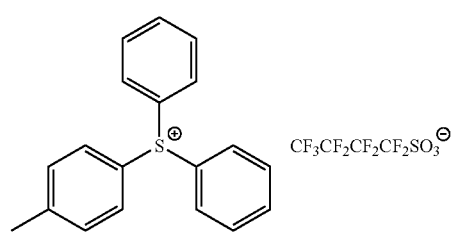

pKa: -3.57
Constituent element number:: 17

Comparative Example

[Sulfonic Acid Generator]

Sulfonic acid generator O

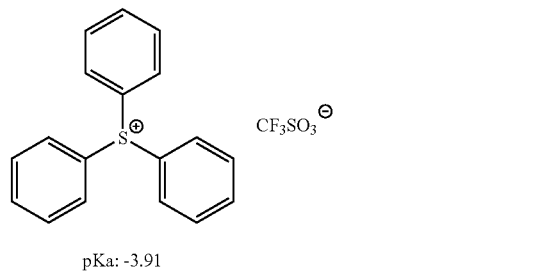

pKa: -3.91
Constituent element number: 8

Sulfonic acid generator P

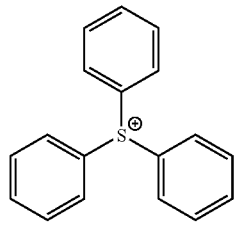
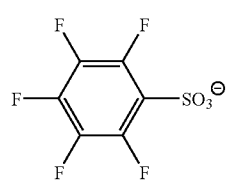

pKa: -2.22

Constituent element number:15

Sulfonic acid generator Q

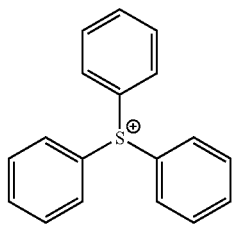
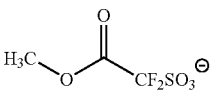

pKa: -3.35

Constituent element number:11

[Acid Diffusion Inhibitor]
X-1: 2,6-diisopropylaniline,
X-2: 2-phenylbenzimidazole, and
X-3: tri-n-octylamine.

TABLE 3

| | | Sulfonic Acid Generator B1 | Sulfonic Acid Generator B2 | Acid diffusion inhibitor | lithography performance | | | |
|---|---|---|---|---|---|---|---|---|
| | Resin | | | | Optimum Exposure Intensity (mJ/cm$^2$) | EL (%) | LWR (nm) | Pattern collapse (nm) |
| Ex. 1 | A1 | E(70%) | A(30%) | X-1(100%) | 37.5 | 13.5 | 7.5 | 39.0 |
| Ex. 2 | A2 | E(40%) | A(60%) | X-1(20%), X-2(80%), | 36.0 | 14.9 | 7.1 | 35.5 |
| Ex. 3 | A3 | E(30%) | B(70%) | X-1(100%) | 37.0 | 13.2 | 7.4 | 40.5 |
| Ex. 4 | A4 | F(70%) | A(30%) | X-1(70%), X-3(30%), | 38.0 | 15.2 | 7.1 | 35.5 |
| Ex. 5 | A5 | F(50%) | C(50%) | X-1(100%) | 37.5 | 13.5 | 7.5 | 39.5 |
| Ex. 6 | A6 | H(70%) | D(30%) | X-1(100%) | 39.0 | 13.5 | 8.0 | 42.0 |
| Ex. 7 | A7 | F(20%) | G(80%) | X-1(100%) | 38.5 | 13.2 | 7.9 | 42.0 |
| Ex. 8 | A8 | F(40%) | B(60%) | X-2(100%) | 39.0 | 14.1 | 8.0 | 40.5 |
| Ex. 9 | A9 | H(50%) | B(50%) | X-3(100%) | 38.5 | 13.2 | 8.2 | 43.5 |
| Ex. 10 | A10 | F(30%) | A(30%) B(40%) | X-1(100%) | 38.0 | 14.3 | 7.9 | 42.5 |
| Ex. 11 | A11 | F(20%) | G(80%) | X-1(100%) | 39.5 | 13.5 | 8.3 | 42.0 |
| Ex. 12 | A12 | E(50%) | I(50%) | X-1(100%) | 52.0 | 12.5 | 7.5 | 38.5 |
| Ex. 13 | A1 | J(70%) | A(30%) | X-1(100%) | 48.2 | 13.1 | 7.2 | 38.5 |
| Ex. 14 | A1 | K(50%) | A(50%) | X-1(100%) | 45.3 | 14.0 | 7.0 | 39.2 |
| Ex. 15 | A1 | L(30%) | A(70%) | X-1(100%) | 40.2 | 13.6 | 7.3 | 40.3 |
| Ex. 16 | A1 | M(40%) | A(60%) | X-1(100%) | 43.6 | 12.9 | 7.6 | 39.5 |
| Ex. 17 | A1 | N(50%) | A(50%) | X-1(100%) | 38.2 | 13.7 | 7.7 | 41.2 |
| Ex. 18 | A1 | E(70%) | A(30%) | X-1(100%) | 37.3 | 13.6 | 7.4 | 38.8 |
| Comp. 1 | A12 | E(100%) | — | X-1(100%) | 37.0 | 9.5 | 8.1 | 41.0 |
| Comp. 2 | A12 | — | B(100%) | X-1(100%) | 45.5 | 12.5 | 9.3 | 59.0 |
| Comp. 3 | A12 | O(50%) | B(50%) | X-1(100%) | 33.0 | 8.5 | 8.2 | 55.3 |
| Comp. 4 | A12 | E(50%) | Q(50%) | X-1(100%) | 37.0 | 10.3 | 9.1 | 43.5 |
| Comp. 5 | A12 | E(50%) | P(50%) | X-1(100%) | 55.5 | 12.4 | 8.5 | 60.3 |

* % of each of sulfonic acid generators (B1) and (B2) indicates mass % based on the total mass of sulfonic acid B.

** % of acid diffusion inhibitor indicates mass % based on total mass of acid diffusion inhibitor.

As apparent from the results of Table 3, it has been proved that all the photosensitive compositions of the present invention are superior in the exposure latitude, LWR and pattern collapse to the photosensitive compositions of Comparative Examples 1 to 5. Further, an enhancement of sensitivity at the optimum exposure intensity was attained by the employment of a structure containing no benzene ring structure in the acid generated by irradiation with actinic rays or radiation as the sulfonic acid generator capable of generating a sulfonic acid contained in the photosensitive composition.

In the following Examples 19 and 20, resist patterns were formed by liquid immersion exposure. Ultrapure water was used as the liquid for liquid immersion.

Example 19

Resist production and application were carried out by exactly the same operation as in Example 5 except that 0.10 g of the following polymer was further added, thereby obtaining a resist film. The obtained resist film was subjected to patterning exposure using an ArF excimer laser liquid immersion stepper (NA0.85), thereby forming the same pattern as in Example 1. It has been ascertained that similar results can be obtained in all of the exposure latitude, LWR and pattern collapse performances.

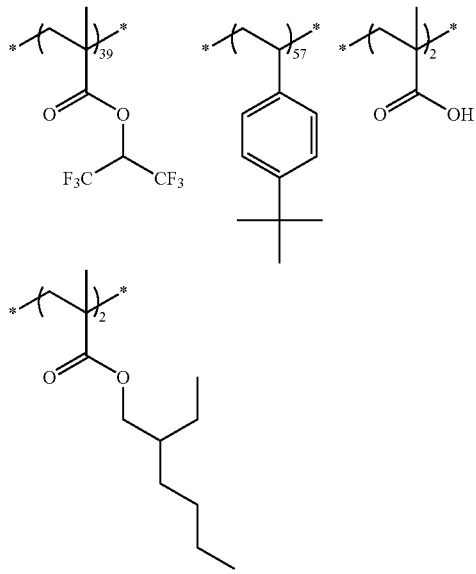

Weight average molecular weight 4500
Degree of dispersal 1.4

Example 20

Resist production and application were carried out by exactly the same operation as in Example 5 except that 0.10 g of the following polymer was further added, thereby obtaining a resist film. The obtained resist film was subjected to patterning exposure using an ArF excimer laser liquid immersion stepper (NA0.85), thereby forming the same pattern as in Example 1. It has been ascertained that similar results can be obtained in all of the exposure latitude, LWR and pattern collapse performances.

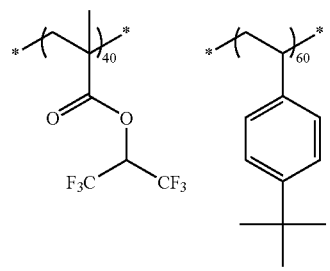

Weight average molecular weight 4300
Degree of dispersal 1.4

It has been ascertained by these Examples 19 and 20 that the actinic ray-sensitive or radiation-sensitive resin compositions of the present invention can also be appropriately used in the pattern formation by an ArF excimer laser liquid immersion exposure.

What is claimed is:
1. An actinic ray-sensitive or radiation-sensitive resin composition comprising:
(A) a resin that exhibits an increased solubility in an alkali developer when acted on by an acid, and
(B) at least two types of sulfonic acid generators that generate a sulfonic acid when exposed to actinic rays or radiation,
wherein the two types of sulfonic acid generators (B) consist of sulfonic acid generators (B1) and (B2) satisfying the following requirements:
the sulfonic acid generator (B1) generates a sulfonic acid composed of 9 to 20 elements with an acid strength (pKa) satisfying the relationship pKa <−3.50, and
the sulfonic acid generator (B2) generates a sulfonic acid composed of 17 or more elements with an acid strength (pKa) satisfying the relationship −2.00>pKa≥−3.50,
provided that no hydrogen atom is included in the number of elements of the generated acids, and
the sulfonic acid generator (B2) contains an anionic structure of the formula Rb—X—CF$_2$—SO$_3$— in which X represents CH$_2$ and Rb represents a structure consisting of a combination of two or more members, selected from among an oxygen atom, a sulfur atom, a nitrogen atom, a carbon atom and a hydrogen atom, and Rb contains polycyclic organic group;
wherein the resin (A) contains a repeating unit represented by the following general formula (AI):

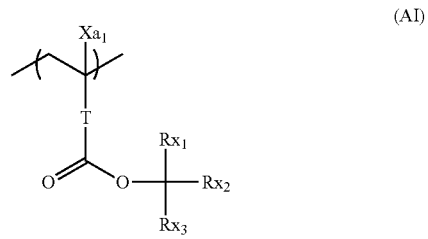

wherein,
Xa$_1$ represents a hydrogen atom, a methyl group, a trifluoromethyl group or a hydroxymethyl group,
T represents a single bond or a bivalent connecting group, and each of Rx$_1$ to Rx$_3$ independently represents an alkyl group (linear or branched) or a cycloalkyl group (monocyclic or polycyclic), provided that at least two of Rx$_1$ to Rx$_3$ may be bonded with each other to thereby form a cycloalkyl group (monocyclic or polycyclic).

2. The actinic ray-sensitive or radiation-sensitive resin composition according to claim 1, wherein no benzene ring structure is contained in the acids generated by the sulfonic acid generators (B1) and (B2).

3. The actinic ray-sensitive or radiation-sensitive resin composition according to claim 1, further comprising two or more types of acid diffusion inhibitors (C) capable of controlling the diffusion of the acids generated from the sulfonic acid generators (B).

4. A method of forming a pattern, comprising the steps of applying the actinic ray-sensitive or radiation-sensitive resin composition according to claim 1 onto a substrate, exposing the substrate to actinic rays or radiation and developing the exposed substrate with a developer.

5. The actinic ray-sensitive or radiation-sensitive resin composition according to claim 1, wherein the resin (A) contains two or more types of repeating units each having acid-decomposable group.

6. The actinic ray-sensitive or radiation-sensitive resin composition according to claim 1, wherein the resin (A) contains a repeating unit which does not have a hydroxyl group or a cyano group, but contains a hydrocarbon group having at least one cyclic structure.

7. The actinic ray-sensitive or radiation-sensitive resin composition according to claim 1, wherein the anionic structure of the sulfonic acid generator (B1) is represented by Ra—CF$_2$—CF$_2$—SO$_3$—, and Ra represents a structure consisting of any one, or a combination of two or more members, selected from among an oxygen atom, a sulfur atom, a nitrogen atom, a carbon atom, a hydrogen atom and a fluorine atom.

8. The actinic ray-sensitive or radiation-sensitive resin composition according to claim 1, wherein the resin (A) further contains a repeating unit having a lactone group.

9. The actinic ray-sensitive or radiation-sensitive resin composition according to claim 1, wherein the resin (A) contains no aromatic group.

10. The actinic ray-sensitive or radiation-sensitive resin composition according to claim 1, in the resin (A), all the repeating units consist of (meth)acrylate repeating units.

11. The actinic ray-sensitive or radiation-sensitive resin composition according to claim 1, further comprising a hydrophobic resin (HR).

12. The actinic ray-sensitive or radiation-sensitive resin composition according to claim 11, wherein an addition amount of the hydrophobic resin (HR) is in the range of 0.1 to 10 mass % based on the total solids of the composition.

13. The actinic ray-sensitive or radiation-sensitive resin composition according to claim 12, wherein the hydrophobic resin (HR) contains at least one group selected from among the following groups (x) to (z):

(x) an alkali soluble group, (y) a group that is decomposed by the action of an alkali developer, resulting in an increase of solubility in the alkali developer, and (z) a group that is decomposed by the action of an acid.

14. The actinic ray-sensitive or radiation-sensitive resin composition according to claim 1, wherein the polycyclic organic group is polycyclic cycloalkyl group.

15. The actinic ray-sensitive or radiation-sensitive resin composition according to claim 1, wherein the polycyclic organic group is adamantyl group.

16. The actinic ray-sensitive or radiation-sensitive resin composition according to claim 1, wherein Rb represents a structure consisting of any one, or a combination of two or more members, selected from among an oxygen atom, a carbon atom and a hydrogen atom.

* * * * *